United States Patent [19]

Shiba et al.

[11] Patent Number: 5,629,188
[45] Date of Patent: May 13, 1997

[54] HUMAN ALANYL-TRNA SYNTHETASE PROTEINS, NUCLEIC ACIDS AND TESTER STRAINS COMPRISING SAME

[75] Inventors: Kiyotaka Shiba, Tokyo, Japan; Paul R. Schimmel, Cambridge; Tracy L. Ripmaster, Charlestown, both of Mass.

[73] Assignees: Cubist Pharmaceuticals, Inc., Cambridge, Mass.; Cancer Institute, Japanese Foundation for Cancer Research, Tokyo, Japan; Massachusetts Institute of Technology, Cambridge, Mass.

[21] Appl. No.: 426,236

[22] Filed: Apr. 21, 1995

[51] Int. Cl.$^6$ .............. C12N 9/00; C12N 1/20; C12N 1/14; C07H 21/04
[52] U.S. Cl. .............. 435/183; 435/240.1; 435/252.3; 435/254.11; 435/320.1; 536/23.2
[58] Field of Search .............. 435/183, 240.1, 435/252.3, 254.11, 320.1; 536/23.2

[56] References Cited

U.S. PATENT DOCUMENTS

| | | | |
|---|---|---|---|
| 4,713,337 | 12/1987 | Jasin et al. | 435/172.3 |
| 4,952,501 | 8/1990 | Jasin et al. | 435/69.2 |
| 4,963,487 | 10/1990 | Schimmel et al. | 435/172.3 |
| 5,484,703 | 1/1996 | Raben et al. | 435/7.4 |

OTHER PUBLICATIONS

Edwards, H., et al., "An *E. coli* Aminoacyl–tRNA Synthetase Can Substitute for Yeast Mitochondrial Enzyme Function In Vivo," *Cell* 51:643–649, Nov. 20, 1987.
Racher, K.I., et al., "Expression and Characterization of a Recombinant Yeast Isoleucyl–tRNA Synthetase," *The Journal of Biological Chemistry* 266(26):17158–17164, Sep. 15, 1991.
von der Haar, F. et al., "Target Directed Drug Synthesis: The Aminoacyl–tRNA Synthetases as Possible Targets," *Angew. Chem. Int. Ed.*, 20(3):217–223 (1981).
Chalker, A.F., et al., "Analysis and Toxic Overexpression in *Escherichia coli* of a Staphylococcal Gene Encoding Isoleucyl–tRNA Synthetase," *Gene*, 141:103–108 (1994).
Hughes, J. and Mellows, G., "Interaction of Pseudomonic Acid A with *Escherichia coli* B Isoleucyl–tRNA Synthetase," *Biochem J.*, 191:209–219 (1980).
Weygand–Durašević, I., et al., "Yeast Seryl–tRNA Synthetase Expressed in *Escherichia coli* Recognizes Bacterial Serine–Specific tRNAs in vivo," *Eur. J. Biochem.*, 214:869–877 (1993).
Walter, R. D. and Kuhlow, F., "Parasite–Specific Interaction of N–[4–(4' Nitroanilino)–Phenyl]–S–(β–Carboxyethyl)– Dithiocarbamic Acid–Ester with Arginyl–tRNA–Synthetase from *Dirofilaria immitis*," *Trop. Med. Parasit.*, 36:230–232 (1985).
Meinnel, T., et al., "Aminoacyl–tRNA Synthetases: Occurrence, Structure, and Function." In *tRNA: Structure, Biosynthesis, and Function*, Söll, D. and RajBhandary, U., eds. (Washington, DC: American Society for Microbiology), pp. 251–300 (1995).

Hou, Y.–M., and Schimmel, P., "Evidence That a Major Determinant for the Indentify of a Transfer RNA Is Conserved in Evolution," *Biochemistry*, 28:6800–6804 (1989).

Sequence of *Saccharomyces cerevisiae* Cytoplasmic Alanyl––tRNA Synthetase Gene, Complete cds, GenBank Accession: U18672 (2 pages). Entered by Ripmaster, T. L. First available Jan. 2, 1995.

Biswas, T., et al., "An Enzyme–Linked Immunosorbent Assay for the Detection and Quantitation of Anti–Jo–1 Antibody in Human Serum," *Journal of Immunological Methods*, 98:243–248 (1987).

Raben, N., "Improved Assay Using Recombinant Histidyl––tRNA Synthetase," *U.S. Department of Commerce National Technical Information Service*, Report No. PAT–APPL–8–052 404, filing date: 22 Apr. 1993.

Bunn, C. C., et al., "Autoantibodies Against Alanyl–tRNA Synthetase and tRNA$^{Ala}$ Coexist and are Associated with Myositis," *J. Exp. Med.*, 163:1281–1291 (1986).

Bunn, C. and Mathews, M. B., "Autoreactive Epitope Defined as the Anticodon Region of Alanine Transfer RNA," *Science*, 238:1116–1119 (1987).

Herlihy, W. C., et al., "Mass Spectra of Partial Protein Hydrolysates as a Multiple Phase Check for Long Polypeptides Deduced from DNA Sequences: NH$_2$–Terminal Segment of Alanine tRNA Synthetase," *Proc. Natl. Acad. Sci. USA*, 77(11):6531–6535 (1980).

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

Isolated, recombinant nucleic acids which encode alanyl-tRNA synthetase (AlaRS) of human origin have been used to make expression constructs and transformed host cells for the production of recombinant human AlaRS. The recombinant enzyme has been purified, and is active in the specific aminoacylation of tRNA by alanine. The isolated, recombinant human AlaRS is also recognized by antibodies made by patients with the particular autoimmune disease known as "antisynthetase syndrome" in which the patients produce antibodies against the human alanyl-tRNA synthetase in their own cells. Thus, the isolated, recombinant enzyme, and antibodies made specifically thereto, can be useful in assays to diagnose and monitor this disease. The essential alanyl-tRNA synthetases of microbes pathogenic in humans can be the targets of inhibitory agents having antimicrobial activity. The human alanyl-tRNA synthetase, isolated and purified, can be used to assess the toxic effect in humans of such an inhibitory agent in various biochemical activity assays. This human enzyme can also be expressed in "tester strains," whose cells rely upon the function of the human alanyl-tRNA synthetase for tRNA$^{Ala}$ charging. Such tester strains can be used to test for any toxic effects of an antimicrobial agent that specifically interacts with the heterologous human AlaRS gene or gene product.

33 Claims, 8 Drawing Sheets

OTHER PUBLICATIONS

Chang, P. K. and Dignam, J. D., "Primary Structure of Alanyl–tRNA Synthetase and the Regulation of Its mRNA Levels in *Bombyx mori*," *The Journal of Biological Chemistry*, 265(34):20898–20906 (1990).

Selbitschka, W., et al., "Characterization of recA Genes and recA Mutants of *Rhizobium meliloti* and *Rhizobium leguminosarum* Biovar viciae," *Mol. Gen. Genet*, 229:86–95 (1991).

Jasin, M. and Schimmel, P., "Deletion of an Essential Gene in *Escherichia coli* by Site–Specific Recombination with Linear DNA Fragments," *J. Bacteriol.* 159(2):783–786 (1984).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology*, 10(4):1633–1642 (1990).

Hughes, J., et al., "Inhibition of Isoleucyl–Transfer Ribonucleic Acid Synthetase in *Escherichia coli* by Pseudomonic Acid," *Biochem. J.* 176:305–318 (1978), Great Britain.

Putney, S.D., et al., "Primary Structure of a Large Aminoacyl–tRNA Synthetase," *Science*, 213:1497–1501 (1981).

Sequence of *Arabidopsis thaliana* Alanyl–tRNA Synthetase Gene. Mireau, H., et al., EMBL Accession No. Z22673 (4 pages). File created May 7, 1993.

Wiesenberger, G., et al., "The Nuclear Gene MRS2 Is Essential for the Excision of Group II Introns from Yeast Mitochondrial Transcripts in Vivo," *The Journal of Biological Chemistry*, 267(10):6963–6969 (1992).

Targoff, I. N., and Arnett, F. C., "Clinical Manifestations in Patients with Antibody to PL–12 Antigen (Alanyl–tRNA Synthetase)," *The American Journal of Medicine* 88:241–251 (1990).

Dignam, J.D., et al., "Alanyl–tRNA Synthetase from *Escherichia coli, Bombyx mori* and *Ratus ratus*, Existence of Common Structural Features," *Eur. J. Biochem.*, 198:201–210 (1990).

Ripmaster et al. (1995) Proc. Natl. Acad. Sci. USA 92: 4932–4936.

Schimmel et al. (1980) Macromolecules 13: 716–721.

Shiba et al. (1995) Biochemistry 34: 10340–10349.

FIG. 6

*E. coli*

```
         A⁷⁶
         C
         C
        [A]⁷³
 ¹G  —  C
  [G  —  C]
 ³ G  =  U ⁷⁰
   G  —  C
   C  —  G  -----
   U  —  A  -----
   A  —  U  -----
   A  —  U
   G  —  C
```

Human

```
         A
         C
         C
        [A]
   G  —  C
  [G  —  C]
   G  =  U  → C
   G  —  C
   G  —  C
   A  —  U
   U  —  A
   A  —  U
   G  —  C
```

HUMAN ALANYL-TRNA SYNTHETASE PROTEINS, NUCLEIC ACIDS AND TESTER STRAINS COMPRISING SAME

GOVERNMENT SUPPORT

Portions of the work described herein were done with government support under Grant numbers 15539 and 23561 awarded by the National Institutes of Health. Therefore, the government has certain rights to such work.

BACKGROUND OF THE INVENTION

The aminoacyl-tRNA synthetases are enzymes with the common general function of catalyzing the following reaction:

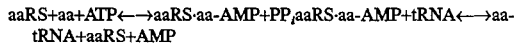

(aaRS=aminoacyl-tRNA synthetase; aa=amino acid; ATP= adenosine 5'-triphosphate; AMP=adenosine 5'-monophosphate; $PP_i$=inorganic pyrophosphate) The second (aminoacylation) step is often referred to as "charging" the tRNA.

Generally, in each eucaryotic organism, there are 20 different cytoplasmic aaRSs, one specific for each amino acid. Eucaryotic organisms also generally encode a separate set of mitochondrial aaRSs. It is known that in the yeast *Saccharomyces cerevisiae*, for example, the cytoplasmic and mitochondrial enzymes are encoded by separate nuclear genes, with the exception of histidyl- and valyl-tRNA synthetases (Natsoulis, G., et al. *Cell* 46:235-243 (1986); Chatton, B. et al., *J. Biol. Chem.* 263:52-57 (1988)). Each aminoacyl-tRNA synthetase enzyme recognizes and reacts with a specific amino acid and one or more tRNAs that recognize the codons specific for that amino acid (cognate tRNAs). To a first approximation, the specificity of the aaRS for the amino acid is determined by protein-amino acid interactions, and the specificity of the aaRS for the tRNA is determined by protein-RNA interactions, using different sites on the aaRS.

About 25-30% of patients suffering from one or both of the autoimmune inflammatory myopathies polymyositis and dermatomyositis have been found to produce antibodies against their own essential aminoacyl-tRNA synthetase enzymes. The resulting "antisynthetase syndrome" is characterized by a number of clinical presentations, including interstitial lung disease, arthritis, Raynaud's phenomenon and fevers, along with the muscle weakness, dyspnea and dysphagia of myositis. (See, for example, Targoff, I. N. et al., *J. Clin. Invest.* 91:2556-2564 (1993)).

Without sufficiently purified human aminoacyl-tRNA synthetases, the process of diagnosing the "antisynthetase syndrome" and identifying the particular antigenic aminoacyl-tRNA synthetase has been cumbersome. One semi-quantitative method available to measure anti-tRNA synthetase antibody in patient serum has been to measure the inhibition of an aminoacylation reaction, testing each one of 20 radioactively labeled amino acids to identify the type of tRNA synthetase. Improved assays would be desirable.

Because the amino acid sequences of the tRNA synthetases have diverged over evolutionary time, significant differences exist between the structures of the tRNA synthetases of humans and of human pathogens. These differences can be exploited by finding inhibitors of aaRS activity which specifically target a tRNA synthetase of a pathogenic organism. By selectively inactivating one or more aminoacyl-tRNA synthetases of a pathogenic organism with a therapeutic substance that minimally affects the corresponding human enzyme, infections by pathogenic organisms can be controlled.

The isolated, recombinant human alanyl-tRNA synthetase can be used in enzymatic activity and other biochemical assays to test substances found to inhibit the alanyl-tRNA synthetase or other tRNA synthetase of a pathogenic organism. The isolated human alanyl-tRNA synthetase can also be used in further studies to model substances with inhibitory activity specific for a tRNA synthetase of a pathogen.

In a second general type of assay, a tester strain is constructed such that it relies upon the function of a human alanyl-tRNA synthetase gene instead of the endogenous host gene of the cell strain. Such tester strains can be used to isolate the in vivo effect of a substance administered to the cells on the human alanyl-tRNA synthetase; that is, to assess by growth rates and other tests whether the substance has any toxicity by its effect specifically on the human alanyl-tRNA synthetase.

SUMMARY OF THE INVENTION

The invention relates to isolated and/or recombinant nucleic acids which encode alanyl-tRNA synthetase (AlaRS) of human origin. (Generically, the aminoacyl-tRNA synthetases are the aaRSs; in particular, they are, for example, AlaRS.) The invention also relates to recombinant DNA constructs and vectors containing DNA having a sequence which encodes an alanyl-tRNA synthetase of human origin, or portions of the enzyme. These nucleic acids and DNA constructs can be employed to produce recombinant alanyl-tRNA synthetase of human origin in host cells constructed for this purpose.

A further embodiment of the invention is antisense nucleic acid which can hybridize to the nucleic acid which encodes the amino acid sequence of alanyl-tRNA synthetase of humans. In cells, antisense nucleic acid can inhibit the function of an RNA which encodes the alanyl-tRNA synthetase.

The invention also relates to proteins or polypeptides which are referred to herein as isolated and/or recombinant human alanyl-tRNA synthetases, including functional portions of the tRNA synthetase and fusion proteins comprising a human AlaRS or a portion thereof. These enzymes can be used in the diagnosis and/or monitoring of patients suffering from autoimmune disorders associated with the production of autoantibodies against human alanyl-tRNA synthetase. These enzymes are also useful in biochemical separations of alanine and quantitations of alanine and ATP. Antibodies which bind to these enzymes can be made and can be used in the purification and study of the enzyme, for example in mapping antigenic epitopes of the enzyme. The antibodies can also be used as controls in assays for autoantibodies against human alanyl-tRNA synthetase found in samples from patients, such as sera.

Recombinant aminoacyl-tRNA synthetases can be produced in host cells, using cells and methods described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by an introduced cloned gene, where the introduced cloned gene is from either a pathogen or from an animal (or humans) infected by a pathogen. In this way, potential inhibitors of a tRNA synthetase from a pathogen can be tested for toxicity specifically caused by the inhibition of the corresponding (specific for the same amino acid) animal or human tRNA synthetase enzyme.

The invention also relates to essentially pure nucleic acids, recombinant vectors and host cells that can be used in the production of alanyl-tRNA synthetase of *Saccharomyces cerevisiae*. *S. cerevisiae* strains having a mutation in ALA1 and which can be conveniently used in the construction of tester strains for AlaRSs in general, are also an embodiment of the invention.

BRIEF DESCRIPTION OF THE DRAWINGS

FIG. 6 is a diagram showing synthetic RNA duplex substrates based on sequences of an *E. coli* and a human tRNA$^{Ala}$. These substrates consist of the acceptor stems from *E. coli* tRNA$^{Ala}$ or human tRNA$^{Ala}$ and the first two basepairs of the *E. coli* TψC-helical stem. The critical G3:U70 basepair is shaded and other nucleotides shown to be important in the *E. coli* system are boxed. Positions where the substrates differ are joined by dashed lines.

DETAILED DESCRIPTION OF THE INVENTION

Nucleic Acids, Constructs and Vectors

Figure 1:
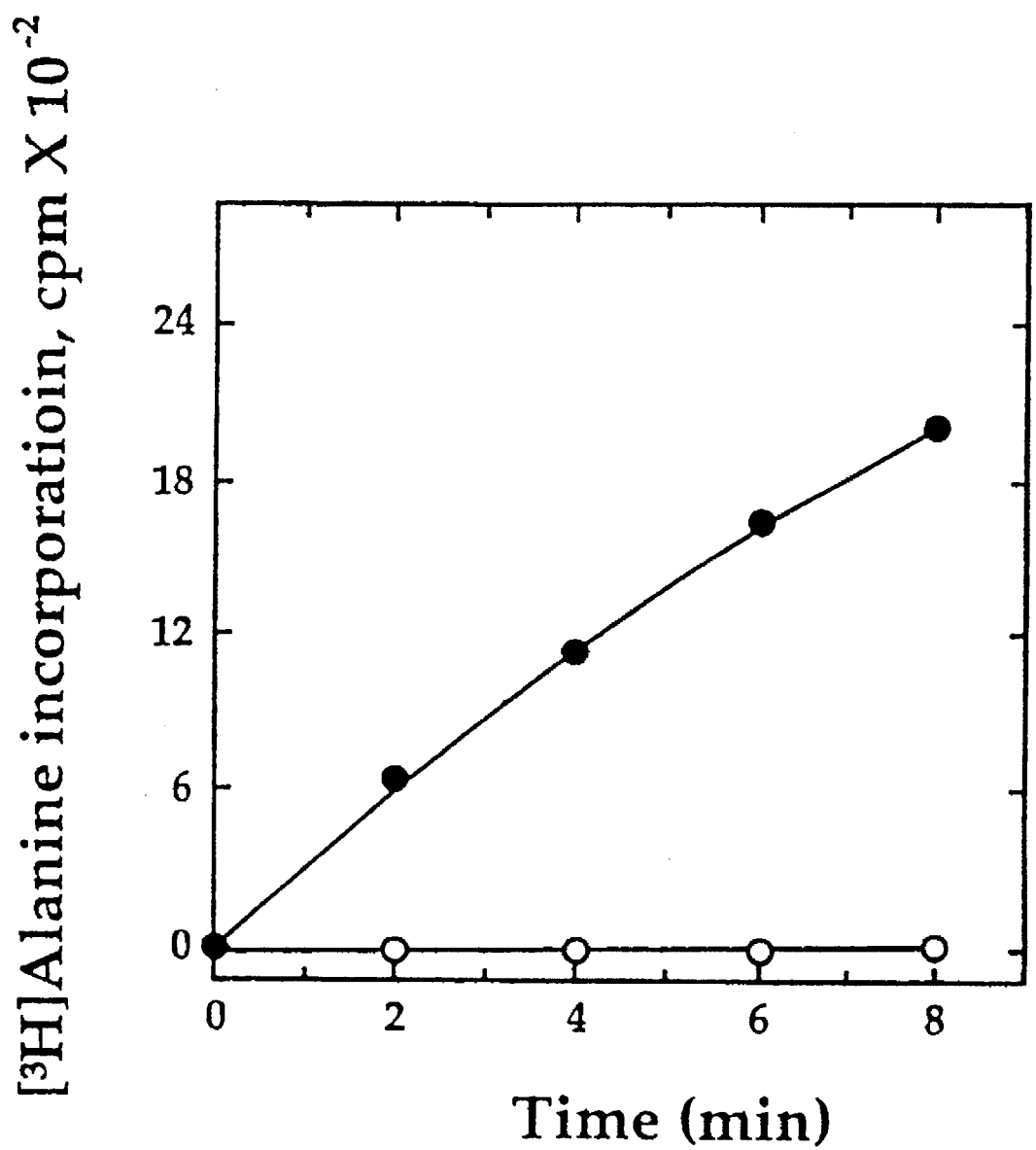
FIG. 1 is a graph showing the species specific aminoacylation of bovine tRNA with [$^3$H]-alanine as a function of time, by an extract of *P. pastoris* strain NOR-Aa6 (closed circles), which carries the human alanyl-tRNA synthetase gene, or by an extract of *P. pastoris* strain NOR-0 (open circles), which is isogenic with NOR-Aa6, except that it does not carry the human alanyl-tRNA synthetase gene (Example 6).

The present invention relates to isolated and/or recombinant (including, e.g., essentially pure) nucleic acids having sequences which encode a human alanyl-tRNA synthetase, or a portion of a human alanyl-tRNA synthetase. In one embodiment, the nucleic acid or portion thereof encodes a protein or polypeptide having at least one function characteristic of a human aminoacyl-tRNA synthetase specific for alanine, such as a catalytic activity (e.g., catalysis of aminoacyl-adenylate formation, catalysis of aminoacylation of a tRNA with alanine) and/or binding function (e.g., tRNA-, amino acid-, or ATP-binding), an antigenic property characteristic of a human alanyl-tRNA synthetase and/or oligomerization function. (Oligomerization activity is the ability of a protein subunit or protein fragment to bind together with one or more other protein subunits or protein fragments, thus altering the quaternary structure of the resulting complex. In one embodiment, the resulting complex has a new or enhanced activity of a type other than oligomerization, compared to the separate components of the complex. For example, "adhesive" fragments with oligomerization activity can bind to another fragment with no catalytic activity of its own to restore or partially restore catalytic activity (Jasin, M., et al., U.S. Pat. No. 4,952,501)).

The present invention also relates more specifically to isolated and/or recombinant nucleic acids or a portion thereof having sequences which encode alanyl-tRNA synthetase or a portion thereof, of human origin.

The invention further relates to isolated and/or recombinant nucleic acids that are characterized by (1) their ability to hybridize to (a) a nucleic acid encoding a human alanyl-tRNA synthetase such as that having the sequence of nucleotides 111–3014 in SEQ ID NO:1 or (b) its complement, or (c) to a portion of either of the foregoing, or (2) by their ability to encode a polypeptide of the amino acid sequence of the enzyme, such as SEQ ID NO:2, or functional equivalents thereof (e.g., a polypeptide which aminoacylates the isoaccepting cognate tRNA$^{Ala}$ of humans), or (3) by both characteristics. In one embodiment, the percent amino acid sequence similarity between SEQ ID NO:2 and functional equivalents thereof is at least about 65%. In a preferred embodiment, functional equivalents of SEQ ID NO:2 share at least about 70% sequence similarity with SEQ ID NO:2. More preferably, the percent amino acid sequence similarity between SEQ ID NO:2 and functional equivalents thereof is at least about 75%, and still more preferably, at least about 80%. Isolated and/or recombinant nucleic acids meeting these criteria comprise nucleic acids having sequences identical to sequences of naturally occurring human alanyl-tRNA synthetase and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in*

*Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity.

Isolated and/or recombinant nucleic acids that are characterized by their ability to hybridize to a nucleic acid encoding a human alanyl-tRNA synthetase or a portion thereof, or to their complements (e.g. under high or moderate stringency conditions) may further encode a protein or polypeptide having at least one function characteristic of a human tRNA synthetase specific for alanine, such as a catalytic activity (e.g., aminoacyl-adenylate formation, aminoacylation of a tRNA with alanine), binding function (e.g., tRNA-, amino acid-, or ATP-binding), an antigenic property characteristic of a human alanyl-tRNA synthetase, such as the ability to bind antibodies that also bind to naturally-occurring human alanyl-tRNA synthetase, and/or oligomerization function. The catalytic or binding function of a protein or polypeptide encoded by hybridizing nucleic acid may be detected by standard enzymatic assays for activity or binding (e.g., assays which monitor aminoacyl-adenylate formation, aminoacylation of tRNA). Functions characteristic of the alanyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:2 or functional equivalents thereof. The antigenic properties of proteins or polypeptides encoded by hybridizing nucleic acids can be determined by immunological methods employing antibodies that bind to a human alanyl-tRNA synthetase, such as immunoblot, immunoprecipitation and radioimmunoassay.

Nucleic acids of the present invention can be used in the production of proteins or polypeptides. For example, DNA containing all or part of the coding sequence for human alanyl-tRNA synthetase, or DNA which hybridizes to the sequence SEQ ID NO:1, or to its complement, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a human alanyl-tRNA synthetase can also refer to one of two or more distinct subunits of said alanyl-tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein. T residues of the DNA are U residues in the RNA counterpart). When introduced into a cell, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of the sequence shown in SEQ ID NO:1. For example, antisense nucleic acid can be complementary to a target nucleic acid having the sequence shown in SEQ ID NO:1 or a portion thereof sufficient to allow hybridization. In another embodiment, the antisense nucleic acid is wholly or partially complementary to and can hybridize with a target nucleic acid which encodes human alanyl-tRNA synthetase.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of human alanyl-tRNA synthetase, for example, antigenic function (e.g., binding of antibodies that also bind to non-recombinant human alanyl-tRNA synthetase), catalytic activity (e.g., catalysis of aminoacyl-adenylate formation, catalysis of aminoacylation of a tRNA with amino acid), binding function (e.g., tRNA-, amino acid-, or ATP-binding) and/or oligomerization activity.

As such, these proteins are referred to as alanyl-tRNA synthetases of human origin or human alanyl-tRNA synthetases, and include, for example, naturally occurring human alanyl-tRNA synthetases, variants (e.g. mutants) of those proteins and/or portions thereof. Such variants include mutants differing by the addition, deletion or substitution of one or more amino acid residues, or modified polypeptides in which one or more residues is modified, and mutants comprising one or more modified residues.

In a particularly preferred embodiment, like naturally occurring human alanyl-tRNA synthetases, isolated and/or recombinant human alanyl-tRNA synthetases of the present invention aminoacylate the isoaccepting cognate tRNAs of humans with alanine in a two-step reaction. In the first step, the alanyl-tRNA synthetase catalyzes the covalent linkage of alanine to ATP to form an aminoacyl-adenylate complex (alanyl-adenylate) with the release of pyrophosphate. In a second step, the alanyl-tRNA synthetase catalyzes the covalent linkage of alanine to a specific tRNA recognized by the enzyme, releasing AMP.

The invention further relates to fusion proteins, comprising a human alanyl-tRNA synthetase (as described above) as a first moiety, linked to a second moiety not occurring in the enzyme as found in nature. Thus, the second moiety can be a single amino acid, peptide or polypeptide. The first moiety can be in an N-terminal location, C-terminal location or internal to the fusion protein. In one embodiment, the fusion protein comprises a human alanyl-tRNA synthetase as the first moiety, and a second moiety comprising a linker sequence and affinity ligand.

Fusion proteins can be produced by a variety of methods. For example, some embodiments can be produced by the insertion of a human alanyl-tRNA synthetase gene or portion thereof into a suitable expression vector, such as Bluescript SK +/− (Stratagene), pGEX-5X-1 (Pharmacia) and pET-15b (Novagen). The resulting construct is then introduced into a suitable host cell for expression. Upon expression, fusion protein can be purified from a cell lysate by means of a suitable affinity matrix (see e.g., Current Protocols in Molecular Biology (Ausubel, F. M. et al., eds., Vol. 2, Suppl. 26, pp. 16.4.1–16.7.8 (1991)).

The invention also relates to isolated and/or recombinant portions of an alanyl-tRNA synthetase of human origin. Portions of the enzyme can be made which have full or partial function on their own, or which when mixed together (though fully, partially, or nonfunctional alone), spontaneously assemble with one or more other polypeptides to reconstitute a functional protein having at least one function characteristic of an alanyl-tRNA synthetase.

Deletion studies of the E. coli alanyl-tRNA synthetase (Jasin, M. et al., U.S. Pat. No. 4,952,501) showed that a large portion (over 400 C-terminal amino acid residues out of a protein 875 amino acid residues long) were unnecessary for specific aminoacylation activity. Large internal deletions also did not destroy enzymatic activity. Internal deletions within the N-terminal region of the alanyl-tRNA synthetase were able to complement a mutant monomeric polypeptide encoded by the alaS5 allele, possibly by the formation of hybrid quaternary structures in which activity of the N-terminal catalytic core is restored. Based on this type of analysis, portions of the human enzyme can be made which have at least one function characteristic of a human alanyl-tRNA synthetase, such as catalytic, binding function, antigenic function and/or oligomerization function. Studies on the structure and function of the aaRSs provide the basis for being able to divide the aaRS enzymes into functional domains (Schimmel, P., Current Biology 1:811–816 (1991)).

The tRNA synthetases can be subdivided into two groups of enzymes, class I and class II, based on short regions of sequence homology as well as distinct active site core tertiary structures (Eriani, G., et al., Nature 347:203–206 (1990); Moras, D., Trends Biochem. Sci. 17:159–164 (1992)). The primary sequence of the class II enzymes can be characterized by three motifs. These motifs are designated in the order they occur in the sequence as motif 1, motif 2, and motif 3. Although the motifs have a conserved core, they vary in length and are marked by as little as a single invariant amino acid residue. One way the motif sequences can be defined is as follows:

Motif 1: gΦxxΦxPΦΦ
Motif 2: (F/Y/H) Rx (E/D) (4–12x) (R/H) xxxFxxx (D/E)
Motif 3: λxΦgΦgΦeRΦΦΦΦΦ

The abbreviations are: x, variant; Φ, hydrophobic; and λ, small amino acids. Lower case letters indicate that the amino acid is partially conserved. None of these motifs are found in the class I family. With the exception of E. coli Gly- and Phe-tRNA synthetases which only contain a discernible motif 3, all class II enzymes incorporate all three motifs (Ribas de Pouplana, L. et al., Protein Science 2:2259–2262 (1993)). In the human alanyl-tRNA synthetase, by one interpretation, the three motifs are approximately as follows: motif 1 is at amino acid residues 7–30, motif 2 at amino acid residues 69–102 and motif 3 at amino acid residues 240–253.

The second class of tRNA synthetases was firmly defined when the crystal structure of the E. coli Ser-tRNA synthetase active site was shown to have no relationship to the Rossmann fold of class I enzymes (Cusack, S. C., et al., Nature 347:249–255 (1990)). X-ray diffraction investigations with an ATP-bound Ser-tRNA synthetase co-crystal from T. thermophilus revealed the details of a novel ATP binding site (Cusack, S., et al., In The Translational Apparatus, K. H. Nierhaus et al., eds., pp. 1–9, Plenum Press, New York, 1993); Belrhali, H., et al., Science 263:1432–1436 (1994); Biou, V., et al., Science 263:1404–1410 (1994)). The pocket is comprised of an eight-stranded anti-parallel β-sheet that is flanked by α-helices. An arginine residue at the N-terminal side of the loop of motif 2, and which is almost universally conserved among the class II tRNA synthetases, forms a salt bridge with the α-phosphate of ATP, while the adenine ring is stabilized by a stacking interaction with a phenylalanine in the second β-strand of motif 2. A well-conserved carboxyl side chain of glutamic acid in the loop of motif 2 interacts with the adenine ring through a hydrogen bond with N-6 and also via a water molecule with N-7.

Motif 3 is comprised of a β-strand followed by an α helix and is characterized by a GLER sequence. This motif is the only one that has been universally detected in all of the class II enzymes. The crystal structures of Ser- and Asp- (Ruff, M. S. et al., Science 252:1682–1689 (1991)) tRNA synthetases suggest a role for motif 3 in amino acid and ATP binding. Mutations in this region have resulted in a reduction in binding and/or a high $K_m$ for amino acid or ATP binding (Eriani, G., et al., Nature 347:203–206 (1993); Anselme, J. and Härtlein, M., FEBS Lett. 280:163–166 (1991); Kast, P. and Hennecke, H., J. Mol. Biol., 222:99–124 (1991); Kast, P. et al., FEBS Lett. 293:160–163 (1991); Lanker, S., et al., Cell 70:647–657 (1992)).

Yeast Asp-tRNA synthetase was the first class II enzyme to be co-crystallized with its cognate tRNA (Ruff, M., et al., Science 252:1682–1689 (1991)). The yeast Asp-tRNA synthetase contains a nucleotide binding structure similar to that found in Ser-tRNA synthetase. The combination of these two class II crystal structures provides a model for the active sites of all of the class II tRNA synthetases.

In the absence of a crystal structure for the class II E. coli Ala-tRNA synthetase, the conserved motifs, secondary structure predictions and biochemical crosslinking studies were used to model an active site similar to the structurally conserved catalytic cores of the known crystal structures for Ser- and Asp-tRNA synthetase (Ribas de Pouplana, L., et al., *Protein Science* 2:2259–2262 (1993)). These three class II enzymes contain little or no primary sequence homology other than in the highly degenerate motifs 1, 2, and 3. Because motif 1 is located at the dimer interface in the crystal structures of yeast Asp-tRNA synthetase (Ruff, M. S., et al., *Science* 252:1682–1689 (1991)) *E. coli* Ser-tRNA synthetase (Cusack, S., et al., *Nature* 347:249–255 (1990); Cusack, S., et al., In *The Translational Apparatus*, K. H. Nierhaus et al., eds., pp. 1–9, Plenum Press, New York, 1993); Price, S., et al., *FEBS Lett.* 324:167–170 (1993)), and *T. thermophilus* Ser-tRNA synthetase (Cusack, S., et al., In *The Translational Apparatus*, K. H. Nierhaus et al., eds., pp. 1–9, Plenum Press, New York, 1993); Belrhali, H., et al., *Science* 263:1432–1436 (1994); Biou, V., et al., *Science* 263:1404–1410 (1994)), motif 1 was thought to be important for dimerization. This motif was identified in the N-terminal region of *E. coli* Ala-tRNA synthetase (Ribas de Pouplana, et al., *Protein Science* 2:2259–2262 (1993)), but a series of deletion mutations had also previously demonstrated that a region at the C-terminus of the protein is needed for oligomerization (Jasin, M., et al., *Nature* 306:441–447 (1983); Jasin, et al., *Cell* 36:1089–1095 (1984)). Thus, motif 1 is not sufficient for oligomerization of this enzyme. An analysis of motif 1 in yeast Asp-tRNA synthetase also questions the role of motif 1 in oligomerization (Eriani, et al., *Proc. Natl. Acad. Sci., USA* 90:10816–10820 (1993)).

An idiographic representation of the predicted eight-stranded β-structure with three α-helices of the *E. coli* Ala-tRNA synthetase has been constructed (Ribas de Pouplana, L., et al., *Protein Science* 2:2259–2262 (1993)); Shi, J. -P., et al., *Biochemistry* 33:5312–5318 (1994)). Collectively, over 40 mutations in motif 2 and the region between motif 2 and 3 were individually constructed and tested (Davis, M. W., et al., *Biochemistry* 33:9904–9911 (1994); Shi, J. -P., et al., *Biochemistry* 33:5312–5318 (1994)). These mutations were mostly at conserved residues with chemical functional groups. Although motif 2 is of a different size and has only two identical amino acid residues with its counterpart in yeast Asp- and *T. thermophilus* Ser-tRNA synthetases, the mutational analysis of this motif can be explained in terms of those structures, and shows the importance of predicted motif 2 for adenylate synthesis (Ribas de Pouplana, L., et al., *Protein Science* 2:2259–2262 (1993)). A study of the products of random mutagenesis of this region also demonstrated the importance of motif 2 for adenylate transfer (Lu, Y. and Hill, K. A. W., *J. Biol. Chem.* 269:12137–12141 (1994)). Mutagenesis of specific residues in motif 2 of *E. coli* Ala-tRNA synthetase and mutagenesis of their predicted counterparts in motif 2 of yeast Asp-tRNA synthetase yielded similar results with regard to loss of function (Cavarelli, J., et al., *EMBO J.* 13:327–337 (1994); Davis, M. W., et al., *Biochemistry* 33:9904–9911 (1994). Evidence was obtained for a role for sequence context in determining how the energy of adenylate binding is partitioned between ground and transition states in the two enzymes. In addition, a conserved aspartate residue among Ala-tRNA synthetases at the beginning of motif 3 was shown to be important for the adenylate synthesis and particularly for the adenylate transfer reaction (Davis, M. W., et al., *Biochemistry* 33:9904–9911 (1994)). The functional significance of motif 3 for adenylate synthesis has been demonstrated by mutagenesis in the yeast Asp-tRNA synthetase system (Cavarelli, J., et al., *EMBO J.* 13:327–337 (1994)).

Method of Producing Recombinant aaRSs

Another aspect of the invention relates to a method of producing human alanyl-tRNA synthetase or a portion thereof and to expression systems and host cells containing a vector appropriate for expression of the human alanyl-tRNA synthetase.

Cells that express a recombinant aminoacyl-tRNA synthetase or a portion thereof can be made and grown in culture to produce the enzyme for isolation and purification. These cells can be procaryotic or eucaryotic. Examples of procaryotic cells that can be used to express human alanyl-tRNA synthetase include *Escherichia coli*, *Bacillus subtilis* and other bacteria. Examples of eucaryotic cells that can be used to express the human alanyl-tRNA synthetase include yeasts such as *Saccharomyces cerevisiae* and *Pichia pastoris*, and other lower eucaryotic cells, and cells of higher eucaryotes such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a recombinant human alanyl-tRNA synthetase protein or portion thereof for isolation and purification, as a first step the gene encoding the enzyme can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for human alanyl-tRNA synthetase, and has the coding sequence under the control of transcription signals and linked to appropriate translation signals to permit translation of the aaRS, portion thereof, or of a fusion protein comprising aaRS or portion thereof. As a second step, the vector can then be introduced into cells by a method appropriate to the type of host cells (e.g., transformation, electroporation, infection). In a third step, for expression from the aaRS gene, the host cells can be maintained under appropriate conditions, e.g., in the presence of inducer, normal growth conditions, etc.).

As a particular example of the above approach to producing active human alanyl-tRNA synthetase, a gene encoding human alanyl-tRNA synthetase can be integrated into the genome of a virus that enters the host cells. By infection of the host cells, the components of a system which permits the transcription and translation of the human alanyl-tRNA synthetase gene are present in the host cells. Alternatively, an RNA polymerase gene, inducer, or other component required to complete such a gene expression system may be introduced into the host cells already containing the human alanyl-tRNA synthetase gene, for example, by means of a virus that enters the host cells and contains the required component. The alanyl-tRNA synthetase gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Applications for Human Alanyl-tRNA Synthetase Protein

Antibodies directed to human aminoacyl-tRNA synthetases have been found in sera from patients with connective tissue disease, especially patients with idiopathic inflammatory myopathies, diseases such as polymyositis and dermatomyositis, characterized by elevated levels of muscle enzymes and by muscle weakness and wasting. In patients producing these antibodies, there is a significantly higher frequency of intersitial lung disease than in myositis patients not producing these antibodies (Targoff, I. N. and Arnett, F. C., Am. J. Med. 88:241–251 (1990)).

Different groups of patients have been studied who make antibodies that bind to alanyl-, histidyl-, threonyl-, glycyl-, or isoleucyl-tRNA synthetase (Targoff, I. N. et al., J. Clin. Invest. 91:2556–2564 (1993)). Alanyl-tRNA synthetase, along with histidyl-, threonyl-, and glycyl-tRNA synthetases, exist free in the cytoplasm of human cells tested. In contrast, isoleucyl-tRNA synthetase is a component of a stable, multi-enzyme complex containing at least seven tRNA synthetases (Mirande, M. et al., Prog. Nucleic Acid Res. Mol. Biol. 40:95–142 (1991)).

The etiology of the diseases associated with autoantibodies to tRNA synthetases is not understood. One hypothesis postulates that binding of the tRNA synthetase to infecting viral RNA enhances the immunogenicity of the synthetase, when the complex is released from cells damaged in viral infection (Mathews, M. B. and Bernstein, R. M. Nature 304:177–179 (1983)). This is in agreement with some studies supporting the theory that the target auto-antigen itself initiates, selects and sustains autoantibody synthesis (Miller, F. W. et al., Proc. Natl. Acad. Sci. USA 87:9933–9937 (1990)). An alternative hypothesis for the etiology of autoimmune disorders in general is that immunogenic components of pathogenic organisms, especially parasitic organisms, elicit the production of antibodies that cross-react with similar components of the host (See, for example, Meilof, J. F. et al., J. Immunol. 151:5800–5809 "Autoimmunity and Filariasis: Autoantibodies Against Cytoplasmic Cellular Proteins in Sera of Patients with Onchocerciasis" (1993)).

Isolated (e.g., purified), recombinant human alanyl-tRNA synthetase can be used in methods to detect anti-alanyl-tRNA synthetase antibodies in samples from patients who show the symptoms associated with the autoimmune diseases of antisynthetase syndrome. These methods can be useful not only to diagnose disease, but also to follow the severity of myositis disease activity.

Such methods of detecting anti-alanyl-tRNA synthetase antibodies can include biochemical assays. For instance, a sample (e.g. serum) obtained from a patient can be tested for an inhibitory effect on isolated, recombinant human alanyl-tRNA synthetase in a suitable assay, (e.g., aminoacylation assay, assay for aminoacyl-adenylate formation).

Such methods of detecting and monitoring disease can also include immunological methods such as immunodiffusion, enzyme-linked immunosorbent assay (ELISA), radioimmunoassay (RIA), Western blot, counter-immunoelectrophoresis, various antibody capture assays, immunodiffusion, particularly Ouchterlony double immunodiffusion, or various combinations of these methods and detection systems (See, e.g., for standard methods: Antibodies: A Laboratory Manual Harlow, E. and Lane, D., Cold Spring Harbor Laboratory Press, Cold Spring Harbor, N.Y., 1988).

For example, an antibody capture assay involves binding purified or partially purified AlaRS protein directly to a solid substrate, such as a microtiter plate. Alternatively, the AlaRs protein can be bound to the solid substrate indirectly, for example through antibodies that have been made specifically to AlaRS, in a two-antibody assay. Sites on the bound AlaRS protein that bind other proteins nonspecifically are saturated using a blocking buffer, typically containing bovine serum albumin. Excess blocking buffer is removed by one or more washing steps. The sample (e.g., serum) or dilution thereof to be tested for the presence of anti-AlaRS antibodies is added and maintained under conditions suitable for binding to the AlaRS protein. Unbound antibodies and other components of the serum are removed by one or more washes. Bound antibodies can be detected using a variety of methods. For example, a labeled secondary reagent, such as enzymatically labeled or radioactively labeled anti-immunoglobulin antibodies or protein A can be used to detect bound antibody. Excess labeled secondary reagent is removed by one or more washes.

An ELISA method can be used to screen the sera of patients having symptoms of autoimmune and/or neuromuscular disease for the presence of antibodies to human alanyl-tRNA synthetase (see Biswas, T. et al., J. Immunol. Methods 98:243–248 (1987) for an example of a method to detect anti-Jo-1 antibodies to human histidyl-tRNA synthetase). For the ELISA, recombinant human alanyl-tRNA synthetase can be isolated and purifed from host cells. The purified enzyme can be used to coat microtiter plates, and goat serum can be added to block non-specific binding sites on the enzyme. Diluted patient serum can then be added to the wells. Dilute peroxidase-conjugated goat IgG F(ab')$_2$ anti-human IgG, and in a subsequent step, peroxidase substrate can be added to the wells to enable quantitation of bound antibody by reading the light absorbance at 492 nm.

The isolation of the human alanyl-tRNA synthetase gene makes possible the production of relatively large amounts of this enzyme in pure form, compared to amounts of the enzyme that can be produced from human cells or cell lines. Co-purification of a host enzyme with the human enzyme is less likely when the human enzyme is expressed in a host organism not closely related to humans (Pichia pastoris, for instance, as demonstrated in examples herein). A further advantage of being able to efficiently produce the human alanyl-tRNA synthetase in cells contructed for the production of this foreign protein is that a radioactive label can be incorporated into the human AlaRS protein during the growth of the cells in culture, facilitating various assays such as immunological assays, and the quantitation and location of the human alanyl-tRNA synthetase.

Antibodies

The invention further relates to antibodies that bind to an isolated and/or recombinant human alanyl-tRNA synthetase, including portions thereof (e.g., a peptide), which can specifically recognize and bind to the enzyme. These can be used in methods to purify the protein or portion thereof by various methods of immunoaffinity chromatography, or to selectively inactivate one of the enzyme's active sites, or to study other aspects of the enzyme's structure, for example. The antibodies can be used to map the antigenic determinants on human alanyl-tRNA synthetase to which anti-alanyl tRNA synthetase autoantibodies react. They can also be used as control antibodies in assays to detect and quantitiate anti-alanyl-tRNA synthetase antibodies present in the body fluids of patients with certain idiopathic inflammatory myopathies, such as myositis, polymyositis and dermatomyositis. The antibodies may also be useful to detect the presence of human alanyl-tRNA synthetase in serum or other tissue samples, as a measure of cell damage.

The antibodies of the present invention can be polyclonal or monoclonal, and the term antibody is intended to encompass both polyclonal (e.g., raised in a suitable animal other than a human) and monoclonal antibodies. Antibodies of the present invention can be raised against an appropriate immunogen, including proteins or polypeptides of the present invention, such as an isolated and/or recombinant human alanyl-tRNA synthetase or a portion thereof, or synthetic molecules, such as synthetic peptides.

The term antibody is also intended to encompass single chain antibodies, chimeric, humanized or primatized (CDR-grafted) antibodies, as well as chimeric or CDR-grafted single chain antibodies, comprising portions derived from more than one species. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology,* 10: 1455–1460 (1992), regarding primatized antibody, and Ladner et al., U.S. Pat. No. 4,946,778 and Bird, R. E. et al., *Science,* 242:423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. For example, antibody fragments capable of binding to human alanyl-tRNA synthetase or a portion thereof, including, but not limited to, Fv, Fab, Fab' and F(ab')$_2$ fragments are encompassed by the invention. Such fragments can be produced, for example, by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons have been introduced upstream of the natural stop site. For example, a chimeric gene encoding an F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler et al., *Nature,* 256:495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); Current Protocols In *Molecular Biology,* Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably obtained from the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Anti-idiotypic antibodies can also be made. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880. Such antibodies can be useful in the suppression of the antibody response in patients who produce anti-alanyl-tRNA synthetase antibodies, for instance.

Assays for Inhibitors and Tester Strains

The enzymatic assays, binding assays, and construction of tester strains described below, can be used, alone or in combination with each other or other suitable methods, to identify inhibitors of one or more aminoacyl-tRNA synthetases of an organism of interest, such as a pathogenic organism. Such inhibitors can be tested further for the specific inhibition of a particular aminoacyl-tRNA synthetase of a particular pathogen. The inhibitors can be further tested for their possible effects on a specific aminoacyl-tRNA synthetase of humans or of other animals in which the inhibitor might be used as an antimicrobial agent.

Pathogenic organisms are characterized by their ability to cause an undesired infection in a human or animal, and are not limited to those organisms known to cause a characterized or named disease or condition. Pathogens include, for example, *Mycobacterium tuberculosis, Pneumocystis carinii, Candida albicans, Staphylococcus aureus,* and *Helicobacter pylori.*

Enzyme Assay

Upon the isolation of an aaRS gene from a pathogenic organism, the gene can then be incorporated into an expression system for production, followed by isolation and testing of the enzyme in vitro. The isolated or purified pathogen aaRS can also be used in further structural studies that will allow for the design of antibiotics which specifically target the aaRS of the pathogen, while not affecting or minimally affecting the mammalian (e.g., human) aaRSs. The design of these drugs will exploit the structural differences between the pathogen aaRS and the aaRSs of mammals, such as humans.

In a similar manner, an isolated human aminoacyl-tRNA synthetase gene can be incorporated into an expression system for production of the enzyme and subsequent testing of the enzyme in vitro. Information from assays and structural studies of the purified human enzyme, combined with information from assays and structural studies of the corresponding (i.e., specific for the same amino acid) pathogen enzyme intended as the target of an inhibitor, can be used to model inhibitors of the pathogen that will minimally affect the human enzyme.

Furthermore, isolated, active aaRSs of pathogens (or, of humans or other mammals as controls) can be used in an in vitro method of screening for inhibitors of aminoacyl-tRNA synthetase activity in which the inhibitory effect of a compound is assessed by monitoring, for example, AlaRS activity according to standard techniques. For example, inhibitors of isolated, active AlaRS of a pathogenic microbe can be identified by the method. By monitoring the effect of such inhibitors on isolated, recombinant human AlaRS, compounds which preferentially inhibit pathogen synthetase activity can be identified. In one embodiment, the isolated enzyme is maintained under conditions suitable for alanyl-adenylate formation, the enzyme is contacted with a compound to be tested, and formation of the aminoacyl-adenylate is monitored by standard assay. A reduction in the activity measured in the presence of compound, as compared with the activity in the absence of compound, is indicative of inhibition of AlaRS activity by the compound. In another embodiment, formation of alanyl-tRNA$^{Ala}$ is monitored in a standard aminoacylation assay. Inhibitors identified by enzymatic assay can be further assessed for antimicrobial activity using tester strains as described herein, or using other suitable assays.

Tester Strains

A substance to be used as a therapeutic agent preferably inhibits a pathogen aaRS without significantly inhibiting the corresponding aaRS of its host, e.g., a human or animal. Nucleic acids of the present invention can be used in constructing tester strains for in vivo assays of the effect on the activity of the pathogen enzyme of a substance which is added to tester strain cells. Complementation of a particular defective host cell aaRS gene by an aaRS gene of origin in a different species from the host cell aaRS gene is a threshold requirement for a tester strain.

A first type of tester strain comprises a host cell having a defect in an endogenous gene encoding an aaRS, and a heterologous pathogen aaRS gene which complements the defect in the host cell gene.

A second type of tester strain serves as a control for the first type of tester strain. This second type of tester strain also comprises a host cell having a defect in an endogenous gene encoding an aaRS, and also carries a heterologous gene encoding an aaRS, wherein the heterologous gene complements the defect in the host cell gene. However, in this case, the heterologous gene has its origin in a human or other animal, for example an animal that can be infected by the pathogen whose aaRS is tested in the first type of tester strain. Alternatively, the heterologous gene can be from a different animal species whose aaRS is closely related in structure to the aaRS of the susceptible animal (or human). This second type of tester strain allows the assessment of an inhibitory or toxic effect of a substance administered to the tester strain cells, due specifically to the interaction of the substance with the heterologous aaRS.

Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

For example, temperature-sensitive alleles of the genes encoding cytoplasmic IleRS and MetRS have been described in *S. cerevisiae* (Hartwell, L. H., and McLaughlin, C. S., *J. Bacteriol.* 96:1664–1671 (1968)), and are available from the Yeast Genetic Stock Center (University of California-Berkeley; catalog nos. 341 and 19:3:4, respectively). Temperature-sensitive serS strains of *E. coli* have also been described (Low, B., et al., *J. Bacteriol.* 108:742–750 (1971); Clarke, S. J. et al., *J. Bacteriol.* 113:1096–1103 (1973)).

Temperature-sensitive alaS strains of *E. coli* have been described (Buckel, P. et al, *J. Bacteriol.* 108:1008–1016 (1971); Lee, A. L. and Beckwith, J., *J. Bacteriol.* 166:878–883 (1986)), in addition to a number of strains with well-characterized alaS deletions and complementing alaS alleles on plasmids (Jasin, M., et al., *Cell* 36:1089–1095 (1984); Jasin, M. and Schimmel, P., *J. Bacteriol.* 159:783–786 (1984)). Such strains can be used as starting materials to construct *E. coli* tester strains for alanyl-tRNA synthetase genes of various organisms.

If the heterologous gene complements the inactivated host cell gene, such a cell can be used in a test of whether a substance can interact specifically with the pathogen tRNA synthetase (or a component in the pathway of tRNA synthetase gene expression) introduced for testing, to cause loss of function of the tested pathogen tRNA synthetase in those host cells. Thus, such cells are "tester strains." Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)). Cross-species complementation within the genus of the pathogen can also serve as the basis for testing in some cases.

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain comprises a host cell comprising a heterologous aaRS gene (that is, one from a heterologous or foreign species, specifically from a pathogen in the case of the first type of tester strain, and from a human or animal typically infected by the pathogen, in the case of the second type of tester strain), a suitable host cell is heterologous with respect to the species from which the gene to be tested is isolated. It will be understood that similar methods of strain construction can be used to produce a first type of tester strain (for specifically testing the sensitivity of a pathogen aaRS to a potential inhibitor of the aaRS activity) and to produce a second type of tester strain (for use as a control to evaluate the potential inhbitor of the pathogen aaRS for its specific effect on the corresponding human or animal aaRS of similar aminoacylation activity).

Species which are suitable for use as hosts for the construction of tester strains are *E. coli, S. cerevisiae,* and *B. subtilis,* for example. These species are especially amenable to genetic manipulation because of their history of extensive study.

Suitable host cells having a genotype useful for the construction of a tester strain can be constructed or selected using known methods. For example, both in *E. coli* and in *S. cerevisiae,* a first plasmid which contains a functional copy of a host chromosomal aaRS gene which is to be inactivated later, along with some selectable marker gene, can be constructed and introduced into cells. Then, an inactivating mutation can be caused in the chromosomal copy of the aaRS gene. One way to do this is by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel, P., *J. Biol. Chem.* 261(15):6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS. A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid (5-FOA) to select against S. cerevisiae cells which have a first plasmid containing the URA3 gene), cells which survive by virtue of having a complementing aaRS gene on the second plasmid can be selected (Sikorsky, R. S. and Boeke, J. D., Methods in Enzymology 194:302–318 (1991)).

A number of E. coli strains already exist in which an aaRS gene has been inactivated by some method, in whole or in part, yielding an observable phenotypic defect which can be detectably complemented. For example, null strains in which the gene encoding MetRS has been inactivated, and a mutant strain of E. coli in which the gene encoding MetRS has been conditionally inactivated, have been described (see Kim, et al., Proc. Natl. Acad. Sci. USA 90:10046–10050 (1993), describing a metG null strain of E. coli carrying a maintenance plasmid, MN9261/pRMS615); and Barker, D. G. et al. Eur. J. Biochem. 127:449–457 (1982) and Starzyk, R. M. et al., Biochemistry, 28:8479–8484 (1989), regarding a mutant strain having a methionine auxotrophy because the $K_m$ for methionine of the enzyme encoded by the chromosomal metG allele is elevated). A null strain in which the gene encoding AlaRS has been inactivated has been described (see Jasin, M. et al., Cell 36:1089–1095 (1984), for an alaS null strain of E. coli bearing a maintenance plasmid with alaS). Additional E. coli strains having a defect, such as a null mutation, in the alanyl-tRNA synthetase gene can be constructed in a similar manner using the E. coli alanyl-tRNA synthetase gene, which has been cloned and sequenced (Jasin, M. and Schimmel, P. J. Bacteriol. 152:783–786 (1984); Putney, S. D., et al., J. Biol. Chem. 265:20898–20906 (1990)).

Causing or selecting for a double crossover event which creates a deletion and insertion can be used in itself as a one-step method of constructing a tester strain in which a native aaRS gene is replaced by the corresponding gene whose gene product is to be tested. Endogenous recombination mechanisms have been used to advantage previously in E. coli, B. subtilis, and S. cerevisiae, among other organisms. This method depends on the ability of the heterologous (i.e., pathogen or human, for example) gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain, useful for testing the effect of a compound on the function of AlaRS expressed by an inserted heterologous gene, can be constructed in a one-step method. Optional positive and negative controls for this cross-species transformation can be used to show that the resulting strain depends on the AlaRS gene from the heterologous source for growth and that this recombination event is not lethal. For example, B. subtilis cells made competent for transformation (Dubnau, D. and Davidoff-Abelson, R., J. Mol. Biol. 56:206–221 (1971)) can be transformed with a suitable construct, such as a linearized plasmid containing an insert. Generally, the construct includes a selectable marker gene for antibiotic resistance, or some other suitable selectable marker. In one embodiment, a linearized plasmid which contains the heterologous AlaRS gene and an antibiotic resistance gene, situated between sequences homologous to the flanking sequences of the endogenous AlaRS gene of the host cells, is used to transform the host cell. For a positive control, the linearized plasmid can be constructed in a similar fashion, except that the native B. subtilis AlaRS gene replaces the heterologous gene, such that a normal B. subtilis AlaRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous AlaRS gene. Successful construction of a tester strain can also be confirmed by Southern analysis.

The yeast S. cerevisiae offers additional possibilities for genetic manipulations to create tester strains, relative to bacteria. For example, one-step gene disruptions can be performed in diploid cells using a yeast integrating plasmid or DNA fragment comprising a copy of an aaRS gene containing an insertion of a selectable marker in the aaRS gene. Optionally, a fragment comprising a copy of an aaRS gene containing a deletion and an insertion of a selectable marker can be constructed. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which also provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions. (See Examples 12 and 13 herein for specific examples of the construction of S. cerevisiae host strains carrying an ala1Δ::TRP1 disruption and bearing the maintenance plamsid pA38 which carries ALA1 and URA3. The host strains in Examples 12 and 13 can be transformed with a test plasmid bearing an alanyl-tRNA synthetase gene such as a human AlaRS gene to obtain a tester strain (Example 13)).

To construct a maintenance plasmid or a test plasmid carrying a heterologous gene, a suitable vector, such as a yeast centromere plasmid (CEN; single-copy) or 2μ vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2μ plasmids differing in the selectable marker (HIS3, TRP1, LEU2, URA3); see Christianson, T. W., et al., Gene, 110:119–122 (1992) regarding 2μ vectors; see Sikorski, R. S. and Hieter, P. Genetics, 122:19–27 (1989) regarding integrating and CEN plasmids which are available from Stratagene, La Jolla)) and shuttle vectors (integrating, CEN or 2μ vectors) which contain the multiple cloning site of pUC19 (Gietz, R. D. and Sugino, A., Gene, 74:527–534 (1988)). Examples of expression vectors include pEG (Mitchell, D. A. et al., Yeast, 9:715–723 (1993)) and pDAD1 and pDAD2, which contain a GAL1 promoter (Davis, L. I. and Fink, G. R., Cell 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehyrogenase; Bennetzen, J. L. and Hall, B. D., J. Biol. Chem., 257:3026–3031 (1982)) can be used to express an inserted gene on glucose-containing media. For example plasmid pMC4 carries the ADH (alcohol dehydrogenase) promoter of S. cerevisiae and the coding sequence for cytochrome oxidase IV targeting signal peptide, downstream from the promoter (Hurt, E. C. et al., J. Biol. Chem. 262:1420–1424 (1987)). Derivatives of plasmid pMC4 can be made which lack the coding sequence for the targeting signal peptide (that directs proteins to mitochondria) downstream from the ADH promoter. Such derivatives of plasmid pMC4 allow a coding sequence inserted downstream from the ADH promoter to cause the biosynthesis of a protein directed to the cytoplasm (unless the inserted coding sequence carries its own mitochondrial targeting signal). These derivatives can be engineered by cloning fragments derived from pMC4 into the vectors listed above, for example.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho-. As a result, these strains are unable to grow on non-fermentable carbon sources even if a complementing gene is introduced into the strain. Therefore, a haploid strain having a defect in, for example, the yeast mitochondrial alanyl-tRNA synthetase gene (e.g., a gene disruption with a cosegregating selectable marker constructed as indicated above) can be crossed with a rho$^+$ strain having a wild-type mitochondrial alanyl-tRNA synthetase gene to restore the mitochondrial DNA. The resulting rho$^+$ diploid can then be transformed with a plasmid which encodes the wild-type yeast mitochondrial alanyl-tRNA synthetase (i.e., a maintenance plasmid) and a second selectable marker. Following sporulation, progeny spores which carry the defective mitochondrial AlaRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using heterologous aminoacyl-tRNA synthetase genes.

For instance, a plasmid encoding a heterologous alanyl-tRNA synthetase gene can be introduced into such a yeast strain on a second plasmid having a third selectable marker. As indicated above, the maintenance plasmid can be selected against (e.g., where the selectable marker is URA3, selection on growth medium containing 5-fluoroorotic acid leads to loss of the maintenance plasmid), and complementation by the heterologous gene can be monitored on a non-fermentable carbon source.

In another embodiment of tester strain construction, a mitochondrial alanyl-tRNA synthetase gene disruption with a cosegregating selectable marker can be constructed in a diploid rho$^+$ strain (see e.g., Edwards, H. and P. Schimmel, Cell 51:643–649 (1987) for an example of a mitochondrial tyrosyl-tRNA synthetase gene disruption). A plasmid encoding a heterologous alanyl-tRNA synthetase gene can be introduced on a plasmid having a second selectable marker. Sporulation of a resulting diploid yields two progeny spores carrying the yeast mitochondrial alanyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the heterologous gene on the introduced plasmid is indicated by growth on non-fermentable carbon sources of cells carrying the disrupted alanyl-tRNA synthetase gene.

In the case of a mitochondrial tester strain, a heterologous aminoacyl-tRNA synthetase can be imported into mitochondria to achieve complementation of the mitochondrial defect. When it is necessary to achieve import, or desirable to improve the efficiency of import of an aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the heterologous aminoacyl-tRNA synthetase by an appropriate gene fusion. In one embodiment in yeast, the heterologous aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., J. Biol. Chem., 263:13097 (1988)). Expression of the construct yields a fusion protein with an N-terminally located cytochrome oxidase IV targeting signal joined to the aaRS protein of the heterologous organism.

If the construction methods described here are not successful initially, one or more natural or synthetic tRNA gene(s) of an organism other than the host cell (e.g., procaryotic, such as a bacterial, or eukaryotic, such as a mammalian or fungal) can be introduced into the host cell to provide one or more cognate tRNAs for the pathogen aaRS (or, the case of the second type of tester strain, for the human or animal aaRS). The tRNA genes of many species have been cloned and sequenced (Steinberg, S., et al. "Compilation of tRNA sequences and sequences of tRNA genes", Nucleic Acids Res. 21:3011–3015 (1993)). A method for constructing a strain of Streptomyces lividans in which an essential tRNA gene has been inactivated in the chromosome, and the gene is instead maintained on a plasmid, has been described (Cohen, S. N., WO 94/08033 (1994)).

Use of Tester Strains

Tester strains can be made to isolate the effect of a substance on a particular aaRS in vivo. The tester strains are ordinarily of two types: the first, dependent upon a heterologous aaRS gene of origin from a pathogenic microbe; the second, dependent upon a heterologous aaRS gene of origin from a host (animal or human) for a pathogenic microbe. Usually, the first type of tester strain is used to test for a desirable inhibitory effect of an antimicrobial agent upon a pathogenic aaRS. The second type of tester strain is used to test for an undesirable inhibitory effect of an antimicrobial agent, specifically upon the corresponding aaRS of a species of potential recipient of the antimicrobial agent, or of a related animal. This second type of tester strain can be considered a type of control strain for the first type of tester strain (the first type is also referred to herein as a "pathogen tester" strain or cells).

To assess the inhibitory effect of a substance on a tester strain, the cells are maintained under conditions suitable for complementation of the host cell defect by the heterologous aaRS gene. These are conditons under which the tester strain depends on the function of the heterologous aaRS gene and its product (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired, using pathogen tester cells, that is, cells dependent upon the aaRS derived from a pathogenic organism. For example, a substance to be tested can be administered to pathogen tester cells maintained under assay conditions, and the viability or growth of the pathogen tester cells in the presence of the substance can be compared with that of pathogen tester cells maintained under the same conditions in the absence of the substance. If it is determined that the substance inhibits growth of the pathogen tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the pathogen tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous aaRS gene present in the tester strain (i.e., an aaRS gene from a different species, such as a procaryotic or eukaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, the strain used as a control (a second type of tester stain) can be a strain distinct from the pathogen tester strain, but is constructed in a manner which generally parallels that of the pathogen tester strain comprising the pathogen test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene", which, as indicated above, is an aaRS gene other than the test gene (i.e., an aaRS gene from a different species, such as a heterologous procaryotic or eukaryotic species). Furthermore, the control gene, which can be cytoplasmic or mitochondrial, encodes an aaRS specific for the same amino acid (e.g., an alanyl-tRNA synthetase) as the test gene (e.g., an alanyl-tRNA synthetase).

Preferably, the control gene is selected from a species which is a host for the pathogen from which the test gene is derived, permitting the identification of specific inhibitors which selectively inhibit the pathogen aaRS (e.g., a human control gene for an *H. pylori* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a rat or mouse control gene for a *P. carinii* test gene).

Typically, the control gene is a human gene and the second type of tester strain used as a control for the pathogen tester strain is a human tester strain. The term "human" is used below as an illustration of a second type of control strain.

For example, a strain isogenic with a pathogen tester strain except for the substitution of a human control gene, can serve as a control strain, called a human tester strain. Such a control strain can be constructed using the same methods and the same host cell used to construct the first type of tester strain, with the exception that a human control gene is introduced into the host cell in lieu of the pathogen aaRS gene present in the tester.

Under the conditions of this assay, growth or viability of the second type (e.g. human) tester strain is dependent upon the control aaRS gene, which complements the host cell aaRS defect in the second type of tester strain which is used as a control. Specific inhibition by a substance can be determined by comparing the viability or growth of the pathogen tester and second type of tester strain in the presence of the substance.

The use of a second type of tester strain as a control is particularly important for use in testing a substance intended for use as an antimicrobial agent. Where the antimicrobial agent is intended for use in humans, a human tester strain provides a method of determining the extent of any toxicity or inhibitory effect specifically caused by the interaction of the antimicrobial agent with the human aaRS. Pairs of pathogen and human tester strains constructed from the same parental strain may be particularly useful where it is desirable to test the specific effects of a substance on the in vivo activity of both the aaRSs heterologous to the parental strain, under similar conditions. An example of such a pair is a *S. cerevisiae* strain dependent upon the function of the cytoplasmic alanyl-tRNA synthetase of *Candida albicans* and a nearly isogenic *S. cerevisiae* strain dependent upon the function of the cytoplasmic alanyl-tRNA synthetase of humans.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an E. coli host is used to construct a pathogen tester strain comprising a pathogen test gene, an E. coli strain comprising a wild-type E. coli aaRS gene can be used as a comparison control strain. In another embodiment, "parental-type" cells (e.g., parent host cells or a similap strain) are used as comparison controls. For example, the parent host cells of the first type tester strain can serve as a comparison control strain for the first type tester strain. Where the first and second types of tester strains have the same parent, a single strain can be used as the comparison control strain for both first and second types of tester strains.

For example, a parent host cell from which the pathogen tester and control (second type tester, e.g. human) strains were both constructed (e.g., by inactivation and replacement of the wild type host aaRS gene) can be used as a comparison control strain. This comparison control strain contains a wild type version of the aaRS gene which is inactivated in the tester strains, and the viability or growth of this comparison control strain is dependent upon the wild type aaRS under the conditions of the assay. Specific inhibition of the heterologous pathogen aaRS enzyme encoded by the heterologous pathogen gene (or a step in the expression of the heterologous gene) is indicated if, after administering the substance to both types of tester strains, growth of the pathogen tester strain is reduced as compared with an appropriate comparison control strain, and growth of the control (or second type tester) strain is not reduced, or is relatively less reduced, as compared with its appropriate comparison control strain.

Applications in Biochemistry

The following applications for an alanyl-tRNA synthetase are appropriate for a human or a *Saccharomyces cerevisiae* enzyme.

The alanyl-tRNA synthetase or portions (e.g. stable subdomains) of the protein can be used in a method to separate alanine from a mixture of alanine and other compounds such as other amino acids, or to specifically isolate L-alanine from D-alanine. The alanyl-tRNA synthetase can be chemically attached to a solid support material packed in a column or other suitable container. Alternatively, a fusion protein such as a GST-Ala tRNA synthetase fusion can permit attachment to a suitable solid support which binds the GST (glutathione S-transferase) portion of the fusion protein. For example, a mixture of alanine and other compounds can be loaded onto the column under conditions in which alanine binds to alanyl-tRNA synthetase, while other compounds present in the mixture flow through the column. In a later step, alanine can be released from the enzyme by changing the conditions in the column, such as washing with a solution of high ionic strength to elute L-alanine, for example.

In a similar manner, the alanyl-tRNA synthetase can be used in a method to isolate tRNA that specifically recognizes the alanyl-tRNA synthetase.

The aminoacyl-tRNA synthetase can be used in the quantitative determination of an amino acid such as alanine by its conversion to alanyl hydroxamate. An example of an appropriate assay is illustrated by the following series of reactions.

alanine+ATP→alanine-AMP+PP$_i$ (in the presence of excess pyrophosphatase and ATP at pH 7.5, where pyrophosphatase catalyzes the conversion of the product inorganic pyrophospate (PP$_i$) to inorganic orthophospate (P$_i$); ATP is adenosine triphospate; AMP is adenosine monophosphate)

alanine-AMP+NH$_2$OH→alanine-NHOH+AMP (at pH 7.5)

alanine-NHOH+FeCl$_3$→colored complex (at acidic pH)

The resulting colored complex can be quantitated by spectrophotometric measurements of absorbance at 540 nm, and compared with a standard curve made using known concentrations of alanine. This assay is based on the reactions described by Stulberg and Novelli, *Methods in Enzymology* 5:703–707 (1962).

The alanyl-tRNA synthetase can also be used for the quantitative determination of ATP. In the presence of excess alanine, and in the presence of pyrophoqphatase to convert the product PP$_i$ to P$_i$, the ATP is quantitatively converted to AMP and inorganic pyrophosphate by the alanyl-tRNA synthetase. For example, alanine+ATP→alanine-AMP+PP$_i$ (in the presence of AlaRS)

PP$_i$+H$_2$O→2P$_i$ (in the presence of pyrophosphatase)

P$_i$ can be quantitated by reaction with molybdate, measuring the absorbance at 580 nm and comparing to a standard curve made using known quantities of orthophosphate.

Primary Structure and Domain Organization of Human Alanyl-tRNA Synthetase

Using multiple alignments of partial and complete sequences of alanyl-tRNA synthetases with the neural net-based secondary structure program of Rost and Sander (Rost, B., et al., *Nature* 360:540 (1992)), and additional information from the known structures of the class II yeast aspartyl-and *E. coli* seryl-tRNA synthetases (Ruff, M., et al., *Science* 252:1682–1689 (1991); Cusack, S. et al., *Nature* 347:249–255 (1990)), a model for the secondary structure of the class-defining domain of the *E. coli* enzyme (amino acid residues 1-249) has been developed previously (Ribas de Pouplana, L., et al., *Protein Sci.* 2:2259–2262 (1993); Shi, J. P., et al., *Biochemistry* 33:5312–5318 (1994)). The model has the eight-stranded anti-parallel β structure characteristic of class II enzymes, including motif 1 (helix-loop-strand), motif 2 (strand-loop-strand), and motif 3 (strand-helix). This model has been further tested and refined by partial sequence information on additional alanyl-tRNA synthetases and by the construction and analysis of mutant proteins with substitutions at more than 40 different positions (Shi, J. P., et al., *Biochemistry* 33:5312–5318 (1994); Davis, M. W., et al., *Biochemistry* 33:9904–9911 (1994)). This model, as well as additional information about the locations of critical parts of the *E. coli* enzyme obtained from an earlier deletion analysis (Jasin, M., et al., *Nature* 306:441–447 (1983); Regan, L., et al., *Science* 235:1651–1653 (1987)) were used in analyzing the human alanyl-tRNA synthetase primary structure (see Example 4).

The domain needed for adenylate synthesis (but lacking aminoacylation activity) in the *E. coli* protein extends from the N-terminus to T368 (Regan, L., et al., *Science*

235:1651–1653 (1987)), which corresponds to T385 of the human enzyme. Full aminoacylation activity of microhelix substrates for the *E. coli* enzyme is achieved with a fragment that extends to H461 and defines a catalytic domain essential for aminoacylation (Buechter, D. D., et al., *Biochemistry* 32:5267–5272 (1993); aligns with F499 of the human enzyme).

Although aminoacylation of microhelix substrates by *E. coli* alanyl-tRNA synthetase is unaffected by the removal of the entire portion C-terminal from L462 (corresponds to E500 of human protein; Buechter, D. D., et al., *Biochemistry* 32:5267–5272 (1993)), catalytic and binding activity with the full tRNA$^{Ala}$ substrate is diminished by the deletion (Ho, C., et al., *Science* 229:389–393 (1985); Regan, L., et al., *Science* 235:1651–1653 (1987)). The effect on binding activity appears specifically due to deletion of L462 to T698. This segment encompasses the locations of the G674D and G677D mutations of the *E. coli* enzyme that are responsible for the temperature-sensitive phenotype of the alaS4 and alaS5 mutant alleles, respectively. These mutant alleles encode enzymes which have a diminished $k_{cat}$ for aminoacylation, with little effect on $K_m$ for tRNA$^{Ala}$ (Jasin, M., et al., *J. Biol. Chem* 260:2226–2230 (1985)). Thus, this segment of the protein may be needed specifically for synthetase-tRNA interactions that stabilize the transition state for aminoacylation, in addition to binding interactions in the ground state, and these interactions may involve parts of the tRNA structure outside of the acceptor helix domain.

The present invention is more specifically illustrated in the following examples, which are not intended to be limiting in any way.

EXAMPLE 1

Isolation of Fragment of Human Alanyl-tRNA Synthetase by Cross-Species Polymerase Chain Reaction An alignment-guided cross-species PCR approach was used in this work. Primers for PCR were designed by inspection of a multiple alignment of the complete nucleotide coding sequences for *Escherichia coli* (Putney, S. D., et al., *Science* 213:1497–1501 (1981)) and *Bombyx mori* (Chang P. and Dignam, J. D., *J. Biol. Chem.* 265:20898–20906 (1990)) alanyl-tRNA synthetases, and the partial sequences of the N-terminal coding regions of *R. leguminosarum* and *R. meliloti* alanyl-tRNA synthetases (Selbitschka, W., et al., *Mol. Gen. Genet.* 229:86–95 (1991)). Two well-conserved regions among the four species start at codon 38 and 86, respectively, of the *E. coli* enzyme. These regions were chosen for designing the primers KY-23 (SEQ ID NO:5) (TTYRCIAAYGCIGGIATGAAYCARTTYAAR) and KY-25 (SEQ ID NO:6) (RTTICCCATCATYTCRAARAAIGTRTGRTG, where Y=pyrimidine, R=purine, and I=inosine). These primers were used for PCR amplification of cDNA prepared from human fetal fibroblast cell strain TIG-2 (Ohashi, M., et al., *Exp. Geront.* 15:121–133 (1980)). Reactions were run for 35 cycles with the Gene Machine II thermal controller (US Scientific Plastics, Ocala, Fla.), with 2 min at 94° C., 2 min at 55° C., and 3 min at 72° C. for each cycle. Amplified fragments of approximately 170 basepairs (bp) were then cloned into the SmaI site of phagemid pTZ19R. The resulting plasmids were transformed into *E. coli* strain MV1184 (ara Δ(lac-proAB) rpsL thi (φ80 lacZΔM15) Δ(srl-recA) ::306Tnl0(tet$^r$)). Sequence analysis of six cloned PCR products showed two distinct sequences (type A in four clones and type B in two clones) that were related to alanyl-tRNA synthetase by sequence homology.

EXAMPLE 2

Screening of Human cDNA Library

A cDNA plasmid (pSI4001; Shigesada, K. et al., *Gene* 53:163–172 (1987) library derived from the human T-cell line KUT-2 (Shiba, K., et al., *Proc. Natl. Acad. Sci. U.S.A.* 91:7435–7439 (1994)) was screened with an oligonucleotide (TCTCACCCCATGGCAAAGCTG) (SEQ ID NO:7) which is specific for the "type A" cloned PCR fragment. For this purpose, approximately 5×10$^5$ colonies were immobilized onto 25 nylon filters (Duralon-UV, 82 mm, Stratagene, La Jolla, Calif.) as described (Shiba, K., et al., *J. Biol. Chem.* 269:30049–30055 (1994)). These filters were first preincubated in 50 ml of 6X SSC (1X SSC is 0.15M NaCl, 15 mM sodium citrate, pH 7.0), 5X Denhardt's solution (1X Denhardt's solution is 0.02% weight/volume Ficoll 400, 0.02% polyvinylpyrrolidone, 0.02% highly purified bovine serum albumin), 20 mM NaH$_2$PO$_4$ and 500 μg/ml of denatured salmon sperm DNA (Sigma Chemical Co., St. Louis) at 42° C. for 2 h and then incubated with the radiolabeled (5×10$^8$ cpm) oligonucleotide probe (labeled with $^{32}$p using γ-[$^{32}$P]ATP (7000 Ci/mmol, ICN Biomedicals, Costa Mesa, Calif.) and the Megalabel Kit of Takara (Ohtsu)) in 50 ml of 6X SSC, 1% sodium dodecyl sulfate (SDS), 20 mM NaH$_2$PO$_4$ and 500 μg/ml of salmon sperm DNA at 42° C. for 16 h. Filters were washed twice in 6X SSC and 0.1% SDS at 56° C. for 15 min and autoradiographed by exposing them to Kodak AR film with a Lightning Plus intensifier screen (DuPont, Wilmington, Del.) at −80° C. Three positive clones were obtained, of which one had a ~3.3 kilobasepair (kb) insert and the other two had a ~1.5 kb insert. The plasmid designated pKS-AA1 containing the ~3.3 kb insert was characterized further.

EXAMPLE 3

DNA Sequencing

Plasmid pKS-AA1 was digested at the single MluI site within the vector, filled in to make blunt ends by treatment with Klenow fragment and the four dNTPs (Sambrook, J., et al., *Molecular Cloning: A Laboratory Manual*, 2nd Ed., Cold Spring Harbor Laboratory, Cold Spring Harbor, N.Y. (1989)), and then digested at the only EcoRI site in the vector. The ~3.4 kb insert released by these digestions was separated from the other DNA fragment by agarose gel electrophoresis, recovered from the agarose gel, and then cloned into the EcoRI and SmaI site of phagemid pBluescript KS(+) (Stratagene) to construct plasmid pKS-AA1-11. The EcoRI-NotI fragment (which includes the entire insert) of pKS-AA1-11 was then recloned into the EcoRI-NotI sites of pBluescript KS(−) to give plasmid pKS-AA1-12. The EcoRI-BamHI fragment from the pKS-AA1-12 was recloned into the EcoRI-BamHI sites of pTZ19R to give plasmid pKS-AA1-13. Plasmids pKS-AA1-11, -12 and -13 were transformed into *E. coli* strain MV1184. Plasmid pKS-AA1-12 (in *E. coli* MV1184) was deposited in accordance with the provisions of the Budapest Treaty at the American Type Culture Collection (ATCC), 12301 Parklawn Drive, Rockville, Md. 20852, U.S.A. on Dec. 4, 1996, and assigned Accession Number 98270. Unidirectional deletions were made from pKS-AA1-12 and pKS-AA1-13 by using the Kilo-Sequence deletion kit (Takara Shuzo, Ohtsu). Single-stranded DNA was obtained by superinfection with helper phage M13 K07 (Vieira, J., and Messing, J., In *Recombinant DNA Methodology*, Wu, R., et al., eds. pp. 225–233, Academic Press, San Diego, Calif. (1989)), and sequences were determined with the ALF automated DNA sequencer (Pharmacia, Piscataway, N.J.). The sequence of each strand was determined at least once.

The entire 3,344 nucleotide sequence (exclusive of the poly(A) segment) of the type A cDNA clone was determined SEQ ID NO:1). It codes for a 968 amino acid polypeptide (SEQ ID NO:2). The size of this coding sequence was similar to that of a single 3.5 kb transcript detected by Northern blot analysis with a type A-specific probe of poly(A)+ RNA resolved by agarose gel electrophoresis. The open reading frame starts at the first AUG codon which is at nucleotides 111–113 of the sequenced insert. The AUG-containing sequence of AagAUGG retains the "A" and "G" flanking nucleotides of Kozak's optimal translation initiation sequences of ACCAUGG (Kozak, M. *Cell* 44:283–292 (1986)). The N-terminal amino acid sequence of the translated open reading frame does not share features typically found at the N-terminus of nuclear encoded mammalian mitochondrial proteins (von Heijne, G., et al., *Eur. J. Biochem.* 180:535–545 (1989)), suggesting that the type A sequence lacks a mitochondrial targeting sequence and, therefore, corresponds to a cytoplasmic protein. The predicted translation product has a molecular weight of 106,734 which compares with a molecular weight (determined by SDS polyacrylamide gel electrophoresis) of the 110,000 Da antigen that reacts with the human PL-12 autoantibody directed specifically against human alanyl-tRNA synthetase (Bunn, C. C., et al., *J. Exp. Med.* 163:1281–1291 (1986)).

EXAMPLE 4

Analysis of Sequences

Multiple sequence alignments were performed with the PILEUP program of the Genetics Computer Group (Madison, Wis.) which made alignments based on the method of Needleman and Wunsch (Needleman, S. B., and Wunsch, C. D. *J. Mol. Biol.* 48:443–453 (1970)).

With an alignment of four sequences of alanyl-tRNA synthetase from *E. coli* (Putney, S. D., et al., *J. Biol. Chem.* 256:198–204 (1981)), A. thaliana (Mireau, H., et al., *EMBL* Z22673 (1993)), B. mori (Chang, P., et al., *J. Biol. Chem.* 265:20898–20906 (1990)), and *H. sapiens*, the average similarity at each position was calculated using the PLOT-SIMILARITY program of the Genetics Computer Group. The identity scores were computed by dividing the number of identical residues among all four sequences by the total length of the shortest sequence of the four in a given region, and the results were expressed as a percentage. Based on the identity scores, the core domain for adenylate synthesis, which encompasses motifs 1, 2 and 3, can be assigned to the region from amino acid residues 1 through ~385, and the catalytic domain can be assigned to the region from amino acid residues 1 through ~499 of the human enzyme. In the dispensable domain (approximately amino acid residues 500 through 968 of the human enzyme) the identity residue score was substantially lower. In the region of the human enzyme (approximately amino acid residues 753–894) which aligns with the oligomerization domain of *E. coli*, the identity residue score was 1%.

Comparison of the inferred amino acid sequence of ALA1 of *S. cerevisiae*, as obtained in Example 12, with proteins in current databases indicated homology to alanyl-tRNA synthetases including those of *E. coli* (Putney, S. D. et al., *Science* 213:1497–1501 (1981)), *B. mori* (Chang, P. K. and Dignam, J. D., *J. Biol. Chem.* 265:20989–20906 (1990)), and *Arabidopsis thaliana* (Mireau, H. et al., *EMBL* Z22673 (1993)). The yeast protein also shares homology with the human protein described herein. Alignment of the 958 amino acid polypeptide with *E. coli*, *B. mori* and human alanyl-tRNA synthetases indicates similarities among the proteins, particularly in the amino-terminal domain which contains the three conserved motifs of the active site domain. The yeast protein is 49.7% and 37.2% identical to the human and *E. coli* enzymes, respectively.

EXAMPLE 5

Expression of Human Alanyl-tRNA Synthetase in *E. coli*

Modifications of cloning and expression vectors to make pKS315, pKS292 and pKS441 pKS315 was derived from pTZ19R (Mead et al., *Protein Engineering* 1:67 (1986); available from Sigma, St. Louis) by the insertion of a bovine-inositol monophosphatase-*E. coli* ileS fusion gene. pKS315 was used in this construction scheme because the insertion provided convenient restriction sites for further cloning into the vector.

pKS292 is a derivative of pET-3a (Studier, F. W., et al., In D. V. Goeddel (ed.), *Methods in Enzymology*, pp. 60–89 (1990); available from Novagen, Madison, Wis.) containing *E. coli* suhB (inserted in the opposite orientation for expression from the T7 promoter; see *J. Bacteriol.* 177:200–205 (1995) for suhB) which was constructed to be able to use the convenient restriction sites within the plasmid for cloning.

The 250 bp EcoRI-XhoI fragment from the multiple cloning site of pSL1190 (Pharmacia, Uppsala) was cloned into the EcoRI and XhoI sites of pGEX-5X-1 (Pharmacia) to construct pKS441.

Construction of pKS443 pKS441 was digested with BamHI and the ends were filled in with Klenow fragment. This DNA was further digested with StuI and the resulting blunt ends at the BamHI and StuI sites were self-ligated to construct pKS443. Both the BamHI and StuI sites were within the multiple cloning site originally from pSL1190. pKS443 has the NdeI site at the GST fusion point (GST is glutathione S-transferase of *Schistosoma japonicum*; the gene encoding GST is derived from pGEX-5X-1).

Construction of pKS370 and pKS382 pKS-AA1-12 (See Example 2) was mutagenized with oligonucleotide KIYO-79 (TTTGGGGTGACTTTCCATATGGACTCTACTCTAAC-AG) (SEQ ID NO:8) to create an NdeI site at the first in-frame ATG of the open reading frame. The resulting plasmid was designated pKS364.

Figure 8:
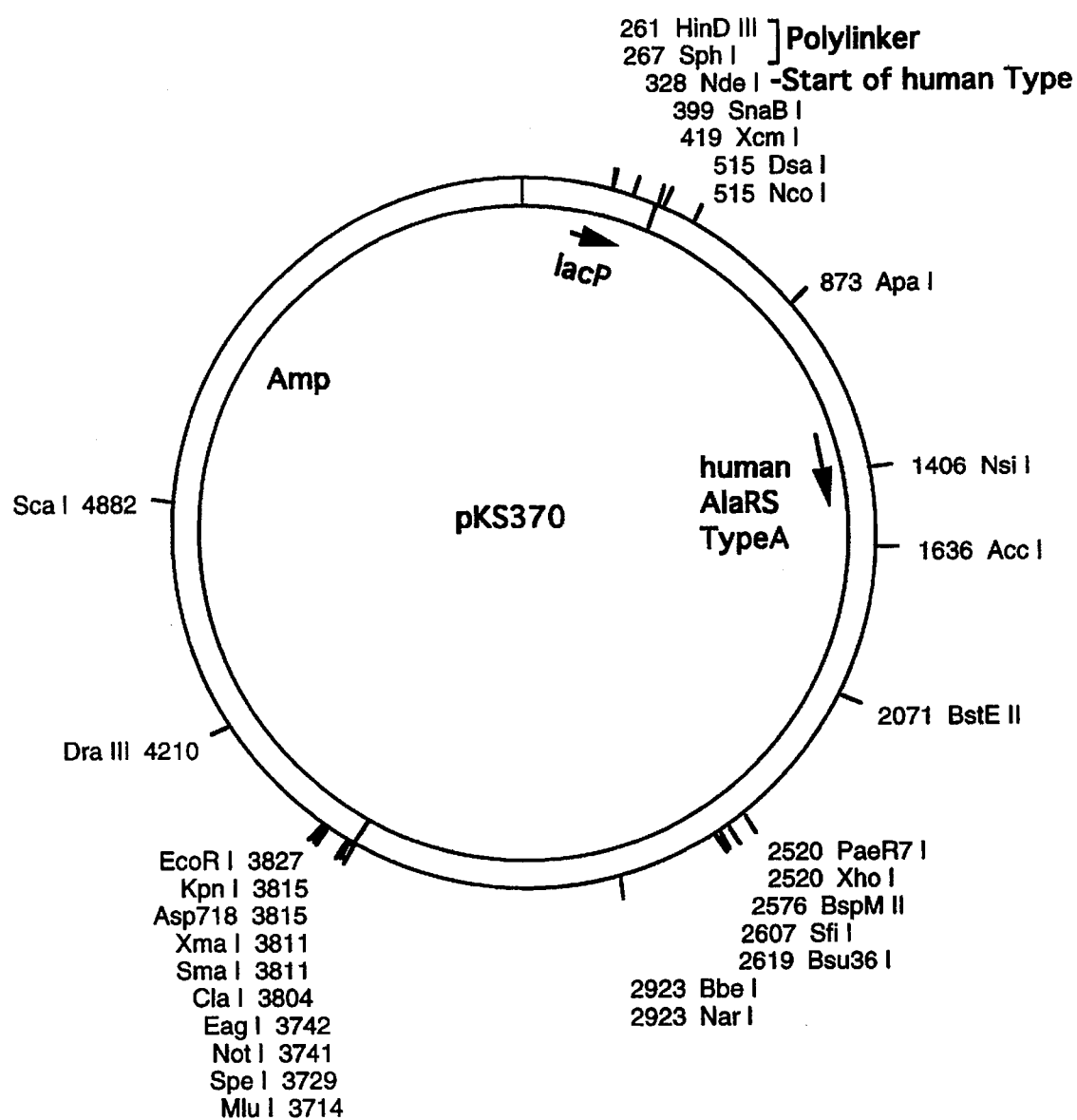
FIG. 8 is a map of the 6378 basepair plasmid pKS370.

The NdeI-NotI fragment of pKS364 was cloned into the NdeI-NotI sites of pKS315 to construct pKS370. Thus, pKS370 is a derivative of pTZ19R in which the human alanyl-tRNA synthetase gene is under the control of the lac promoter (FIG. 8).

The NdeI-Asp718 fragment from pKS370 was cloned into the NdeI-Asp718 sites of pKS292 to construct pKS382.

Construction of pKS446

The NdeI-NotI fragment of pKS370 was cloned into the NdeI and NotI sites of pKS441. The resulting plasmid, pKS446, encodes a GST-AlaRS fusion protein under the control of the lac promoter.

Preparation of E. coli Cell Extracts Containing
Human alanyl-tRNA Synthetase pKS370 and pKS446 were each transformed into JM109. (JM109 is [F'traD36, proAB, lacI$^q$ZΔM15] e14-(mcrA), recA1, endA1, gyrA96, thi-1, hsdR17 ($r_{k-}m_{k+}$), supE44, relA1, Δ(lac-proAB); available from Stratagene, La Jolla.) Cells were then grown at 37° C. in LB (10 g tryptone, 5 g yeast extract and 10 g NaCl/liter) containing 40 µg/ml ampicillin, to a density of $7 \times 10^7$ to $1 \times 10^8$ cells/ml before adding IPTG to 0.5 mM. After further growth at 37° C. for the cells were harvested by low speed centrifugation.

For the preparation of the GST-AlaRS fusion protein resulting from the induction of JM109 cells containing pKS446, the protocol described by Smith and Johnson (Gene 67:31–40, 1988) was followed. After harvesting, cells were resuspended in 1/50 to 1/100 the volume of the culture in 150 mMNaCl, 16 mM $Na_2HPO_4$, 4 mM $NaH_2PO_4$. Triton X-100 detergent was added to 1% vol/vol, and the cells were lysed by mild sonication. The lysate was centrifuged at 10,000×g for 5 min at 4° C. Analysis of the supernatant and pellet by staining and by Western blot using PL-12 antibodies (see Example 14) showed that virtually all of the fusion protein remained in the pellet.

To purify the protein resulting from the induction of JM109 cells containing pKS370, the low-speed cell pellets were stored overnight at −20° C., then lysed in a French press at 10,000 psi. The rest of the purification is as given in Example 8 after the lysis step. Proteins were analyzed by SDS polyacrylamide gel electrophoresis on an 8% polyacrylamide gel (See Sambrook, J., et al., *Molecular Cloning: A Laboratory Manual*, 2nd Ed., Cold Spring Harbor Laboratory, Cold Spring Harbor, N.Y. (1989) for procedures on SDS-PAGE.). The sample and stacking gel contained Tris-HCl (pH 6.8), the running buffer contained Tris-glycine (pH 8.3) and the resolving gel contained Tris-HCl (pH 8.8).

Expression Results

The recombinant human enzyme was successfully expressed in E. coli from pKS370, pKS382 and pKS446, as seen by bands of the appropriate molecular weight on an SDS-polyacrylamide gel (initially, from expression of the gene in the pET-3a derivative pKS382). However, no aminoacylation activity for the protein expressed in E. coil could be detected in cell extracts.

The three plasmids containing the human alanyl-tRNA synthetase gene were also tested for complementation of alaS in E. coli, using a strain of E. coli containing a null mutation in alaS on the chromosome and a maintenance plasmid carrying alaS on a plasmid that is temperature-sensitive for replication (Jasin, M. et al., *Cell* 36:1089–1095 (1984)). None of the plasmids were able to complement the defect in alaS.

EXAMPLE 6

Construction of a *Pichia pastoris* Strain for
Expression of Human alanyl-tRNA Synthetase An NdeI site was incorporated at the first ATG codon (nucleotides 111–113) of the coding sequence of the human cDNA using the Oligonucleotide-Directed In Vitro Mutagenesis System Kit (Amersham, Buckinghamshire). The NdeI-NotI fragment was made blunt-ended by treatment with Klenow fragment and the four dNTPs, and then ligated with an EcoRI linker oligonucleotide. The fragment was then cloned into the EcoRI site of the *Pichia pastoris* expression vector pHIL-D2, which has a HIS4 marker (Invitrogen), to give plasmid pKS491. This plasmid has the cDNA clone for human alanyl-tRNA synthetase under the control of the promoter of the gene for *P. pastoris* alcohol oxidase (AOX1). Five µg of pKS491 was linearized by digesting with NotI (which cleaves at sites within the vector) and was introduced into spheroplasts of strain GS115 (a HIS4 mutant of *Pichia pastoris*; available from Invitrogen). HIS$^+$ transformants were selected by growth for 4 days at 30° C. on plates containing 18.6% D-glucitol, 1.34% yeast nitrogen base without amino acids (Difco, Detroit, Mich.), 0.4 µg/ml D-biotin, 2% D-glucose and 50 µg/ml each of L-glutamic acid, L-methionine, L-lysine, L-leucine and L-isoleucine. Colonies which grew were checked for their utilization of methanol by scoring for growth on "MM" plates containing 1.34% yeast nitrogen base without amino acids, 0.4 µg/ml D-biotin (Sigma Chemical Co.) and 0.5% methanol and, separately, on "MD" plates containing 1.34% yeast nitrogen base without amino acids, 0.4 µg/ml D-biotin and 2% D-glucose. If the introduced DNA fragment becomes integrated into the AOX1 locus of the host chromosome by homologous recombination between the 5'- and 3'- AOX1 sequences in the pHIL-D2 vector portion of pKS491 and those in the genome, then the resultant cells are disrupted at the AOX1 gene and cannot metabolize methanol as the sole carbon source (Mut$^-$ phenotype). One of the His$^+$/Mut$^-$ transformants (that grow on MD plates but not on MM plates) was purified as the strain designated NOR-Aa6. The NOR-0 control strain was a His$^+$/Mut$^-$ transformant obtained by introduction of the vector pHIL-D2 without the cDNA insert encoding human alanyl-tRNA synthetase.

EXAMPLE 7

Expression of Human alanyl-tRNA Synthetase in *P. pastoris* and Preparation of Extracts for
Aminoacylation of Bovine and E. coil tRNA Strains NOR-Aa6 and NOR-0 were grown at 30° C. for 24 h in 5 ml of 1.34% yeast nitrogen base without amino acids, 0.4 µg/ml D-biotin and 1% glycerol. Cells were harvested and resuspended in 10 ml of MM medium and incubated for an additional 66 h at 30° C. The cells were then resuspended in 0.2 ml of 50 mM sodium phosphate (pH 7.4), 1 mM phenylmethylsulfonyl fluoride (Sigma Chemical Co.), 1 mM ethylenediaminetetraacetic acid (EDTA) and 5% glycerol, and broken with acid washed glass beads (425–600 microns (Sigma Chemical Co.)).

Aminoacylation activities of cell extracts were assayed as described (Shiba, K., et al., *J. Biol. Chem.* 267:22703–22706 (1992)) using 30 ng of crude extract (as determined by the Protein Assay Kit (BioRad, Richmond)), 120 µCi L-[3-$^3$H] -alanine (76.9 mCi/mmol (New England Nuclear, Boston) in a total reaction mixture of 100 µl containing 0.4 mg/ml of either E. coil MRE 600 or calf liver tRNA (Boehringer-Mannheim), 20 µM alanine, 0.1 mg/ml bovine serum albumin, 20 mM KCl, 10 mM $MgCl_2$, 20 mM β-mercaptoethanol, 4 mm ATP, and 50 mM sodium phosphate (pH 7.5).

Figure 2:
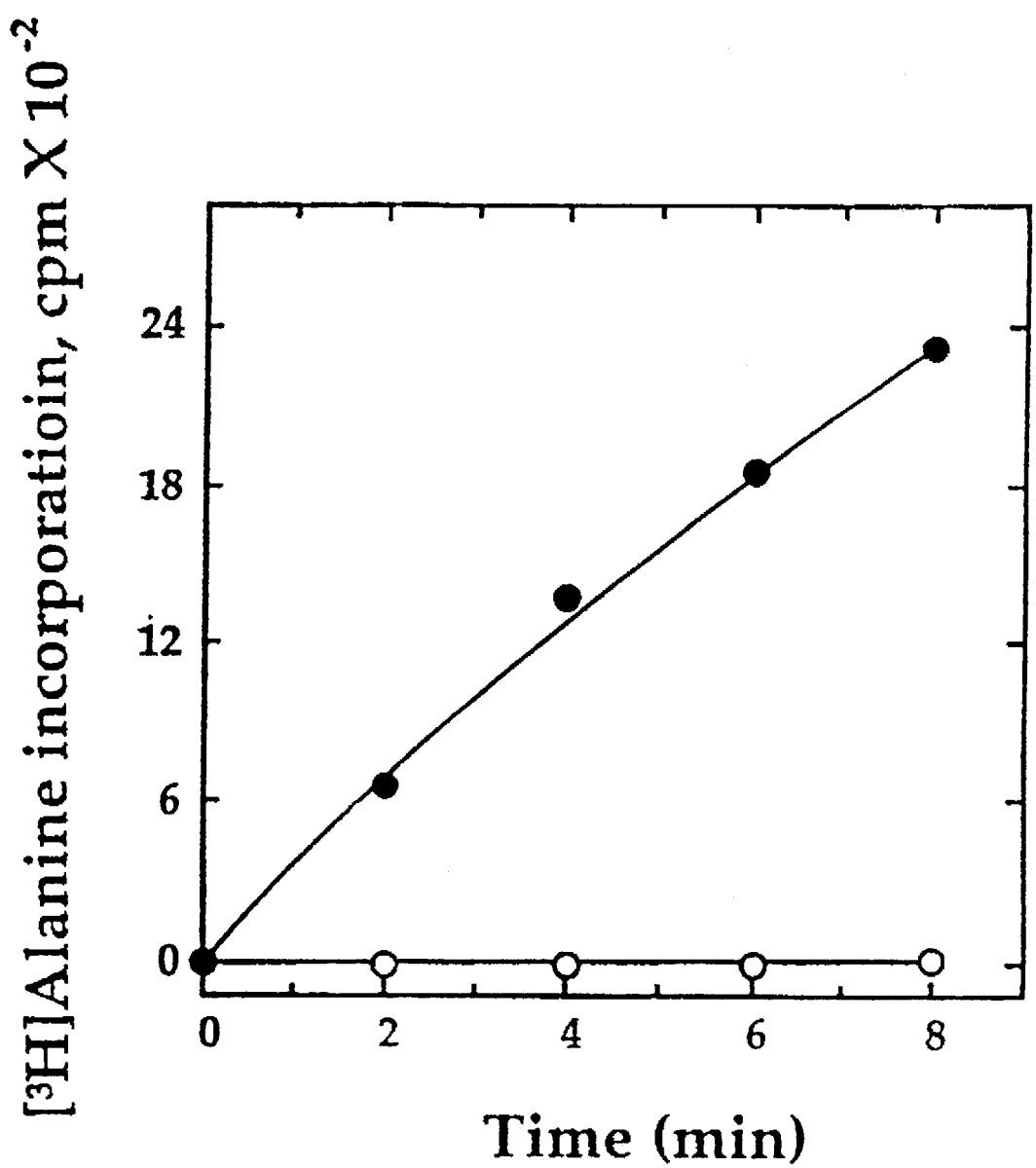
FIG. 2 is a graph showing the species specific aminoacylation of *E. coli* tRNA with [$^3$H]-alanine as a function of time, by an extract of *P. pastoris* strain NOR-Aa6 (closed circles), which carries the human alanyl-tRNA synthetase gene, or by an extract of *P. pastoris* strain NOR-0 (open circles), which is isogenic with NOR-Aa6, except that it does not carry the human alanyl-tRNA synthetase gene (Example 6).

After induction, extracts prepared from strain NOR-Aa6, but not from NOR-0, showed significant aminoacylation activity using [$^3$H]-alanine and bovine tRNA as substrate. The enzyme activity expressed in *P. pastoris* can cross-acylate E. coli tRNA as well as bovine tRNA (FIG. 1 and FIG. 2). These observations confirmed that the cloned human cDNA encoded an active enzyme.

EXAMPLE 8

Purification of Human Alanyl-tRNA Synthetase from *P. pastoris*

One liter cultures of strains NOR-Aa6 and NOR-0 were grown at 30° C. as described above. Cells were harvested and resuspended in 25 ml 40 mM Bis-Tris (bis[2-hydroxyethyl]iminotris[hydroxymethyl]methane; 2-bis[2-hydroxyethyl]amino-2-hydroxymethyl]-1,3-propanediol) (pH 7.5; Sigma Chemical Co.), 2 mM β-mercaptoethanol, 10% glycerol, 1 mM benzamidine (Sigma), 20 µg/ml leupeptin (Sigma), 25 µg/ml aprotinin (Sigma), 3.5 µg/ml pepstatin A (Sigma), and 1 mM phenylmethylsulfonyl fluoride (Sigma) and lysed in a French press (SLM Amnica) at 10,000 psi. Cell debris was removed by centrifugation at 35,000× g for 60 minutes and the suspension was applied to a 10 cm×2.5 cm DEAE-Superose column. The column was step eluted with 40 mM Bis-Tris (pH 7.5), 2 mM β-mercaptoethanol, 300 mM NaCl and 1 mM phenylmethylsulfonyl fluoride. The eluate was further fractionated on a Mono Q 10/10 (Pharmacia) column and eluted with a gradient of NaCl from 0 to 400 mM in 40 mM Bis-Tris (pH 7.5) and 2 mM β-mercaptoethanol. Enzyme activity from the NOR-Aa6 strain (but not from the "vector alone" control strain NOR-0) eluted at 220 mM NaCl. Peak fractions were pooled, concentrated and applied to a Superose 6 HR 10/30 (Pharmacia) column and eluted with 40 mM Bis-Tris (pH 7.5), 2 mM β-mercaptoethanol. The enzyme was estimated as 90% homogeneous by electrophoresis on an 8% polyacrylamide gel in the presence of 0.1% sodium dodecyl sulfate (SDS).

EXAMPLE 9

Determination of Molecular Weight of Human Alanyl-tRNA Synthetase

Figure 3:
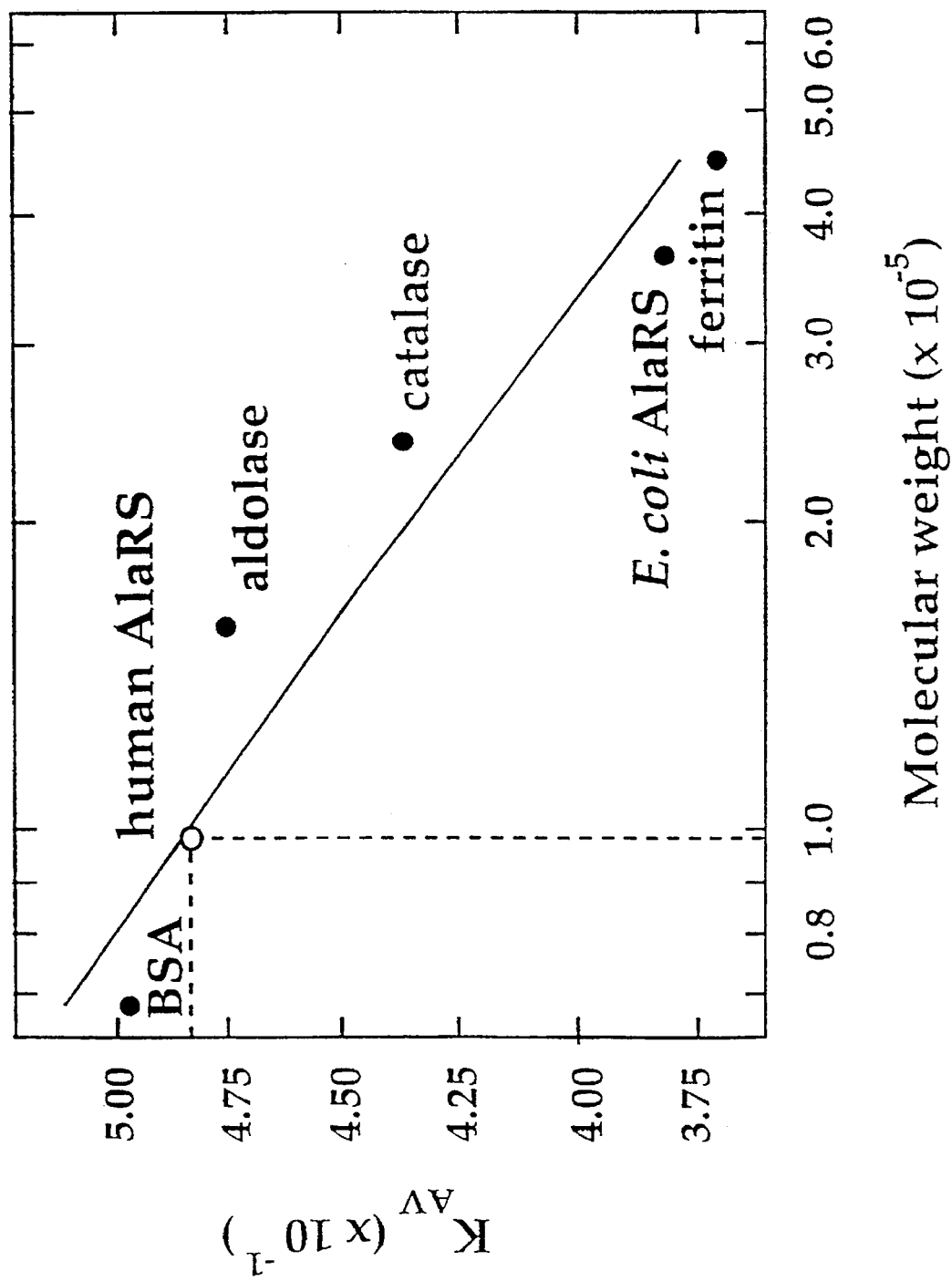
FIG. 3 is a graph illustrating the results of Superose 6 chromatography of native human alanyl-tRNA synthetase, *E. coli* alanyl-tRNA synthetase, and other proteins added as molecular weight standards (Example 9).

The molecular weight of human alanyl-tRNA synthetase was determined by Superose 6 chromatography (FIG. 3). A Superose 6 HR 10/30 (Pharmacia) column was equilibrated with 40 mM Bis-Tris (pH 7.5), 100 mM NaCl, 2 mM β-mercaptoethanol. All samples were applied in a volume of 0.1 ml. The column void volume was determined from the elution volume of blue dextran (average molecular weight 2,000,000 Da; Sigma Chemical Co.). The elution volumes of standard proteins were determined by separate chromatography of bovine serum albumin ($M_r$=67,000 Da), aldolase (158,000 Da), catalase (232,000 Da), *E. coli* alanyl-tRNA synthetase (380,000 Da), and ferritin (440,000 Da). Concentrations of proteins loaded onto the column were: ferritin (5 mg/ml), aldolase (5 mg/ml), catalase (5 mg/ml) and *E. coli* alanyl-tRNA synthetase (7 mg/ml). Elution positions of standards and *E. coli* and human alanyl-tRNA synthetases were determined by absorbance at 280 nm.

The data were analyzed in terms of $K_{av}$ values where $K_{av}=(V_e-V_o)/(V_t-V_o)$ and $V_e$, $V_o$ and $V_t$ are the elution, void, and column volume, respectively. From this analysis, a molecular weight of 98,000 Da was obtained. This compares with a value of 106,734 Da based on the amino acid sequence. The reasonable agreement of these values demonstrates that the human enzyme is active as a monomer.

EXAMPLE 10

Human Alanyl-tRNA Synthetase Aminoacylates Duplexes Based on *S. cerevisiae* Cytoplasmic tRNA$^{Ala}$ In Vitro The major determinant for aminoacylation with alanine of the *E. coli* tRNA$^{Ala}$ is a G3:U70 base pair (Hou, Y. -M. and Schimmel, P., *Nature* 333:140–145 (1989)) that is conserved in the alanine tRNAs of *S. cerevisiae* (Sprinzl, M. et al., *Nucleic Acids Res.* 17:r1-r172 (1989)). It was tested whether purified human alanyl-tRNA synthetase could cross-aminoacylate crude tRNA from Baker's yeast and a chemically synthesized 9-bp RNA duplex substrate based on the acceptor helix of yeast cytoplasmic tRNA$^{Ala}$. The ability of purified human alanyl-tRNA synthetase to aminoacylate duplex substrates was assayed using protocols described in Hill and Schimmel (*Biochem.* 28:2577–2586 (1989)). The RNA concentrations used were 5 µM for crude tRNA and 50 µM for the duplex substrates; the enzyme concentration was 200 nM. Chemical synthesis and purification of RNA duplexes were carried out as described previously (Usman, N. et al., *J. Am. Chem. Soc.* 109:7845–7854 (1987); Scaringe, S. A. et al., *Nucleic Acids Res.* 18:5433–5441 (1990); Musier-Forsyth, K. et al., *Proc. Natl. Acad. Sci. U.S.A.* 88:209–213 (1991)).

Figure 4:
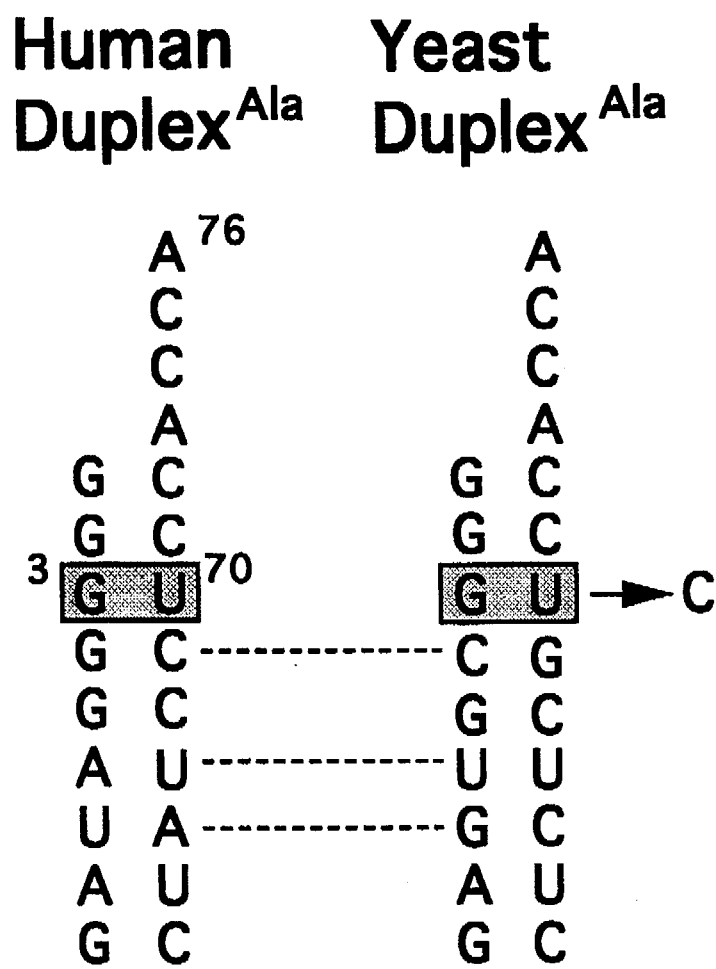
FIG. 4 is a diagram of RNA duplex substrates based on the acceptor stems of human cytoplasmic tRNA$^{Ala}$ or *S. cerevisiae* cytoplasmic tRNA$^{Ala}$ and the first two basepairs of the *E. coli* TψC-helical stem. The critical G3:U70 basepair is shaded and positions where substrates differ are indicated by dashed lines.
Figure 5:
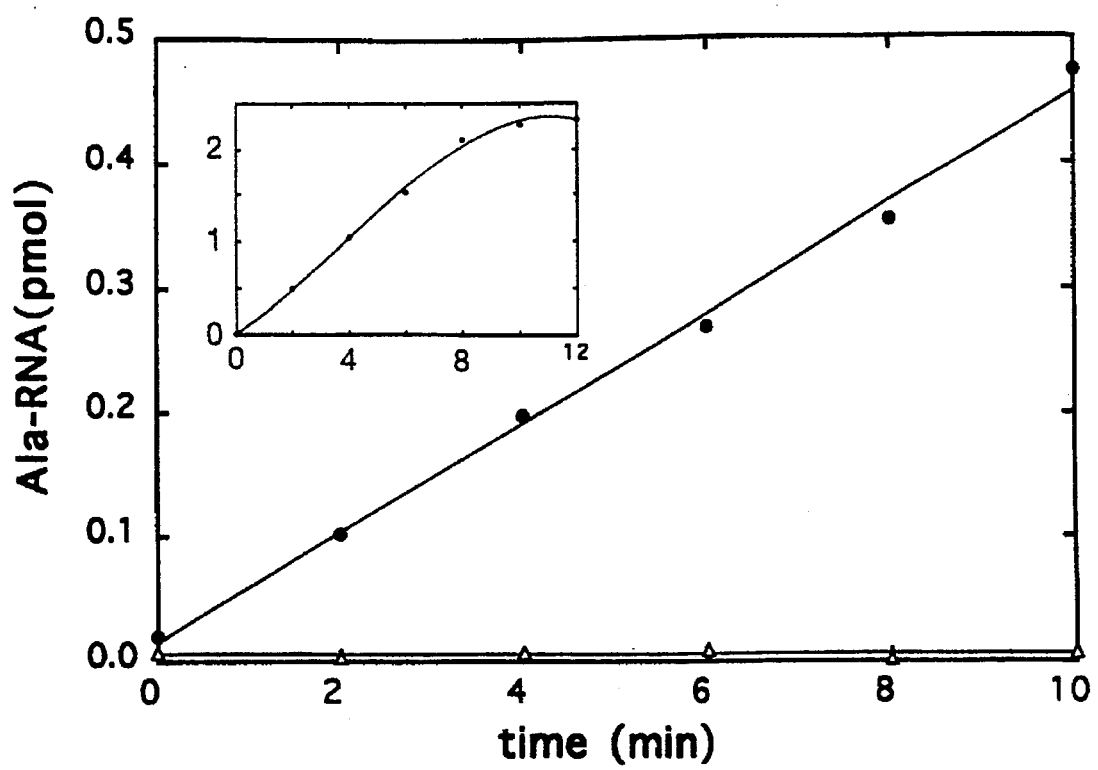
FIG. 5 is a graph showing the rates of aminoacylation of crude yeast tRNA and synthetic RNA duplexes by human alanyl-tRNA synthetase. Reactions were carried out with either crude Baker's yeast tRNA (inset), or the acceptor stems of *S. cerevisiae* cytoplasmic tRNA$^{Ala}$ containing either G3:U70 (closed circles) or G3:C70 (open diamonds). Enzyme concentrations were 200 nM. RNA concentrations were 5 μM for crude tRNA and 50 μM for the duplex substrates (see Example 10).

The recombinant human enzyme is able to aminoacylate crude *S. cerevisiae* tRNA as well as the "*S. cerevisiae*" RNA duplex (FIG. 4 and FIG. 5), indicating that the human enzyme can recognize the G3:U70 basepair in the context of a *S. cerevisiae* cytoplasmic alanyl-tRNA which differs from the human counterpart at positions 4:69, 6:67, and 7:66. A single U70 to C change eliminates aminoacylation of the "*S. cerevisiae*" duplex by the human enzyme.

EXAMPLE 11

Figure 7:
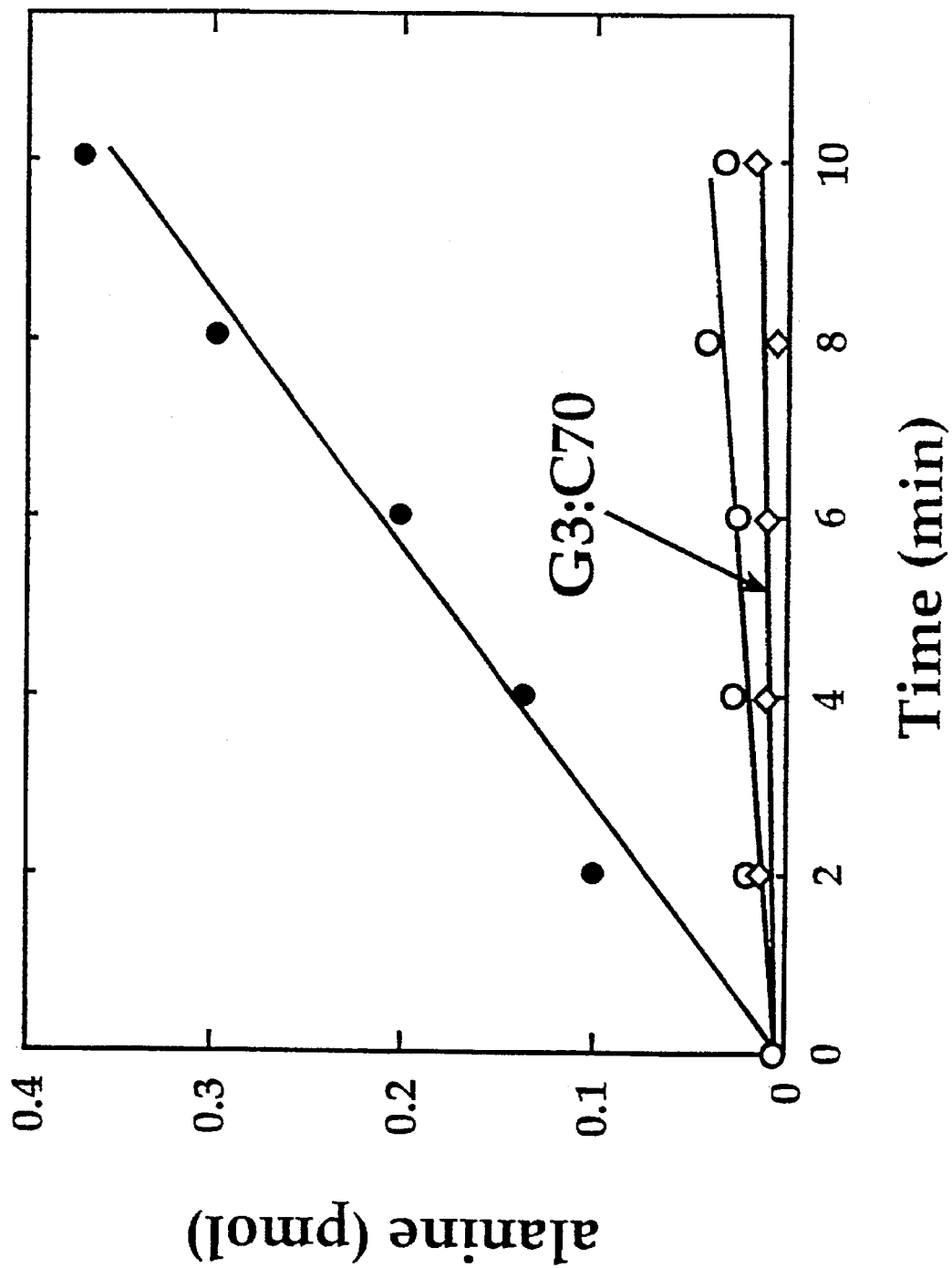
FIG. 7 is a graph of the results of an aminoacylation assay of synthetic RNA duplex substrates. The time course of aminoacylation by recombinant human alanyl-tRNA synthetase obtained by using duplex RNA whose sequence is based on the acceptor helix of human cytoplasmic tRNA$^{Ala}$ is represented by closed circles; the time course obtained by using a U70→C mutant human tRNA duplex as substrate is represented by open triangles. The time course of aminoacylation obtained by testing identical protein fractions prepared from non-recombinant *P. pastoris* on "wild type" duplex RNA as substrate is represented by open circles.

Human Enzyme Aminoacylates RNA Duplex Substrates Based on Acceptor Stems of Human or *E. coli* tRNA$^{Ala}$ RNA duplexes consisting of the first nine base pairs of the *E. coli* and human cytoplasmic tRNA$^{Ala}$ acceptor stems were chemically synthesized and purified as described previously (Putney, S. D., et al., *J. Biol. Chem.* 256:198–204 (1981); Usman, N., et al., *J. Am. Chem. Soc.* 109:7845–7854 (1987); Scaringe, S. A., et al., *Nucleic Acids Res.* 18:5433–5441 (1990); FIG. 6). Purified human enzyme was assayed for its ability to aminoacylate duplex substrates using protocols previously described (Musier-Forsyth, K. et al., *Proc. Natl. Acad. Sci. U.S.A.* 88:209–213 (1991); Schreier, A. A., et al., *Biochemistry* 14:1582–1589 (1972); Hill, K., et al., *Biochemistry* 28:2577–2586 (1989)). The assays were carried out at pH 7.5, 25° C. Enzyme concentrations were 300 nM and RNA concentrations were 50 µM. These duplexes share the critical G3:U70 base pair and differ in sequence at the 5:69, 6:68, and 7:67 positions of the acceptor stem. The recombinant human enzyme aminoacylates the "human" RNA duplex substrate and has no detectable activity on the G3:C70 variant substrate (FIG. 7). The recombinant human enzyme also cross-acylates the *E. coli* RNA duplex substrate. These results indicate that RNA duplex recognition and aminoacylation are conserved in the human alanine system. A fragment comprised of the first 461 amino acids of the *E. coli* enzyme has full activity for aminoacylation of model substrates based on acceptor stem sequences (Buechter, D. D., et al., *Biochemistry* 32:5267–5272 (1993)). Based on the results herein and the sequence analysis performed (Example 4), it can be concluded that the analogous N-terminal segment (N-terminal segment which extends to F499) of the human enzyme also contains determinants needed for RNA duplex aminoacylation.

EXAMPLE 12

Identification of the Essential S. cerevisiae Gene Encoding alanyl-tRNA Synthetase and Construction of ala1 Null Strain Recombinant DNA techniques, gel electrophoresis, Southern blotting, and hybridization of DNA were performed as described in Sambrook et al. (*Molecular Cloning: A Laboratory Manual*, 2d ed., Cold Spring Harbor Laboratory Press, (1989)). Qiabrane nylon membrane (Qiagen) was used for DNA blotting. Subclones designed to be used in both *E. coli* and yeast were inserted into the pRS series of vectors (Sikorski, R. S. and Hieter, P., *Genetics* 122:19–27 (1989)).

Degenerate oligonucleotides designed to hybridize to DNA encoding a conserved motif found in the N-terminal domain of alanyl-tRNA synthetases from *E. coli*, *B. mori*, *R. leguminosarum* and *R. meliloti* were used to amplify the corresponding sequence from total yeast genomic DNA from *S. cerevisiae* strain MM1401 (MATa/α, ade2-101/+, can1/+, his3Δ200/his3Δ200, leu2Δ1/leu2Δ1, lys2-801/lys2-801, trp1Δ101/trp1Δ101, ura3-52/ura3-52), obtained from John Woolford (Carnegie Mellon University, Pittsburgh). The primers used in the cross-species PCR method (Keng, T. et al., *J. Biol. Chem.* 254:12503–12508 (1982)) were KY-23 (TTYRCIAAYGCIGGIATGAAYCARTTYAAR) (SEQ ID NO:5) and KY-25 (RTTICCCATCATYTCRAARAAIGTRTGRTG) (SEQ ID NO:6), where Y=pyrimidine, R=purine, and I=inosine. Reaction conditions were as for the cloning of the human gene. PCR products were directly sequenced using Circum-Vent (New England Biolabs).

One amplified sequence was identified and shown to encode a peptide with similarity to alanyl-tRNA synthetase from *E. coli* and *B. mori*. A non-degenerate 59-mer oligonucleotide corresponding to a portion of the sequence of the amplified fragment was radioactively labeled and used to screen a library of yeast genomic DNA cloned in plasmid YCp50, an ARS1 replicon which contains the URA3 selectable marker (Rose, M. S. et al., *Gene* 60:237–243 (1987)). Plasmids recovered from four cross-hybridizing colonies were shown to have overlapping inserts by restriction endonuclease mapping, and PCR amplification and sequencing confirmed that these plasmids contained the region of interest. pA38 is a genomic clone isolated from the YCp50 library which was found to have a 6.8 kb insert of yeast genomic DNA which contains the full-length ALA1 gene. Southern blotting indicated that the 59-mer oligonucleotide PCR product hybridized to the 715-basepair (bp) XbaI-BglII fragment.

The full-length ALA1 gene was cloned into pRS315 (Sikorski, R. S. and Hieter, P., *Genetics* 122:19–27 (1989)) to make pTR94, or into pRS423 (Christianson, T. W., et al., *Gene* 110:119–122 (1992)) to make pTR84. Each plasmid contains a fragment of DNA starting from a PvuII site approximately 500 basepairs 5' of the translation start site of ALA1 to a XhoI site located about 1.0 kb downstream of the stop codon of ALA1. pTR94 and pTRydpw84 have been transformed into *E. coli* strain Tb-1 (K12, Δ(lac-proAB), supE, thi, hsdΔ5 F'[traD36, proAB⁺ lacI^q lacZΔM15]).

Plasmid pTR94 (in *E. coli* TG1) was deposited in accordance with the provisions of the Budapest Treaty at the American Type Culture Collection (ATCC), 12301 Parklawn Drive, Rockville, Md. 20852, U.S.A. on Dec. 4, 1996 and assigned Accession Number 98269.

Restriction fragments from ALA1 were subcloned in pBluescript KS(+) and SK(+) (Stratagene). The sequences of both strands of the ALA1 gene were determined by the dideoxy chain-termination method (Sanger, F. et al., *Proc. Natl. Acad. Sci. U.S.A.* 74:5463–5467 (1989)) using Sequenase Version 2.0 (United States Biochemical). Gaps of sequence in either strand were completed by using synthetic oligonucleotide primers synthesized by the Biopolymers Laboratory at Massachusetts Institute of Technology. The DNA sequence (GertBank Accession #U18672) is shown in SEQ ID NO:3.

An ala1 null allele was created by replacing the 510-bp BglII-SalI restriction fragment of ALA1 coding sequence with a BamHI-SalI fragment of the TRP1 gene. This TRP1 fragment can be obtained from plasmid YDpW (Berben, G. et al., *Yeast* 7:475–477 (1991)), or from pJJ281 (ATTC®No. 77307, available from American Type Culture Collection, 12301 Parklawn Drive, Rockville, Md. 20852-1776). Trp⁺ colonies were selected after transforming an XbaI-XhoI restriction fragment containing this ala1Δ::TRP1 disruption into MM1401, which is homozygous for trp1Δ101. The expected transplacement was confirmed by genomic Southern blotting. Diploids were sporulated, and dissection of 27 tetrads indicated only two spores were viable in each tetrad, both of which were Trp-. To verify that ALA1 is required for mitotic growth and not strictly spore germination, pA38 bearing ALA1 and URA3 was used to transform the ala1::TRP1/ALA1 diploid and the transformant was sporulated. Trp⁺ spores were recovered, all of which were Ura⁺, indicating that ALA1 is an essential gene.

With the exception of histidyl- and valyl-tRNA synthetases (Natsoulis, G. et al., *Cell* 46:235–243 (1986); Chatton, B. et al., *J. Biol. Chem.* 263:52–57 (1988)), the cytoplasmic and mitochondrial enzymes are encoded by separate nuclear genes in *S. cerevisiae*. Because the product of the ALA1 gene is essential for mitotic growth, it is probably cytoplasmic alanyl-tRNA synthetase. The gene for *S. cerevisiae* alanyl-tRNA synthetase was designated ALA1.

Southern blot analysis of the yeast genome indicated a second locus which cross hybridizes to DNA probes representing the 5' end of ALA1. This related locus may encode mitochondrial alanyl-tRNA synthetase.

EXAMPLE 13

Complementation of a Null Allele of ALA1 by Human Alanyl-tRNA Synthetase Gene in a S. cerevisiae Tester Strain To test whether the human enzyme could functionally complement a strain bearing an ala1-null allele, the coding sequence of human alanyl-tRNA synthetase was cloned into the BglII site of the 2μ plasmid pDB20LBglII (Berger, S. L. et al., *Cell* 70:251–265 (1992)) which contains the LEU2 gene as a selectable marker, creating plasmid pHsAlaRS. To make this plasmid, the NdeI-NotI fragment of pKS370 (Example 5) was filled in at the ends with Klenow fragment and the BglII site of pDB20LBglII was cut and filled in with Klenow fragment to make blunt ends to ligate together. The identically treated NdeI-NotI fragment from pKS370 was used to make a plasmid with the fragment inserted in the "antisense" orientation with respect to the strong constitutive alcohol dehydrogenase promoter ADH1.

After transformation of pHsAlaRS or the "antisense" plasmid into a haploid strain (MATα, ura3-52, leu2Δ1, lys2-801, trp1Δ101, ala1::TRP1) containing pA38 bearing ALA1 and URA3, Leu⁺ colonies were plated on medium containing 5-fluoroorotic acid (5-FOA) to select for loss of the URA3 plasmid (Boeke, J. D. et al., *Mol. Gen., Genet.* 197:345–356 (1984)).

The cells transformed with pHsAlaRS, but not the cells transformed with the "antisense" plasmid, were able to grow on 5-FOA. Colonies from the 5-FOA plate were subsequently confirmed to be Leu⁺Ura⁻ and to contain the ala1::TRP1 null allele. This result shows that human alanyl-tRNA synthetase can functionally replace the product of the ALA1 gene in yeast. Comparison of the growth rate (by colony size) of the haploid ala1 disruption strain (MATα, ura3-52, leu2Δ1, lys2-801, trp1Δ101, ala1::TRP1) containing ALA1 (on pA38) with the same haploid ala1 disruption strain containing the human alanyl-tRNA synthetase gene (on pHsAlaRS) indicates that the strain containing the human gene has a slight growth disadvantage. The ability of human alanyl-tRNA synthetase to complement a null allele of the yeast gene indicates the specificity of the human enzyme for yeast tRNA$^{Ala}$, and also indicates that little if any non-specific aminoacylation by the human enzyme is occurring.

EXAMPLE 14

Immunoblot Analysis

Protein extracts were prepared from haploid ala1 disruption strains (MATα, ura3-52, leu2Δ1, lys2-801, trp1Δ101, ala1::TRP1) carrying a YCp50 plasmid with AlA1 and URA3, and also carrying pDB20LBglII, or pDB20LBglII with the human alanyl-tRNA synthetase gene inserted in the 'antisense' orientation as controls, or pDB20LBglII with the human alanyl-tRNA synthetase gene inserted in the 'sense' orientation (pHsAlaRS; see Example 13).

Protein extracts were made by centrifuging 10 ml of logarithmic phase yeast cells and resuspending them in 1 ml of lysis buffer (100 Tris pH 8.0, 20% glycerol, 1 mM dithiothreitol, 1 mM phenylmethylsulfonyl fluoride). Glass beads were then added to ⅓ the total volume, and samples were vortexed 8 times for 15 seconds on ice in between each vortexing. Extracts were then allowed to settle for 5 minutes on ice. 5–15 μl samples were loaded onto SDS-polyacrylamide gels for electrophoresis.

Duplicate protein samples from yeast cell extracts were subjected to polyacrylamide gel electrophoresis and either stained with Coomassie blue or electrophoretically transferred to Immobilon membrane (Millipore) and assayed by immunoblot analysis with PL-12 antiserum (for methods, see Harlow, E. and Lane, D., "Immunoblotting" In *Antibodies: A Laboratory Manual*, pp. 471–504, Cold Spring Harbor Laboratory, 1988) using alkaline phosphatase conjugated anti-human antibodies (Promega, Madison, Wis.) and nitroblue tetrazolium chloride and 5-bromo-4-chloro-3-indolylphosphate p-toluidine salt from Gibco/BRL (Gaithersburg, Md.). PL-12 autoantibodies against human alanyl-tRNA synthetase (Bunn, C. C, and Mathews, M. B. *Science* 238:1116–1119 (1987)) were a generous gift of Michael Mathews (Cold Spring Harbor Laboratory, Cold Spring Harbor, N.Y.).

In the lane of the immunoblot in which the gel was loaded with protein extract from cells containing both the YCp50 maintenance plasmid and pDB20LBglII, one band was seen at a position corresponding to a molecular weight of about 46 kDa. In the lane of the immunoblot in which the gel was loaded with protein extract from cells containing both the YCp50 maintenance plasmid and pDB20LBglII with the NdeI-NotI fragment of the human alanyl-tRNA synthetase gene inserted in the "antisense" orientation, the same 46 kDa background yeast protein band was seen, as it was seen for all three protein samples. This protein is not yeast alanyl-tRNA synthetase, which has a predicted molecular weight of 106,245 Da. In the lane of the immunoblot in which the gel was loaded with protein extract from cells containing both the YCp50 maintenance plasmid and pDB20LBglII with the NdeI-NotI fragment of the human alanyl-tRNA synthetase gene inserted in the "sense" orientation (pHsAlaRS), a second band, human alanyl-tRNA synthetase, was seen at a position corresponding to a molecular weight of 100 kDa.

Because the PL-12 antibodies do not cross-react with yeast alanyl-tRNA synthetase, yeast strains expressing human alanyl-tRNA synthetase may be useful in understanding the epitopes that elicit an immune response and in the rational design of drugs that could inhibit autoantibody generation.

Equivalents

Those skilled in the art will know, or be able to ascertain using no more than routine experimentation, many equivalents to the specific embodiments of the invention described herein. These and all other equivalents are intended to be encompassed by the following claims.

---

What is claimed is:

1. An essentially pure nucleic acid which encodes a human alanyl-tRNA synthetase.

2. An essentially pure nucleic acid which codes for an active human alanyl-tRNA synthetase, and which hybridizes to DNA having SEQ ID NO:1 under moderate stringency conditions, wherein moderate stringency conditions comprise hybridization in 6X SSC, 1% sodium dodecyl sulfate, 20 mM $NaH_2PO_4$ and 500 µg/ml salmon sperm DNA at 42° C. for 16 hours and two washes in 6X SSC and 0.1% sodium dodecyl sulfate at 56° C. for 15 minutes.

3. An essentially pure nucleic acid which encodes an amino acid sequence SEQ ID NO:2.

4. An isolated nucleic acid comprising a nucleic acid having a sequence complementary to a DNA strand having a SEQ ID NO:1 or to an RNA counterpart of SEQ ID NO:1 or to a portion of said DNA or RNA counterpart comprising the coding sequence.

5. A recombinant nucleic acid vector comprising nucleic acid which encodes a human alanyl-tRNA synthetase and which hybridizes to DNA having SEQ ID NO:1 under moderate stringency conditions, wherein moderate stringency conditions comprise hybridization in 6X SSC, 1% sodium dodecyl sulfate, 20 mM $NaH_2PO_4$ and 500 µg/ml salmon sperm DNA at 42° C. for 16 hours and two washes in 6X SSC and 0.1% sodium dodecyl sulfate at 56° C. for 15 minutes.

6. A recombinant nucleic acid vector comprising DNA which encodes a human alanyl-tRNA synthetase.

7. A recombinant nucleic acid vector of claim 6 comprising DNA which codes for an amino acid sequence SEQ ID NO:2.

8. An expression vector comprising a nucleic acid encoding a fusion protein comprising a human alanyl-tRNA synthetase, wherein said nucleic acid comprises a coding sequence for a human alanyl-tRNA synthetase, and wherein the coding sequence is under control of transcription signals and is linked to appropriate translation signals for expression in a suitable host cell.

9. A host cell comprising a recombinant human alanyl-tRNA synthetase gene.

10. A method for producing active human alanyl-tRNA synthetase comprising the following steps:

a) constructing a recombinant nucleic acid vector comprising a coding sequence for human alanyl-tRNA synthetase, wherein the coding sequence is under the control of transcription signals and is linked to appropriate translation signals;

b) introducing the vector into suitable host cells which support replication of the vector;

c) maintaining the host cells under conditions in which the coding sequence for human alanyl-tRNA synthetase is expressed; and d) isolating human alanyl-tRNA synthetase from the host cells.

11. A method for producing isolated, recombinant human alanyl-tRNA synthetase comprising the following steps:

a) providing host cells comprising a recombinant gene encoding human alanyl-tRNA synthetase;

b) maintaining the host cells under conditions in which the gene encoding human alanyl-tRNA synthetase is expressed; and c) isolating human alanyl-tRNA synthetase from the host cells.

12. A host cell comprising a recombinant nucleic acid encoding a fusion protein comprising a human alanyl-tRNA synthetase.

13. A tester strain comprising host cells which comprise a recombinant human alanyl-tRNA synthetase gene which expresses a human alanyl-tRNA synthetase, wherein the recombinant, human alanyl-tRNA synthetase gene complements or substitutes in function for a host cell alanyl-tRNA synthetase gene.

14. The tester strain of claim 13 in which a host cell alanyl-tRNA synthetase gene has been lost or replaced or has been altered relative to wild type so as to make no gene product, a gene product which is inactive, or a gene product which can be conditionally made inactive, and in which the recombinant human alanyl-tRNA synthetase gene detectably complements the altered host cell gene.

15. The tester strain of claim 13 in which the host cells are bacterial cells.

16. The tester strain of claim 13 in which the host cells are yeast cells.

17. The tester strain of claim 16 in which the host cells are of the species *Saccharomyces cerevisiae* and in which the host cell alanyl-tRNA synthetase gene is ALA1.

18. An essentially pure nucleic acid which encodes a *Saccharomyces cerevisiae* alanyl-tRNA synthetase and which hybridizes to DNA having SEQ ID NO:3 under moderate stringency conditions, wherein moderate stringency conditions comprise hybridization in 6X SSC. 1% sodium dodecyl sulfate, 20 mM $NaH_2PO_4$ and 500 µg/ml salmon sperm pNA at 42° C. for 16 hours and two washes in 6X SSC and 0.1% sodium dodecyl sulfate at 56° C. for 15 minutes.

19. An essentially pure nucleic acid which encodes an alanyl-tRNA synthetase of *Saccharomyces cerevisiae* having the amino acid sequence in SEQ ID NO:4.

20. A recombinant nucleic acid vector comprising nucleic acid which encodes alanyl-tRNA synthetase of *Saccharomyces cerevisiae*.

21. A host cell comprising a recombinant *Saccharomyces cerevisiae* alanyl-tRNA synthetase gene which expresses a

*Saccharomyces cerevisiae* alanyl-tRNA synthetase or fusion protein which comprises a *Saccharomyces cerevisiae* alanyl-tRNA synthetase.

22. A host cell comprising a recombinant nucleic acid which encodes a human alanyl-tRNA synthetase and which hybridizes to DNA having SEQ ID NO:1 under moderate stringency conditions, wherein moderate stringency conditions comprise hybridization in 6X SSC, 1% sodium dodecyl sulfate, 20 mM $NaH_2PO_4$ and 500 µg/ml salmon sperm DNA at 42° C. for 16 hours and two washes in 6X SSC and 0.1% sodium dodecyl sulfate at 56° C. for 15 minutes.

23. An isolated nucleic acid, wherein said nucleic acid encodes a protein comprising an alanyl-tRNA synthetase which is encoded by pKS-AA1-12 as deposited under ATCC Accession No. 98270.

24. The isolated nucleic acid of claim 23, wherein the protein is a fusion protein.

25. The isolated nucleic acid of claim 24, which is essentially pure.

26. A host cell comprising a recombinant nucleic acid, wherein said nucleic acid encodes a protein comprising an alanyl-tRNA synthetase which is encoded by pKS-AA1-12 as deposited under ATCC Accession No. 98270.

27. A method for producing a protein comprising an alanyl-tRNA synthetase, comprising maintaining a host cell of claim 26 under conditions suitable for expression of said protein, whereby said protein is produced.

28. Plasmid pKS-AA1-12, from host cells deposited under ATCC Accession No. 98270.

29. An isolated nucleic acid, Wherein said nucleic acid encodes a protein comprising an alanyl-tRNA synthetase which is encoded by pTR94 as deposited under ATCC Accession No. 98269.

30. The isolated nucleic acid of claim 29, which is essentially pure.

31. A recombinant nucleic acid vector comprising nucleic acid encoding a protein comprising an alanyl-tRNA synthetase which is encoded by pTR94 as deposited under ATCC Accession No. 98269.

32. A host cell comprising a recombinant nucleic acid, wherein said nucleic acid encodes a protein comprising an alanyl-tRNA synthetase which is encoded by pTR94 as deposited under ATCC Accession No. 98269.

33. Plasmid pTR94, from host cells deposited under ATCC Accession No. 98269.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3344 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 111..3014

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GGTACAGCTG | CGCGTCTGCG | GGAATAGGTG | CAGCGGGCCC | TTGGCGGGGG | ACTCTGAGGG | | | | | | | | | | | 60 |
| AGGAGCTGGG | GACGGCGACC | CTAGGAGAGT | TCTTTGGGGT | GACTTCAAG | ATG | GAC | | | | | | | | | | 116 |
| | | | | | Met | Asp | | | | | | | | | | |
| | | | | | 1 | | | | | | | | | | | |

| TCT | ACT | CTA | ACA | GCA | AGT | GAA | ATC | CGG | CAG | CGA | TTT | ATA | GAT | TTC | TTC | 164 |
|---|---|---|---|---|---|---|---|---|---|---|---|---|---|---|---|---|
| Ser | Thr | Leu | Thr | Ala | Ser | Glu | Ile | Arg | Gln | Arg | Phe | Ile | Asp | Phe | Phe | |
| | | | 5 | | | | 10 | | | | | 15 | | | | |
| AAG | AGG | AAC | GAG | CAT | ACG | TAT | GTT | CAC | TCG | TCT | GCC | ACC | ATC | CCA | TTG | 212 |
| Lys | Arg | Asn | Glu | His | Thr | Tyr | Val | His | Ser | Ser | Ala | Thr | Ile | Pro | Leu | |
| | | 20 | | | | 25 | | | | | 30 | | | | | |
| GAT | GAC | CCC | ACT | TTG | CTC | TTT | GCC | AAT | GCA | GGC | ATG | AAC | CAG | TTT | AAA | 260 |
| Asp | Asp | Pro | Thr | Leu | Leu | Phe | Ala | Asn | Ala | Gly | Met | Asn | Gln | Phe | Lys | |
| 35 | | | | | 40 | | | | | 45 | | | | | 50 | |
| CCC | ATT | TTC | CTG | AAC | ACA | ATT | GAC | CCA | TCT | CAC | CCC | ATG | GCA | AAG | CTG | 308 |
| Pro | Ile | Phe | Leu | Asn | Thr | Ile | Asp | Pro | Ser | His | Pro | Met | Ala | Lys | Leu | |
| | | | | 55 | | | | | 60 | | | | | 65 | | |
| AGC | AGA | GCT | GCC | AAT | ACC | CAG | AAG | TGC | ATC | CGG | GCT | GGG | GGC | AAA | CAA | 356 |
| Ser | Arg | Ala | Ala | Asn | Thr | Gln | Lys | Cys | Ile | Arg | Ala | Gly | Gly | Lys | Gln | |
| | | | 70 | | | | | 75 | | | | | 80 | | | |
| AAT | GAC | CTG | GAC | GAT | GTG | GGC | AAG | GAT | GTC | TAT | CAT | CAC | ACC | TTC | TTC | 404 |
| Asn | Asp | Leu | Asp | Asp | Val | Gly | Lys | Asp | Val | Tyr | His | His | Thr | Phe | Phe | |
| | | 85 | | | | 90 | | | | | 95 | | | | | |
| GAG | ATG | CTG | GGC | TCT | TGG | TCT | TTT | GGA | GAT | TAC | TTT | AAG | GAA | TTG | GCA | 452 |
| Glu | Met | Leu | Gly | Ser | Trp | Ser | Phe | Gly | Asp | Tyr | Phe | Lys | Glu | Leu | Ala | |
| 100 | | | | | 105 | | | | | 110 | | | | | | |
| TGT | AAG | ATG | GCT | CTG | GAA | CTC | CTC | ACC | CAA | GAG | TTT | GGC | ATT | CCC | ATT | 500 |
| Cys | Lys | Met | Ala | Leu | Glu | Leu | Leu | Thr | Gln | Glu | Phe | Gly | Ile | Pro | Ile | |
| 115 | | | | | 120 | | | | | 125 | | | | | 130 | |
| GAA | AGA | CTT | TAT | GTT | ACT | TAC | TTT | GGC | GGG | GAT | GAA | GCA | GCT | GGC | TTA | 548 |
| Glu | Arg | Leu | Tyr | Val | Thr | Tyr | Phe | Gly | Gly | Asp | Glu | Ala | Ala | Gly | Leu | |
| | | | | 135 | | | | | 140 | | | | | 145 | | |
| GAA | GCA | GAT | CTG | GAA | TGC | AAA | CAG | ATC | TGG | CAA | AAT | TTG | GGG | CTG | GAT | 596 |
| Glu | Ala | Asp | Leu | Glu | Cys | Lys | Gln | Ile | Trp | Gln | Asn | Leu | Gly | Leu | Asp | |
| | | | 150 | | | | | 155 | | | | | 160 | | | |
| GAC | ACC | AAA | ATC | CTC | CCA | GGC | AAC | ATG | AAG | GAT | AAC | TTC | TGG | GAG | ATG | 644 |
| Asp | Thr | Lys | Ile | Leu | Pro | Gly | Asn | Met | Lys | Asp | Asn | Phe | Trp | Glu | Met | |
| | | 165 | | | | | 170 | | | | | 175 | | | | |
| GGT | GAC | ACG | GGC | CCC | TGT | GGT | CCT | TGC | AGT | GAG | ATC | CAC | TAC | GAC | CGG | 692 |
| Gly | Asp | Thr | Gly | Pro | Cys | Gly | Pro | Cys | Ser | Glu | Ile | His | Tyr | Asp | Arg | |
| | 180 | | | | | 185 | | | | | 190 | | | | | |
| ATT | GGT | GGT | CGG | GAC | GCC | GCA | CAT | CTT | GTC | AAC | CAG | GAC | GAC | CCT | AAT | 740 |
| Ile | Gly | Gly | Arg | Asp | Ala | Ala | His | Leu | Val | Asn | Gln | Asp | Asp | Pro | Asn | |
| 195 | | | | | 200 | | | | | 205 | | | | | 210 | |
| GTG | CTG | GAG | ATC | TGG | AAC | CTT | GTG | TTC | ATC | CAG | TAT | AAC | AGG | GAA | GCT | 788 |
| Val | Leu | Glu | Ile | Trp | Asn | Leu | Val | Phe | Ile | Gln | Tyr | Asn | Arg | Glu | Ala | |
| | | | | 215 | | | | | 220 | | | | | 225 | | |
| GAT | GGC | ATT | CTG | AAA | CCT | CTT | CCC | AAG | AAA | AGC | ATT | GAC | ACA | GGG | ATG | 836 |
| Asp | Gly | Ile | Leu | Lys | Pro | Leu | Pro | Lys | Lys | Ser | Ile | Asp | Thr | Gly | Met | |
| | | | 230 | | | | | 235 | | | | | 240 | | | |
| GGC | CTG | GAA | CGA | CTG | GTA | TCT | GTG | CTG | CAG | AAT | AAG | ATG | TCC | AAC | TAT | 884 |
| Gly | Leu | Glu | Arg | Leu | Val | Ser | Val | Leu | Gln | Asn | Lys | Met | Ser | Asn | Tyr | |
| | | 245 | | | | | 250 | | | | | 255 | | | | |
| GAC | ACT | GAC | CTT | TTT | GTC | CCT | TAC | TTT | GAA | GCC | ATT | CAG | AAG | GGC | ACA | 932 |
| Asp | Thr | Asp | Leu | Phe | Val | Pro | Tyr | Phe | Glu | Ala | Ile | Gln | Lys | Gly | Thr | |
| | 260 | | | | | 265 | | | | | 270 | | | | | |
| GGT | GCC | CGA | CCA | TAC | ACT | GGG | AAA | GTT | GGT | GCT | GAG | GAT | GCC | GAT | GGG | 980 |
| Gly | Ala | Arg | Pro | Tyr | Thr | Gly | Lys | Val | Gly | Ala | Glu | Asp | Ala | Asp | Gly | |
| 275 | | | | | 280 | | | | | 285 | | | | | 290 | |
| ATT | GAC | ATG | GCC | TAC | CGG | GTG | CTG | GCT | GAC | CAT | GCT | CGG | ACC | ATC | ACT | 1028 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ile | Asp | Met | Ala | Tyr<br>295 | Arg | Val | Leu | Ala | Asp<br>300 | His | Ala | Arg | Thr | Ile<br>305 | Thr |      |
| GTG | GCA | CTG | GCT | GAT | GGT | GGC | CGG | CCT | GAC | AAC | ACA | GGG | CGT | GGA | TAT | 1076 |
| Val | Ala | Leu | Ala<br>310 | Asp | Gly | Gly | Arg | Pro<br>315 | Asp | Asn | Thr | Gly | Arg<br>320 | Gly | Tyr |      |
| GTG | TTG | AGA | CGG | ATT | CTC | CGC | CGA | GCT | GTC | CGA | TAC | GCC | CAT | GAA | AAG | 1124 |
| Val | Leu | Arg<br>325 | Arg | Ile | Leu | Arg | Arg<br>330 | Ala | Val | Arg | Tyr | Ala<br>335 | His | Glu | Lys |      |
| CTC | AAT | GCC | AGC | AGG | GGC | TTC | TTT | GCT | ACG | TTA | GTG | GAT | GTT | GTC | GTC | 1172 |
| Leu | Asn | Ala<br>340 | Ser | Arg | Gly | Phe | Phe<br>345 | Ala | Thr | Leu | Val | Asp<br>350 | Val | Val | Val |      |
| CAG | TCC | CTG | GGA | GAT | GCA | TTT | CCT | GAG | CTG | AAG | AAG | GAC | CCA | GAC | ATG | 1220 |
| Gln | Ser | Leu<br>355 | Gly | Asp | Ala | Phe<br>360 | Pro | Glu | Leu | Lys | Lys<br>365 | Asp | Pro | Asp | Met<br>370 |      |
| GTG | AAG | GAC | ATC | ATT | AAT | GAA | GAA | GAG | GTG | CAG | TTT | CTC | AAG | ACT | CTC | 1268 |
| Val | Lys | Asp | Ile | Ile<br>375 | Asn | Glu | Glu | Glu | Val<br>380 | Gln | Phe | Leu | Lys | Thr<br>385 | Leu |      |
| AGC | AGA | GGG | CGT | CGC | ATC | CTG | GAC | AGG | AAA | ATT | CAG | AGC | CTG | GGA | GAC | 1316 |
| Ser | Arg | Gly | Arg<br>390 | Arg | Ile | Leu | Asp | Arg<br>395 | Lys | Ile | Gln | Ser | Leu<br>400 | Gly | Asp |      |
| AGC | AAG | ACC | ATT | CCC | GGA | GAC | ACT | GCT | TGG | CTC | CTC | TAT | GAC | ACC | TAT | 1364 |
| Ser | Lys | Thr | Ile | Pro<br>405 | Gly | Asp | Thr | Ala | Trp<br>410 | Leu | Leu | Tyr | Asp | Thr<br>415 | Tyr |      |
| GGG | TTT | CCA | GTG | GAT | CTG | ACT | GGA | CTG | ATT | GCT | GAA | GAG | AAG | GGC | CTG | 1412 |
| Gly | Phe | Pro | Val<br>420 | Asp | Leu | Thr | Gly | Leu<br>425 | Ile | Ala | Glu | Glu | Lys<br>430 | Gly | Leu |      |
| GTG | GTA | GAC | ATG | GAT | GGC | TTT | GAA | GAG | GAG | AGG | AAA | CTG | GCC | CAG | CTG | 1460 |
| Val | Val<br>435 | Asp | Met | Asp | Gly | Phe<br>440 | Glu | Glu | Glu | Arg | Lys<br>445 | Leu | Ala | Gln | Leu<br>450 |      |
| AAA | TCA | CAG | GGC | AAG | GGA | GCT | GGT | GGG | GAA | GAC | CTC | ATT | ATG | CTG | GAC | 1508 |
| Lys | Ser | Gln | Gly | Lys<br>455 | Gly | Ala | Gly | Gly | Glu<br>460 | Asp | Leu | Ile | Met | Leu<br>465 | Asp |      |
| ATT | TAC | GCT | ATC | GAA | GAG | CTC | CGG | GCA | CGG | GGT | CTG | GAG | GTC | ACA | GAT | 1556 |
| Ile | Tyr | Ala | Ile<br>470 | Glu | Glu | Leu | Arg | Ala<br>475 | Arg | Gly | Leu | Glu | Val<br>480 | Thr | Asp |      |
| GAT | TCC | CCA | AAG | TAC | AAT | TAC | CAT | TTG | GAC | TCC | AGT | GGT | AGC | TAT | GTA | 1604 |
| Asp | Ser | Pro | Lys<br>485 | Tyr | Asn | Tyr | His | Leu<br>490 | Asp | Ser | Ser | Gly | Ser<br>495 | Tyr | Val |      |
| TTT | GAG | AAC | ACA | GTG | GCT | ACG | GTG | ATG | GCT | CTG | CGC | AGG | GAG | AAG | ATG | 1652 |
| Phe | Glu | Asn | Thr | Val<br>500 | Ala | Thr | Val | Met | Ala<br>505 | Leu | Arg | Arg | Glu | Lys<br>510 | Met |      |
| TTC | GTG | GAA | GAG | GTG | TCC | ACA | GGC | CAG | GAG | TGT | GGA | GTG | GTG | CTG | GAC | 1700 |
| Phe<br>515 | Val | Glu | Glu | Val | Ser<br>520 | Thr | Gly | Gln | Glu | Cys<br>525 | Gly | Val | Val | Leu | Asp<br>530 |      |
| AAG | ACC | TGT | TTC | TAT | GCT | GAG | CAA | GGA | GGC | CAG | ATC | TAT | GAC | GAA | GGC | 1748 |
| Lys | Thr | Cys | Phe | Tyr<br>535 | Ala | Glu | Gln | Gly | Gly<br>540 | Gln | Ile | Tyr | Asp | Glu<br>545 | Gly |      |
| TAC | CTG | GTG | AAG | GTG | GAT | GAC | AGC | AGT | GAA | GAT | AAA | ACA | GAG | TTT | ACA | 1796 |
| Tyr | Leu | Val | Lys<br>550 | Val | Asp | Asp | Ser | Ser<br>555 | Glu | Asp | Lys | Thr | Glu<br>560 | Phe | Thr |      |
| GTG | AAG | AAT | GCT | CAG | GTC | CGA | GGA | GGG | TAT | GTG | CTA | CAC | ATT | GGA | ACC | 1844 |
| Val | Lys | Asn<br>565 | Ala | Gln | Val | Arg | Gly<br>570 | Gly | Tyr | Val | Leu | His<br>575 | Ile | Gly | Thr |      |
| ATC | TAC | GGT | GAC | CTG | AAA | GTG | GGG | GAT | CAG | GTC | TGG | CTG | TTT | ATT | GAT | 1892 |
| Ile | Tyr | Gly<br>580 | Asp | Leu | Lys | Val | Gly<br>585 | Asp | Gln | Val | Trp | Leu<br>590 | Phe | Ile | Asp |      |
| GAG | CCC | CGA | CGA | AGA | CCC | ATC | ATG | AGC | AAC | CAC | ACA | GCT | ACG | CAC | ATT | 1940 |
| Glu<br>595 | Pro | Arg | Arg | Arg | Pro<br>600 | Ile | Met | Ser | Asn | His<br>605 | Thr | Ala | Thr | His<br>610 | Ile |      |
| CTG | AAC | TTC | GCC | CTG | CGC | TCA | GTG | CTT | GGG | GAA | GCT | GAC | CAG | AAA | GGC | 1988 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Leu | Asn | Phe | Ala | Leu | Arg | Ser | Val | Leu | Gly | Glu | Ala | Asp | Gln | Lys | Gly |      |
|     |     |     |     | 615 |     |     |     |     | 620 |     |     |     |     | 625 |     |      |

| TCA | TTG | GTT | GCT | CCT | GAC | CGC | CTC | AGA | TTT | GAC | TTT | ACT | GCC | AAG | GGA | 2036 |
|-----|-----|-----|-----|-----|-----|-----|-----|-----|-----|-----|-----|-----|-----|-----|-----|------|
| Ser | Leu | Val | Ala | Pro | Asp | Arg | Leu | Arg | Phe | Asp | Phe | Thr | Ala | Lys | Gly |      |
|     |     |     | 630 |     |     |     |     | 635 |     |     |     |     | 640 |     |     |      |

| GCC | ATG | TCC | ACC | CAA | CAG | ATC | AAG | AAG | GCT | GAA | GAG | ATT | GCT | AAT | GAG | 2084 |
| Ala | Met | Ser | Thr | Gln | Gln | Ile | Lys | Lys | Ala | Glu | Glu | Ile | Ala | Asn | Glu |      |
|     |     |     | 645 |     |     |     |     | 650 |     |     |     |     | 655 |     |     |      |

| ATG | ATT | GAG | GCA | GCC | AAG | GCC | GTC | TAT | ACC | CAG | GAT | TGC | CCC | CTG | GCA | 2132 |
| Met | Ile | Glu | Ala | Ala | Lys | Ala | Val | Tyr | Thr | Gln | Asp | Cys | Pro | Leu | Ala |      |
|     |     | 660 |     |     |     |     | 665 |     |     |     |     | 670 |     |     |     |      |

| GCA | GCG | AAA | GCC | ATC | CAG | GGC | CTA | CGG | GCT | GTG | TTT | GAT | GAG | ACC | TAT | 2180 |
| Ala | Ala | Lys | Ala | Ile | Gln | Gly | Leu | Arg | Ala | Val | Phe | Asp | Glu | Thr | Tyr |      |
| 675 |     |     |     |     | 680 |     |     |     |     | 685 |     |     |     |     | 690 |      |

| CCT | GAC | CCT | GTG | CGA | GTC | GTC | TCC | ATT | GGG | GTC | CCG | GTG | TCC | GAG | TTG | 2228 |
| Pro | Asp | Pro | Val | Arg | Val | Val | Ser | Ile | Gly | Val | Pro | Val | Ser | Glu | Leu |      |
|     |     |     |     | 695 |     |     |     |     | 700 |     |     |     |     | 705 |     |      |

| CTG | GAT | GAC | CCC | TCT | GGG | CCT | GCT | GGC | TCC | CTG | ACT | TCT | GTT | GAG | TTC | 2276 |
| Leu | Asp | Asp | Pro | Ser | Gly | Pro | Ala | Gly | Ser | Leu | Thr | Ser | Val | Glu | Phe |      |
|     |     |     | 710 |     |     |     |     | 715 |     |     |     |     | 720 |     |     |      |

| TGT | GGG | GGA | ACG | CAC | CTG | CGG | AAC | TCG | AGT | CAT | GCA | GGA | GCT | TTT | GTG | 2324 |
| Cys | Gly | Gly | Thr | His | Leu | Arg | Asn | Ser | Ser | His | Ala | Gly | Ala | Phe | Val |      |
|     |     | 725 |     |     |     |     | 730 |     |     |     |     | 735 |     |     |     |      |

| ATC | GTG | ACG | GAA | GAA | GCC | ATT | GCC | AAG | GGT | ATC | CGG | AGG | ATT | GTG | GCT | 2372 |
| Ile | Val | Thr | Glu | Glu | Ala | Ile | Ala | Lys | Gly | Ile | Arg | Arg | Ile | Val | Ala |      |
|     | 740 |     |     |     |     | 745 |     |     |     |     | 750 |     |     |     |     |      |

| GTC | ACA | GGT | GCC | GAG | GCC | CAG | AAG | GCC | CTC | AGG | AAA | GCA | GAG | AGC | TTG | 2420 |
| Val | Thr | Gly | Ala | Glu | Ala | Gln | Lys | Ala | Leu | Arg | Lys | Ala | Glu | Ser | Leu |      |
| 755 |     |     |     |     | 760 |     |     |     |     | 765 |     |     |     |     | 770 |      |

| AAG | AAA | TGT | CTC | TCT | GTC | ATG | GAA | GCC | AAA | GTG | AAG | GCT | CAG | ACT | GCT | 2468 |
| Lys | Lys | Cys | Leu | Ser | Val | Met | Glu | Ala | Lys | Val | Lys | Ala | Gln | Thr | Ala |      |
|     |     |     |     | 775 |     |     |     |     | 780 |     |     |     |     | 785 |     |      |

| CCA | AAC | AAG | GAT | GTG | CAG | AGG | GAG | ATC | GCT | GAC | CTT | GGA | GAG | GCC | CTG | 2516 |
| Pro | Asn | Lys | Asp | Val | Gln | Arg | Glu | Ile | Ala | Asp | Leu | Gly | Glu | Ala | Leu |      |
|     |     |     | 790 |     |     |     |     | 795 |     |     |     |     | 800 |     |     |      |

| GCC | ACT | GCA | GTC | ATC | CCC | CAG | TGG | CAG | AAG | GAT | GAA | TTG | CGG | GAG | ACT | 2564 |
| Ala | Thr | Ala | Val | Ile | Pro | Gln | Trp | Gln | Lys | Asp | Glu | Leu | Arg | Glu | Thr |      |
|     |     | 805 |     |     |     |     | 810 |     |     |     |     | 815 |     |     |     |      |

| CTC | AAA | TCC | CTA | AAG | AAG | GTC | ATG | GAT | GAC | TTG | GAC | CGA | GCC | AGC | AAA | 2612 |
| Leu | Lys | Ser | Leu | Lys | Lys | Val | Met | Asp | Asp | Leu | Asp | Arg | Ala | Ser | Lys |      |
|     | 820 |     |     |     |     | 825 |     |     |     |     | 830 |     |     |     |     |      |

| GCC | GAT | GTC | CAG | AAA | CGA | GTG | TTA | GAG | AAG | ACG | AAG | CAG | TTC | ATC | GAC | 2660 |
| Ala | Asp | Val | Gln | Lys | Arg | Val | Leu | Glu | Lys | Thr | Lys | Gln | Phe | Ile | Asp |      |
| 835 |     |     |     |     | 840 |     |     |     |     | 845 |     |     |     |     | 850 |      |

| AGC | AAC | CCC | AAC | CAG | CCT | CTT | GTC | ATC | CTG | GAG | ATG | GAG | AGC | GGC | GCC | 2708 |
| Ser | Asn | Pro | Asn | Gln | Pro | Leu | Val | Ile | Leu | Glu | Met | Glu | Ser | Gly | Ala |      |
|     |     |     |     | 855 |     |     |     |     | 860 |     |     |     |     | 865 |     |      |

| TCA | GCC | AAG | GCC | CTG | AAT | GAA | GCC | TTG | AAG | CTC | TTC | AAG | ATG | CAC | TCC | 2756 |
| Ser | Ala | Lys | Ala | Leu | Asn | Glu | Ala | Leu | Lys | Leu | Phe | Lys | Met | His | Ser |      |
|     |     | 870 |     |     |     |     | 875 |     |     |     |     | 880 |     |     |     |      |

| CCT | CAG | ACT | TCT | GCC | ATG | CTC | TTC | ACG | GTG | GAC | AAT | GAG | GCT | GGC | AAG | 2804 |
| Pro | Gln | Thr | Ser | Ala | Met | Leu | Phe | Thr | Val | Asp | Asn | Glu | Ala | Gly | Lys |      |
|     |     | 885 |     |     |     |     | 890 |     |     |     |     | 895 |     |     |     |      |

| ATC | ACG | TGC | CTG | TGT | CAA | GTC | CCC | CAG | AAT | GCA | GCC | AAT | CGG | GGC | TTA | 2852 |
| Ile | Thr | Cys | Leu | Cys | Gln | Val | Pro | Gln | Asn | Ala | Ala | Asn | Arg | Gly | Leu |      |
|     | 900 |     |     |     |     | 905 |     |     |     |     | 910 |     |     |     |     |      |

| AAA | GCC | AGC | GAG | TGG | GTG | CAG | CAG | GTG | TCA | GGC | TTG | ATG | GAC | GGT | AAA | 2900 |
| Lys | Ala | Ser | Glu | Trp | Val | Gln | Gln | Val | Ser | Gly | Leu | Met | Asp | Gly | Lys |      |
| 915 |     |     |     | 920 |     |     |     |     | 925 |     |     |     |     | 930 |     |      |

| GGT | GGT | GGC | AAG | GAT | GTG | TCT | GCA | CAG | GCC | ACA | GGC | AAG | AAC | GTT | GGC | 2948 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Gly | Gly | Gly | Lys | Asp | Val | Ser | Ala | Gln | Ala | Thr | Gly | Lys | Asn | Val | Gly |     |
|     |     |     |     | 935 |     |     |     |     | 940 |     |     |     |     | 945 |     |     |
| TGC | CTG | CAG | GAG | GCG | CTG | CAG | CTG | GCC | ACT | TCC | TTC | GCC | CAG | CTG | CGC | 2996 |
| Cys | Leu | Gln | Glu | Ala | Leu | Gln | Leu | Ala | Thr | Ser | Phe | Ala | Gln | Leu | Arg |     |
|     |     |     |     | 950 |     |     |     |     | 955 |     |     |     |     | 960 |     |     |
| CTC | GGG | GAT | GTA | AAG | AAC | TGAGTGGGGA | AGGAGGAGGC | TCCCACTGGA |     |     |     |     |     |     |     | 3044 |
| Leu | Gly | Asp | Val | Lys | Asn |     |     |     |     |     |     |     |     |     |     |     |
|     |     |     | 965 |     |     |     |     |     |     |     |     |     |     |     |     |     |

```
TCCATCCGTC CAGCCAAGAG CTCTTCATCT GCTACAAGAA CATTTGAATC TTGGGACCTT    3104

TAAAGAGCCC CTCCTAACCC AGCAGTAACT GGAACACACT TGGGAGCAGT CCTATGTCTC    3164

AGTGCCCCTT AAATTTCTGC CCTGAGCCCT CCACGTCAGT GCCATCGGTC TAGAACCACT    3224

AACCCCGCAT TGCTGTTGAT CGTCACGCTC GCATCTATAG ATAACGGCTC TCCAGACCTG    3284

AGCTTTCCGC GTCAGCAAGT AGGAATCGTT TTTGCTGCAG AGAATAAAAG GACCACGTGC    3344
```

( 2 ) INFORMATION FOR SEQ ID NO:2:

( i ) SEQUENCE CHARACTERISTICS:
        ( A ) LENGTH: 968 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Asp | Ser | Thr | Leu | Thr | Ala | Ser | Glu | Ile | Arg | Gln | Arg | Phe | Ile | Asp |
| 1 |     |     |     | 5 |     |     |     |     | 10 |     |     |     |     | 15 |     |
| Phe | Phe | Lys | Arg | Asn | Glu | His | Thr | Tyr | Val | His | Ser | Ser | Ala | Thr | Ile |
|     |     |     | 20 |     |     |     |     | 25 |     |     |     |     | 30 |     |     |
| Pro | Leu | Asp | Asp | Pro | Thr | Leu | Leu | Phe | Ala | Asn | Ala | Gly | Met | Asn | Gln |
|     |     | 35 |     |     |     |     | 40 |     |     |     |     | 45 |     |     |     |
| Phe | Lys | Pro | Ile | Phe | Leu | Asn | Thr | Ile | Asp | Pro | Ser | His | Pro | Met | Ala |
|     | 50 |     |     |     |     | 55 |     |     |     |     | 60 |     |     |     |     |
| Lys | Leu | Ser | Arg | Ala | Ala | Asn | Thr | Gln | Lys | Cys | Ile | Arg | Ala | Gly | Gly |
| 65 |     |     |     |     | 70 |     |     |     |     | 75 |     |     |     |     | 80 |
| Lys | Gln | Asn | Asp | Leu | Asp | Asp | Val | Gly | Lys | Asp | Val | Tyr | His | His | Thr |
|     |     |     |     | 85 |     |     |     |     | 90 |     |     |     |     | 95 |     |
| Phe | Phe | Glu | Met | Leu | Gly | Ser | Trp | Ser | Phe | Gly | Asp | Tyr | Phe | Lys | Glu |
|     |     |     | 100 |     |     |     |     | 105 |     |     |     |     | 110 |     |     |
| Leu | Ala | Cys | Lys | Met | Ala | Leu | Glu | Leu | Leu | Thr | Gln | Glu | Phe | Gly | Ile |
|     |     | 115 |     |     |     |     | 120 |     |     |     |     | 125 |     |     |     |
| Pro | Ile | Glu | Arg | Leu | Tyr | Val | Thr | Tyr | Phe | Gly | Gly | Asp | Glu | Ala | Ala |
|     | 130 |     |     |     |     | 135 |     |     |     |     | 140 |     |     |     |     |
| Gly | Leu | Glu | Ala | Asp | Leu | Glu | Cys | Lys | Gln | Ile | Trp | Gln | Asn | Leu | Gly |
| 145 |     |     |     |     | 150 |     |     |     |     | 155 |     |     |     |     | 160 |
| Leu | Asp | Asp | Thr | Lys | Ile | Leu | Pro | Gly | Asn | Met | Lys | Asp | Asn | Phe | Trp |
|     |     |     |     | 165 |     |     |     |     | 170 |     |     |     |     | 175 |     |
| Glu | Met | Gly | Asp | Thr | Gly | Pro | Cys | Gly | Pro | Cys | Ser | Glu | Ile | His | Tyr |
|     |     |     | 180 |     |     |     |     | 185 |     |     |     |     | 190 |     |     |
| Asp | Arg | Ile | Gly | Gly | Arg | Asp | Ala | Ala | His | Leu | Val | Asn | Gln | Asp | Asp |
|     |     | 195 |     |     |     |     | 200 |     |     |     |     | 205 |     |     |     |
| Pro | Asn | Val | Leu | Glu | Ile | Trp | Asn | Leu | Val | Phe | Ile | Gln | Tyr | Asn | Arg |
|     | 210 |     |     |     |     | 215 |     |     |     |     | 220 |     |     |     |     |
| Glu | Ala | Asp | Gly | Ile | Leu | Lys | Pro | Leu | Pro | Lys | Lys | Ser | Ile | Asp | Thr |
| 225 |     |     |     |     | 230 |     |     |     |     | 235 |     |     |     |     | 240 |
| Gly | Met | Gly | Leu | Glu | Arg | Leu | Val | Ser | Val | Leu | Gln | Asn | Lys | Met | Ser |
|     |     |     |     | 245 |     |     |     |     | 250 |     |     |     |     | 255 |     |

| | | | | | | | | | | | | | | |
|---|---|---|---|---|---|---|---|---|---|---|---|---|---|---|
| Asn | Tyr | Asp | Thr | Asp | Leu | Phe | Val | Pro | Tyr | Phe | Glu | Ala | Ile | Gln | Lys |
| | | | 260 | | | | 265 | | | | 270 | | | | |
| Gly | Thr | Gly | Ala | Arg | Pro | Tyr | Thr | Gly | Lys | Val | Gly | Ala | Glu | Asp | Ala |
| | | 275 | | | | 280 | | | | | 285 | | | | |
| Asp | Gly | Ile | Asp | Met | Ala | Tyr | Arg | Val | Leu | Ala | Asp | His | Ala | Arg | Thr |
| | 290 | | | | | 295 | | | | | 300 | | | | |
| Ile | Thr | Val | Ala | Leu | Ala | Asp | Gly | Gly | Arg | Pro | Asp | Asn | Thr | Gly | Arg |
| 305 | | | | | 310 | | | | | 315 | | | | | 320 |
| Gly | Tyr | Val | Leu | Arg | Arg | Ile | Leu | Arg | Arg | Ala | Val | Arg | Tyr | Ala | His |
| | | | | 325 | | | | | 330 | | | | | 335 | |
| Glu | Lys | Leu | Asn | Ala | Ser | Arg | Gly | Phe | Phe | Ala | Thr | Leu | Val | Asp | Val |
| | | | | 340 | | | | | 345 | | | | | 350 | |
| Val | Val | Gln | Ser | Leu | Gly | Asp | Ala | Phe | Pro | Glu | Leu | Lys | Lys | Asp | Pro |
| | | | 355 | | | | | 360 | | | | | 365 | | |
| Asp | Met | Val | Lys | Asp | Ile | Ile | Asn | Glu | Glu | Glu | Val | Gln | Phe | Leu | Lys |
| | 370 | | | | | 375 | | | | | 380 | | | | |
| Thr | Leu | Ser | Arg | Gly | Arg | Arg | Ile | Leu | Asp | Arg | Lys | Ile | Gln | Ser | Leu |
| 385 | | | | | 390 | | | | | 395 | | | | | 400 |
| Gly | Asp | Ser | Lys | Thr | Ile | Pro | Gly | Asp | Thr | Ala | Trp | Leu | Leu | Tyr | Asp |
| | | | | 405 | | | | | 410 | | | | | 415 | |
| Thr | Tyr | Gly | Phe | Pro | Val | Asp | Leu | Thr | Gly | Leu | Ile | Ala | Glu | Glu | Lys |
| | | | | 420 | | | | | 425 | | | | | 430 | |
| Gly | Leu | Val | Val | Asp | Met | Asp | Gly | Phe | Glu | Glu | Glu | Arg | Lys | Leu | Ala |
| | | | 435 | | | | | 440 | | | | | 445 | | |
| Gln | Leu | Lys | Ser | Gln | Gly | Lys | Gly | Ala | Gly | Gly | Glu | Asp | Leu | Ile | Met |
| | 450 | | | | | 455 | | | | | 460 | | | | |
| Leu | Asp | Ile | Tyr | Ala | Ile | Glu | Glu | Leu | Arg | Ala | Arg | Gly | Leu | Glu | Val |
| 465 | | | | | 470 | | | | | 475 | | | | | 480 |
| Thr | Asp | Asp | Ser | Pro | Lys | Tyr | Asn | Tyr | His | Leu | Asp | Ser | Ser | Gly | Ser |
| | | | | 485 | | | | | 490 | | | | | 495 | |
| Tyr | Val | Phe | Glu | Asn | Thr | Val | Ala | Thr | Val | Met | Ala | Leu | Arg | Arg | Glu |
| | | | | 500 | | | | | 505 | | | | | 510 | |
| Lys | Met | Phe | Val | Glu | Glu | Val | Ser | Thr | Gly | Gln | Glu | Cys | Gly | Val | Val |
| | | | 515 | | | | | 520 | | | | | 525 | | |
| Leu | Asp | Lys | Thr | Cys | Phe | Tyr | Ala | Glu | Gln | Gly | Gly | Gln | Ile | Tyr | Asp |
| | | | 530 | | | | | 535 | | | | | 540 | | |
| Glu | Gly | Tyr | Leu | Val | Lys | Val | Asp | Asp | Ser | Ser | Glu | Asp | Lys | Thr | Glu |
| 545 | | | | | 550 | | | | | 555 | | | | | 560 |
| Phe | Thr | Val | Lys | Asn | Ala | Gln | Val | Arg | Gly | Gly | Tyr | Val | Leu | His | Ile |
| | | | | 565 | | | | | 570 | | | | | 575 | |
| Gly | Thr | Ile | Tyr | Gly | Asp | Leu | Lys | Val | Gly | Asp | Gln | Val | Trp | Leu | Phe |
| | | | | 580 | | | | | 585 | | | | | 590 | |
| Ile | Asp | Glu | Pro | Arg | Arg | Arg | Pro | Ile | Met | Ser | Asn | His | Thr | Ala | Thr |
| | | | 595 | | | | | 600 | | | | | 605 | | |
| His | Ile | Leu | Asn | Phe | Ala | Leu | Arg | Ser | Val | Leu | Gly | Glu | Ala | Asp | Gln |
| | 610 | | | | | 615 | | | | | 620 | | | | |
| Lys | Gly | Ser | Leu | Val | Ala | Pro | Asp | Arg | Leu | Arg | Phe | Asp | Phe | Thr | Ala |
| 625 | | | | | 630 | | | | | 635 | | | | | 640 |
| Lys | Gly | Ala | Met | Ser | Thr | Gln | Gln | Ile | Lys | Lys | Ala | Glu | Glu | Ile | Ala |
| | | | | 645 | | | | | 650 | | | | | 655 | |
| Asn | Glu | Met | Ile | Glu | Ala | Ala | Lys | Ala | Val | Tyr | Thr | Gln | Asp | Cys | Pro |
| | | | 660 | | | | | 665 | | | | | 670 | | |
| Leu | Ala | Ala | Ala | Lys | Ala | Ile | Gln | Gly | Leu | Arg | Ala | Val | Phe | Asp | Glu |

```
                        675                     680                     685
Thr Tyr Pro Asp Pro Val Arg Val Val Ser Ile Gly Val Pro Val Ser
    690                     695                 700
Glu Leu Leu Asp Asp Pro Ser Gly Pro Ala Gly Ser Leu Thr Ser Val
705                     710                 715                     720
Glu Phe Cys Gly Gly Thr His Leu Arg Asn Ser Ser His Ala Gly Ala
                    725                 730                 735
Phe Val Ile Val Thr Glu Glu Ala Ile Ala Lys Gly Ile Arg Arg Ile
                740                 745                 750
Val Ala Val Thr Gly Ala Glu Ala Gln Lys Ala Leu Arg Lys Ala Glu
            755                 760                 765
Ser Leu Lys Lys Cys Leu Ser Val Met Glu Ala Lys Val Lys Ala Gln
770                 775                 780
Thr Ala Pro Asn Lys Asp Val Gln Arg Glu Ile Ala Asp Leu Gly Glu
785                 790                 795                     800
Ala Leu Ala Thr Ala Val Ile Pro Gln Trp Gln Lys Asp Glu Leu Arg
            805                     810                 815
Glu Thr Leu Lys Ser Leu Lys Lys Val Met Asp Asp Leu Asp Arg Ala
            820                 825                 830
Ser Lys Ala Asp Val Gln Lys Arg Val Leu Glu Lys Thr Lys Gln Phe
        835                 840                 845
Ile Asp Ser Asn Pro Asn Gln Pro Leu Val Ile Leu Glu Met Glu Ser
    850                 855                 860
Gly Ala Ser Ala Lys Ala Leu Asn Glu Ala Leu Lys Leu Phe Lys Met
865                 870                 875                 880
His Ser Pro Gln Thr Ser Ala Met Leu Phe Thr Val Asp Asn Glu Ala
                885                 890                 895
Gly Lys Ile Thr Cys Leu Cys Gln Val Pro Gln Asn Ala Ala Asn Arg
                900                 905                 910
Gly Leu Lys Ala Ser Glu Trp Val Gln Val Ser Gly Leu Met Asp
            915                 920                 925
Gly Lys Gly Gly Gly Lys Asp Val Ser Ala Gln Ala Thr Gly Lys Asn
        930                 935                 940
Val Gly Cys Leu Gln Glu Ala Leu Gln Leu Ala Thr Ser Phe Ala Gln
945                     950                 955                 960
Leu Arg Leu Gly Asp Val Lys Asn
                965
```

( 2 ) INFORMATION FOR SEQ ID NO:3:

( i ) SEQUENCE CHARACTERISTICS:
        ( A ) LENGTH: 2992 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 64..2937

( x i ) SEQUENCE DESCRIPTION: SEQ ID NO:3:

```
AACTACCGGA TAAGGAACTT GACTCTTTCT TTCAAGCAAT TAACTACATC AACTAGAACC          60

ATA ATG ACG ATC GGT GAT AAG CAA AAA TGG ACC GCT ACT AAT GTC CGT         108
    Met Thr Ile Gly Asp Lys Gln Lys Trp Thr Ala Thr Asn Val Arg
        970                 975                 980

AAT ACC TTT CTA GAC TAT TTC AAA TCT AAA GAA CAC AAG TTT GTC AAA         156
```

| | | | | | | | | | | | | | | | | |
|---|---|---|---|---|---|---|---|---|---|---|---|---|---|---|---|---|
| Asn | Thr | Phe | Leu | Asp | Tyr | Phe | Lys | Ser | Lys | Glu | His | Lys | Phe | Val | Lys | |
| | 985 | | | | 990 | | | | | 995 | | | | | | |

| TCC | TCT | CCA | GTA | GTT | CCA | TTT | GAT | GAT | CCA | ACT | TTA | CTT | TTC | GCT | AAT | 204 |
|---|---|---|---|---|---|---|---|---|---|---|---|---|---|---|---|---|
| Ser | Ser | Pro | Val | Val | Pro | Phe | Asp | Asp | Pro | Thr | Leu | Leu | Phe | Ala | Asn | |
| 1000 | | | | | 1005 | | | | | 1010 | | | | | 1015 | |

| GCC | GGT | ATG | AAC | CAA | TAC | AAG | CCT | ATC | TTT | TTA | GGT | ACT | GTC | GAT | CCA | 252 |
|---|---|---|---|---|---|---|---|---|---|---|---|---|---|---|---|---|
| Ala | Gly | Met | Asn | Gln | Tyr | Lys | Pro | Ile | Phe | Leu | Gly | Thr | Val | Asp | Pro | |
| | | | | 1020 | | | | | 1025 | | | | | 1030 | | |

| GCT | TCC | GAT | TTC | TAC | ACC | TTG | AAA | AGG | GCT | TAC | AAC | TCT | CAA | AAG | TGT | 300 |
|---|---|---|---|---|---|---|---|---|---|---|---|---|---|---|---|---|
| Ala | Ser | Asp | Phe | Tyr | Thr | Leu | Lys | Arg | Ala | Tyr | Asn | Ser | Gln | Lys | Cys | |
| | | | 1035 | | | | | 1040 | | | | | 1045 | | | |

| ATC | AGA | GCT | GGT | GGT | AAA | CAC | AAC | GAT | TTA | GAA | GAT | GTC | GGT | AAG | GAT | 348 |
|---|---|---|---|---|---|---|---|---|---|---|---|---|---|---|---|---|
| Ile | Arg | Ala | Gly | Gly | Lys | His | Asn | Asp | Leu | Glu | Asp | Val | Gly | Lys | Asp | |
| | | | 1050 | | | | | 1055 | | | | | 1060 | | | |

| TCT | TAT | CAT | CAT | ACC | TTT | TTT | GAA | ATG | CTG | GGT | AAC | TGG | TCG | TTT | GGC | 396 |
|---|---|---|---|---|---|---|---|---|---|---|---|---|---|---|---|---|
| Ser | Tyr | His | His | Thr | Phe | Phe | Glu | Met | Leu | Gly | Asn | Trp | Ser | Phe | Gly | |
| | | 1065 | | | | | 1070 | | | | | 1075 | | | | |

| GAC | TAT | TTC | AAG | AAG | GAA | GCT | ATT | ACT | TAC | TCA | TGG | ACT | TTG | TTG | ACT | 444 |
|---|---|---|---|---|---|---|---|---|---|---|---|---|---|---|---|---|
| Asp | Tyr | Phe | Lys | Lys | Glu | Ala | Ile | Thr | Tyr | Ser | Trp | Thr | Leu | Leu | Thr | |
| 1080 | | | | | 1085 | | | | | 1090 | | | | | 1095 | |

| GAA | GTA | TAC | GGC | ATT | CCA | AAG | GAT | AGC | TTA | TAC | GTT | ACC | TAT | TTT | GAA | 492 |
|---|---|---|---|---|---|---|---|---|---|---|---|---|---|---|---|---|
| Glu | Val | Tyr | Gly | Ile | Pro | Lys | Asp | Ser | Leu | Tyr | Val | Thr | Tyr | Phe | Glu | |
| | | | | 1100 | | | | | 1105 | | | | | 1110 | | |

| GGT | GAT | GAA | AAG | TTA | GGC | TTG | GAA | CCT | GAT | ACT | GAA | GCC | CGT | GAA | CTA | 540 |
|---|---|---|---|---|---|---|---|---|---|---|---|---|---|---|---|---|
| Gly | Asp | Glu | Lys | Leu | Gly | Leu | Glu | Pro | Asp | Thr | Glu | Ala | Arg | Glu | Leu | |
| | | | 1115 | | | | | 1120 | | | | | 1125 | | | |

| TGG | AAA | AAT | GTT | GGT | GTT | CCC | GAT | GAC | CAT | ATA | TTA | CCT | GGT | AAT | GCA | 588 |
|---|---|---|---|---|---|---|---|---|---|---|---|---|---|---|---|---|
| Trp | Lys | Asn | Val | Gly | Val | Pro | Asp | Asp | His | Ile | Leu | Pro | Gly | Asn | Ala | |
| | | | 1130 | | | | | 1135 | | | | | 1140 | | | |

| AAG | GAC | AAC | TTT | TGG | GAA | ATG | GGT | GAC | CAA | GGC | CCA | TGT | GGT | CCT | TGT | 636 |
|---|---|---|---|---|---|---|---|---|---|---|---|---|---|---|---|---|
| Lys | Asp | Asn | Phe | Trp | Glu | Met | Gly | Asp | Gln | Gly | Pro | Cys | Gly | Pro | Cys | |
| | 1145 | | | | | 1150 | | | | | 1155 | | | | | |

| TCT | GAA | ATT | CAC | TAC | GAT | AGA | ATA | GGT | GGT | AGA | AAT | GCT | GCT | TCC | TTG | 684 |
|---|---|---|---|---|---|---|---|---|---|---|---|---|---|---|---|---|
| Ser | Glu | Ile | His | Tyr | Asp | Arg | Ile | Gly | Gly | Arg | Asn | Ala | Ala | Ser | Leu | |
| 1160 | | | | | 1165 | | | | | 1170 | | | | | 1175 | |

| GTT | AAT | ATG | GAC | GAC | CCT | GAT | GTC | TTG | GAA | GTT | TGG | AAT | TTG | GTT | TTC | 732 |
|---|---|---|---|---|---|---|---|---|---|---|---|---|---|---|---|---|
| Val | Asn | Met | Asp | Asp | Pro | Asp | Val | Leu | Glu | Val | Trp | Asn | Leu | Val | Phe | |
| | | | | 1180 | | | | | 1185 | | | | | 1190 | | |

| ATT | CAA | TTC | AAC | AGA | GAA | CAA | GAC | GGG | TCT | TTG | AAG | CCT | TTA | CCT | GCC | 780 |
|---|---|---|---|---|---|---|---|---|---|---|---|---|---|---|---|---|
| Ile | Gln | Phe | Asn | Arg | Glu | Gln | Asp | Gly | Ser | Leu | Lys | Pro | Leu | Pro | Ala | |
| | | | 1195 | | | | | 1200 | | | | | 1205 | | | |

| AAG | CAT | ATC | GAC | ACA | GGT | ATG | GGG | TTC | GAA | AGA | TTG | GTT | TCT | GTT | CTG | 828 |
|---|---|---|---|---|---|---|---|---|---|---|---|---|---|---|---|---|
| Lys | His | Ile | Asp | Thr | Gly | Met | Gly | Phe | Glu | Arg | Leu | Val | Ser | Val | Leu | |
| | | 1210 | | | | | 1215 | | | | | 1220 | | | | |

| CAA | GAT | GTT | AGA | TCT | AAC | TAT | GAT | ACC | GAT | GTT | TTC | ACA | CCT | TTG | TTC | 876 |
|---|---|---|---|---|---|---|---|---|---|---|---|---|---|---|---|---|
| Gln | Asp | Val | Arg | Ser | Asn | Tyr | Asp | Thr | Asp | Val | Phe | Thr | Pro | Leu | Phe | |
| 1225 | | | | | 1230 | | | | | 1235 | | | | | | |

| GAG | CGT | ATC | CAA | GAA | ATC | ACT | TCA | GTT | AGA | CCA | TAT | TCT | GGC | AAT | TTT | 924 |
|---|---|---|---|---|---|---|---|---|---|---|---|---|---|---|---|---|
| Glu | Arg | Ile | Gln | Glu | Ile | Thr | Ser | Val | Arg | Pro | Tyr | Ser | Gly | Asn | Phe | |
| 1240 | | | | | 1245 | | | | | 1250 | | | | | 1255 | |

| GGT | GAG | AAT | GAC | AAG | GAC | GGT | ATC | GAT | ACT | GCC | TAC | AGA | GTT | TTA | GCT | 972 |
|---|---|---|---|---|---|---|---|---|---|---|---|---|---|---|---|---|
| Gly | Glu | Asn | Asp | Lys | Asp | Gly | Ile | Asp | Thr | Ala | Tyr | Arg | Val | Leu | Ala | |
| | | | | 1260 | | | | | 1265 | | | | | 1270 | | |

| GAT | CAT | GTC | CGT | ACA | TTG | ACT | TTT | GCC | TTA | GCT | GAC | GGT | GGC | GTT | CCA | 1020 |
|---|---|---|---|---|---|---|---|---|---|---|---|---|---|---|---|---|
| Asp | His | Val | Arg | Thr | Leu | Thr | Phe | Ala | Leu | Ala | Asp | Gly | Gly | Val | Pro | |
| | | | 1275 | | | | | 1280 | | | | | 1285 | | | |

| AAC | AAT | GAA | GGT | AGA | GGA | TAT | GTT | TTG | AGA | CGC | ATT | CTA | AGA | AGA | GGT | 1068 |
|---|---|---|---|---|---|---|---|---|---|---|---|---|---|---|---|---|
| Asn | Asn | Glu | Gly | Arg | Gly | Tyr | Val | Leu | Arg | Arg | Ile | Leu | Arg | Arg | Gly | |
| | | | 1290 | | | | | 1295 | | | | | 1300 | | | |

| GCC | CGT | TAC | GCC | CGT | AAA | TAC | ATG | AAT | TAC | CCA | ATC | GGT | AAC | TTT | TTC | 1116 |
|---|---|---|---|---|---|---|---|---|---|---|---|---|---|---|---|---|

| | | | | | | | | | | | | | | |
|---|---|---|---|---|---|---|---|---|---|---|---|---|---|---|
| Ala | Arg | Tyr | Ala | Arg | Lys | Tyr | Met | Asn | Tyr | Pro | Ile | Gly | Asn | Phe | Phe |
| | 1305 | | | | 1310 | | | | | 1315 | | | | | |

| TCC | ACT | TTG | GCT | CCA | ACT | TTA | ATT | TCT | CAG | GTT | CAA | GAT | ATC | TTT | CCC | 1164 |
|---|---|---|---|---|---|---|---|---|---|---|---|---|---|---|---|---|
| Ser | Thr | Leu | Ala | Pro | Thr | Leu | Ile | Ser | Gln | Val | Gln | Asp | Ile | Phe | Pro | |
| 1320 | | | | | 1325 | | | | | 1330 | | | | | 1335 | |

| GAA | TTA | GCC | AAG | GAT | CCT | GCA | TTC | CTC | TTT | GAA | ATC | TTG | GAT | GAA | GAA | 1212 |
|---|---|---|---|---|---|---|---|---|---|---|---|---|---|---|---|---|
| Glu | Leu | Ala | Lys | Asp | Pro | Ala | Phe | Leu | Phe | Glu | Ile | Leu | Asp | Glu | Glu | |
| | | | | 1340 | | | | | 1345 | | | | | 1350 | | |

| GAA | GCT | TCT | TTC | GCT | AAG | ACC | TTG | GAT | CGT | GGT | GAA | AGA | CTA | TTT | GAA | 1260 |
|---|---|---|---|---|---|---|---|---|---|---|---|---|---|---|---|---|
| Glu | Ala | Ser | Phe | Ala | Lys | Thr | Leu | Asp | Arg | Gly | Glu | Arg | Leu | Phe | Glu | |
| | | | 1355 | | | | | 1360 | | | | | 1365 | | | |

| AAA | TAT | GCT | TCT | GCT | GCT | TCT | AAG | ACT | GAA | TCT | AAG | ACT | TTA | GAC | GGT | 1308 |
|---|---|---|---|---|---|---|---|---|---|---|---|---|---|---|---|---|
| Lys | Tyr | Ala | Ser | Ala | Ala | Ser | Lys | Thr | Glu | Ser | Lys | Thr | Leu | Asp | Gly | |
| | | 1370 | | | | | 1375 | | | | | 1380 | | | | |

| AAA | CAA | GTT | TGG | AGA | CTT | TAC | GAC | ACT | TAT | GGT | TTC | CCA | GTC | GAC | TTG | 1356 |
|---|---|---|---|---|---|---|---|---|---|---|---|---|---|---|---|---|
| Lys | Gln | Val | Trp | Arg | Leu | Tyr | Asp | Thr | Tyr | Gly | Phe | Pro | Val | Asp | Leu | |
| 1385 | | | | | 1390 | | | | | 1395 | | | | | | |

| ACT | GAA | TTG | ATG | GCT | GAA | GAA | CAA | GGC | TTG | AAG | ATT | GAT | GGA | CCC | GGT | 1404 |
|---|---|---|---|---|---|---|---|---|---|---|---|---|---|---|---|---|
| Thr | Glu | Leu | Met | Ala | Glu | Glu | Gln | Gly | Leu | Lys | Ile | Asp | Gly | Pro | Gly | |
| 1400 | | | | | 1405 | | | | | 1410 | | | | | 1415 | |

| TTC | GAA | AAG | GCC | AAA | CAA | GAG | TCA | TAC | GAA | GCA | TCC | AAA | AGA | GGT | GGT | 1452 |
|---|---|---|---|---|---|---|---|---|---|---|---|---|---|---|---|---|
| Phe | Glu | Lys | Ala | Lys | Gln | Glu | Ser | Tyr | Glu | Ala | Ser | Lys | Arg | Gly | Gly | |
| | | | | 1420 | | | | | 1425 | | | | | 1430 | | |

| AAG | AGG | ACC | AAA | AGT | GAT | TTG | ATT | AAG | TTA | AAC | GTC | CAT | GAA | TTA | TCC | 1500 |
|---|---|---|---|---|---|---|---|---|---|---|---|---|---|---|---|---|
| Lys | Arg | Thr | Lys | Ser | Asp | Leu | Ile | Lys | Leu | Asn | Val | His | Glu | Leu | Ser | |
| | | | 1435 | | | | | 1440 | | | | | 1445 | | | |

| GAG | TTG | AAC | GAT | GCT | AAG | GTG | CCC | AAG | ACT | AAT | GAT | GAA | TTC | AAA | TAC | 1548 |
|---|---|---|---|---|---|---|---|---|---|---|---|---|---|---|---|---|
| Glu | Leu | Asn | Asp | Ala | Lys | Val | Pro | Lys | Thr | Asn | Asp | Glu | Phe | Lys | Tyr | |
| | | 1450 | | | | | 1455 | | | | | 1460 | | | | |

| GGC | AGC | GCC | AAC | GTC | GAA | GGT | ACC | ATT | TTG | AAA | CTG | CAT | GAC | GGT | ACC | 1596 |
|---|---|---|---|---|---|---|---|---|---|---|---|---|---|---|---|---|
| Gly | Ser | Ala | Asn | Val | Glu | Gly | Thr | Ile | Leu | Lys | Leu | His | Asp | Gly | Thr | |
| | 1465 | | | | | 1470 | | | | | 1475 | | | | | |

| AAC | TTT | GTT | GAT | GAG | ATC | ACT | GAA | CCA | GGT | AAG | AAG | TAC | GGT | ATT | ATT | 1644 |
|---|---|---|---|---|---|---|---|---|---|---|---|---|---|---|---|---|
| Asn | Phe | Val | Asp | Glu | Ile | Thr | Glu | Pro | Gly | Lys | Lys | Tyr | Gly | Ile | Ile | |
| 1480 | | | | | 1485 | | | | | 1490 | | | | | 1495 | |

| TTG | GAT | AAA | ACA | TGT | TTC | TAC | GCC | GAA | CAA | GGT | GGT | CAA | GAA | TAT | GAC | 1692 |
|---|---|---|---|---|---|---|---|---|---|---|---|---|---|---|---|---|
| Leu | Asp | Lys | Thr | Cys | Phe | Tyr | Ala | Glu | Gln | Gly | Gly | Gln | Glu | Tyr | Asp | |
| | | | | 1500 | | | | | 1505 | | | | | 1510 | | |

| ACT | GGT | AAA | ATT | GTT | ATT | GAT | GAC | GCT | GCT | GAG | TTT | AAT | GTT | GAA | AAT | 1740 |
|---|---|---|---|---|---|---|---|---|---|---|---|---|---|---|---|---|
| Thr | Gly | Lys | Ile | Val | Ile | Asp | Asp | Ala | Ala | Glu | Phe | Asn | Val | Glu | Asn | |
| | | | 1515 | | | | | 1520 | | | | | 1525 | | | |

| GTT | CAA | TTG | TAT | AAC | GGT | TTT | GTT | TTC | CAC | ACC | GGG | TCT | TTA | GAA | GAA | 1788 |
|---|---|---|---|---|---|---|---|---|---|---|---|---|---|---|---|---|
| Val | Gln | Leu | Tyr | Asn | Gly | Phe | Val | Phe | His | Thr | Gly | Ser | Leu | Glu | Glu | |
| | | 1530 | | | | | 1535 | | | | | 1540 | | | | |

| GGT | AAG | TTG | TCT | GTC | GGT | GAC | AAG | ATT | ATC | GCT | TCA | TTC | GAT | GAA | CTA | 1836 |
|---|---|---|---|---|---|---|---|---|---|---|---|---|---|---|---|---|
| Gly | Lys | Leu | Ser | Val | Gly | Asp | Lys | Ile | Ile | Ala | Ser | Phe | Asp | Glu | Leu | |
| | 1545 | | | | | 1550 | | | | | 1555 | | | | | |

| CGT | CGA | TTC | CCT | ATT | AAG | AAC | AAT | CAT | ACT | GGT | ACA | CAT | ATC | TTA | AAC | 1884 |
|---|---|---|---|---|---|---|---|---|---|---|---|---|---|---|---|---|
| Arg | Arg | Phe | Pro | Ile | Lys | Asn | Asn | His | Thr | Gly | Thr | His | Ile | Leu | Asn | |
| 1560 | | | | | 1565 | | | | | 1570 | | | | | 1575 | |

| TTT | GCT | CTG | AAG | GAA | ACT | TTG | GGT | AAT | GAT | GTC | GAT | CAA | AAG | GGT | TCT | 1932 |
|---|---|---|---|---|---|---|---|---|---|---|---|---|---|---|---|---|
| Phe | Ala | Leu | Lys | Glu | Thr | Leu | Gly | Asn | Asp | Val | Asp | Gln | Lys | Gly | Ser | |
| | | | | 1580 | | | | | 1585 | | | | | 1590 | | |

| TTG | GTT | GCC | CCA | GAA | AAA | TTG | AGA | TTC | GAT | TTC | TCT | CAT | AAA | AAG | GCT | 1980 |
|---|---|---|---|---|---|---|---|---|---|---|---|---|---|---|---|---|
| Leu | Val | Ala | Pro | Glu | Lys | Leu | Arg | Phe | Asp | Phe | Ser | His | Lys | Lys | Ala | |
| | | | 1595 | | | | | 1600 | | | | | 1605 | | | |

| GTG | TCA | AAT | GAA | GAA | TTG | AAA | AAA | GTT | GAA | GAT | ATC | TGT | AAT | GAG | CAA | 2028 |
|---|---|---|---|---|---|---|---|---|---|---|---|---|---|---|---|---|
| Val | Ser | Asn | Glu | Glu | Leu | Lys | Lys | Val | Glu | Asp | Ile | Cys | Asn | Glu | Gln | |
| | | 1610 | | | | | 1615 | | | | | 1620 | | | | |

| ATT | AAA | GAA | AAC | TTA | CAA | GTG | TTT | TAC | AAG | GAA | ATT | CCA | TTG | GAC | TTG | 2076 |

| | | | | | | | | | | | | | | | |
|---|---|---|---|---|---|---|---|---|---|---|---|---|---|---|---|
| Ile | Lys | Glu | Asn | Leu | Gln | Val | Phe | Tyr | Lys | Glu | Ile | Pro | Leu | Asp | Leu |
| | 1625 | | | | 1630 | | | | | 1635 | | | | | |

| GCC | AAA | TCC | ATT | GAT | GGT | GTT | CGT | GCT | GTC | TTT | GGT | GAG | ACT | TAC | CCA | 2124 |
|---|---|---|---|---|---|---|---|---|---|---|---|---|---|---|---|---|
| Ala | Lys | Ser | Ile | Asp | Gly | Val | Arg | Ala | Val | Phe | Gly | Glu | Thr | Tyr | Pro | |
| 1640 | | | | | 1645 | | | | | 1650 | | | | | 1655 | |

| GAT | CCA | GTT | CGT | GTA | GTT | TCT | GTT | GGT | AAG | CCA | ATC | GAA | GAA | TTG | TTG | 2172 |
|---|---|---|---|---|---|---|---|---|---|---|---|---|---|---|---|---|
| Asp | Pro | Val | Arg | Val | Val | Ser | Val | Gly | Lys | Pro | Ile | Glu | Glu | Leu | Leu | |
| | | | | 1660 | | | | | 1665 | | | | | 1670 | | |

| GCC | AAC | CCA | GCT | AAC | GAA | GAG | TGG | ACC | AAG | TAT | TCT | ATT | GAA | TTT | TGC | 2220 |
|---|---|---|---|---|---|---|---|---|---|---|---|---|---|---|---|---|
| Ala | Asn | Pro | Ala | Asn | Glu | Glu | Trp | Thr | Lys | Tyr | Ser | Ile | Glu | Phe | Cys | |
| | | 1675 | | | | | 1680 | | | | | 1685 | | | | |

| GGT | GGT | ACC | CAT | GTC | AAC | AAG | ACA | GGC | GAT | ATT | AAA | TAC | TTC | GTC | ATT | 2268 |
|---|---|---|---|---|---|---|---|---|---|---|---|---|---|---|---|---|
| Gly | Gly | Thr | His | Val | Asn | Lys | Thr | Gly | Asp | Ile | Lys | Tyr | Phe | Val | Ile | |
| | | 1690 | | | | | 1695 | | | | | 1700 | | | | |

| TTA | GAA | GAG | AGC | GGT | ATT | GCA | AAG | GGT | ATC | AGA | AGA | ATT | GTT | GCT | GTT | 2316 |
|---|---|---|---|---|---|---|---|---|---|---|---|---|---|---|---|---|
| Leu | Glu | Glu | Ser | Gly | Ile | Ala | Lys | Gly | Ile | Arg | Arg | Ile | Val | Ala | Val | |
| 1705 | | | | | 1710 | | | | | 1715 | | | | | | |

| ACT | GGA | ACT | GAA | GCC | TTT | GAA | GCT | CAA | AGA | TTG | GCT | GAA | CAG | TTT | GCT | 2364 |
|---|---|---|---|---|---|---|---|---|---|---|---|---|---|---|---|---|
| Thr | Gly | Thr | Glu | Ala | Phe | Glu | Ala | Gln | Arg | Leu | Ala | Glu | Gln | Phe | Ala | |
| 1720 | | | | | 1725 | | | | | 1730 | | | | | 1735 | |

| GCT | GAT | TTG | GAT | GCT | GCA | GAC | AAG | CTG | CCG | TTC | TCT | CCA | ATC | AAA | GAA | 2412 |
|---|---|---|---|---|---|---|---|---|---|---|---|---|---|---|---|---|
| Ala | Asp | Leu | Asp | Ala | Ala | Asp | Lys | Leu | Pro | Phe | Ser | Pro | Ile | Lys | Glu | |
| | | | | 1740 | | | | | 1745 | | | | | 1750 | | |

| AAG | AAG | TTG | AAG | GAA | CTT | GGT | GTC | AAA | CTT | GGT | CAA | CTT | TCA | ATT | TCT | 2460 |
|---|---|---|---|---|---|---|---|---|---|---|---|---|---|---|---|---|
| Lys | Lys | Leu | Lys | Glu | Leu | Gly | Val | Lys | Leu | Gly | Gln | Leu | Ser | Ile | Ser | |
| | | | | 1755 | | | | | 1760 | | | | | 1765 | | |

| GTT | ATC | ACA | AAA | AAT | GAA | CTG | AAG | CAG | AAA | TTT | AAC | AAA | ATT | GAA | AAA | 2508 |
|---|---|---|---|---|---|---|---|---|---|---|---|---|---|---|---|---|
| Val | Ile | Thr | Lys | Asn | Glu | Leu | Lys | Gln | Lys | Phe | Asn | Lys | Ile | Glu | Lys | |
| | | 1770 | | | | | 1775 | | | | | 1780 | | | | |

| GCA | GTG | AAG | GAT | GAA | GTT | AAG | TCA | AGG | GCC | AAA | AAA | GAA | AAC | AAA | CAA | 2556 |
|---|---|---|---|---|---|---|---|---|---|---|---|---|---|---|---|---|
| Ala | Val | Lys | Asp | Glu | Val | Lys | Ser | Arg | Ala | Lys | Lys | Glu | Asn | Lys | Gln | |
| | 1785 | | | | | 1790 | | | | | 1795 | | | | | |

| ACT | CTT | GAT | GAA | GTG | AAG | ACA | TTT | TTG | CAA | ACC | AAT | GAG | AAT | GCT | CCA | 2604 |
|---|---|---|---|---|---|---|---|---|---|---|---|---|---|---|---|---|
| Thr | Leu | Asp | Glu | Val | Lys | Thr | Phe | Leu | Gln | Thr | Asn | Glu | Asn | Ala | Pro | |
| 1800 | | | | | 1805 | | | | | 1810 | | | | | 1815 | |

| TAC | CTA | GTT | AAA | TTC | ATT | GAT | ATT | TCT | CCA | AAT | GCT | AAA | GCT | ATC | ACT | 2652 |
|---|---|---|---|---|---|---|---|---|---|---|---|---|---|---|---|---|
| Tyr | Leu | Val | Lys | Phe | Ile | Asp | Ile | Ser | Pro | Asn | Ala | Lys | Ala | Ile | Thr | |
| | | | | 1820 | | | | | 1825 | | | | | 1830 | | |

| GAA | GCG | ATC | AAC | TAC | ATG | AAA | TCC | AAT | GAT | TCT | GTC | AAA | GAC | AAG | TCA | 2700 |
|---|---|---|---|---|---|---|---|---|---|---|---|---|---|---|---|---|
| Glu | Ala | Ile | Asn | Tyr | Met | Lys | Ser | Asn | Asp | Ser | Val | Lys | Asp | Lys | Ser | |
| | | | 1835 | | | | | 1840 | | | | | 1845 | | | |

| ATC | TAT | TTA | TTG | GCA | GGT | AAT | GAC | CCT | GAA | GGT | CGT | GTT | GCT | CAC | GGT | 2748 |
|---|---|---|---|---|---|---|---|---|---|---|---|---|---|---|---|---|
| Ile | Tyr | Leu | Leu | Ala | Gly | Asn | Asp | Pro | Glu | Gly | Arg | Val | Ala | His | Gly | |
| | | | 1850 | | | | | 1855 | | | | | 1860 | | | |

| TGT | TAC | ATC | TCC | AAT | GCT | GCT | TTA | GCC | AAG | GGT | ATT | GAT | GGT | TCT | GCG | 2796 |
|---|---|---|---|---|---|---|---|---|---|---|---|---|---|---|---|---|
| Cys | Tyr | Ile | Ser | Asn | Ala | Ala | Leu | Ala | Lys | Gly | Ile | Asp | Gly | Ser | Ala | |
| | 1865 | | | | | 1870 | | | | | 1875 | | | | | |

| CTT | GCC | AAA | AAG | GTG | TCC | AGT | ATC | ATC | GGC | GGT | AAG | GCT | GGT | GGT | AAA | 2844 |
|---|---|---|---|---|---|---|---|---|---|---|---|---|---|---|---|---|
| Leu | Ala | Lys | Lys | Val | Ser | Ser | Ile | Ile | Gly | Gly | Lys | Ala | Gly | Gly | Lys | |
| 1880 | | | | | 1885 | | | | | 1890 | | | | | 1895 | |

| GGT | AAT | GTT | TTC | CAA | GGT | ATG | GGT | GAT | AAA | CCA | GCC | GCT | ATA | AAG | GAT | 2892 |
|---|---|---|---|---|---|---|---|---|---|---|---|---|---|---|---|---|
| Gly | Asn | Val | Phe | Gln | Gly | Met | Gly | Asp | Lys | Pro | Ala | Ala | Ile | Lys | Asp | |
| | | | | 1900 | | | | | 1905 | | | | | 1910 | | |

| GCA | GTT | GAT | GAT | TTG | GAA | AGT | TTG | TTC | AAG | GAG | AAG | CTT | TCC | ATT | | 2937 |
|---|---|---|---|---|---|---|---|---|---|---|---|---|---|---|---|---|
| Ala | Val | Asp | Asp | Leu | Glu | Ser | Leu | Phe | Lys | Glu | Lys | Leu | Ser | Ile | | |
| | | | 1915 | | | | | 1920 | | | | | 1925 | | | |

| TAAGAAGTTA | AAATAAAACG | AAAAATAATG | CATAGGATTC | TTTTCTTTA | TTTTG | 2992 |
|---|---|---|---|---|---|---|

( 2 ) INFORMATION FOR SEQ ID NO:4:

( i ) SEQUENCE CHARACTERISTICS:
    ( A ) LENGTH: 958 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met Thr Ile Gly Asp Lys Gln Lys Trp Thr Ala Thr Asn Val Arg Asn
 1               5                  10                  15

Thr Phe Leu Asp Tyr Phe Lys Ser Lys Glu His Lys Phe Val Lys Ser
                20                  25                  30

Ser Pro Val Val Pro Phe Asp Asp Pro Thr Leu Leu Phe Ala Asn Ala
                35                  40                  45

Gly Met Asn Gln Tyr Lys Pro Ile Phe Leu Gly Thr Val Asp Pro Ala
     50                  55                  60

Ser Asp Phe Tyr Thr Leu Lys Arg Ala Tyr Asn Ser Gln Lys Cys Ile
 65                  70                  75                  80

Arg Ala Gly Gly Lys His Asn Asp Leu Glu Asp Val Gly Lys Asp Ser
                85                  90                  95

Tyr His His Thr Phe Phe Glu Met Leu Gly Asn Trp Ser Phe Gly Asp
            100                 105                 110

Tyr Phe Lys Lys Glu Ala Ile Thr Tyr Ser Trp Thr Leu Leu Thr Glu
            115                 120                 125

Val Tyr Gly Ile Pro Lys Asp Ser Leu Tyr Val Thr Tyr Phe Glu Gly
        130                 135                 140

Asp Glu Lys Leu Gly Leu Glu Pro Asp Thr Glu Ala Arg Glu Leu Trp
145                 150                 155                 160

Lys Asn Val Gly Val Pro Asp Asp His Ile Leu Pro Gly Asn Ala Lys
                165                 170                 175

Asp Asn Phe Trp Glu Met Gly Asp Gln Gly Pro Cys Gly Pro Cys Ser
            180                 185                 190

Glu Ile His Tyr Asp Arg Ile Gly Gly Arg Asn Ala Ala Ser Leu Val
        195                 200                 205

Asn Met Asp Asp Pro Asp Val Leu Glu Val Trp Asn Leu Val Phe Ile
210                 215                 220

Gln Phe Asn Arg Glu Gln Asp Gly Ser Leu Lys Pro Leu Pro Ala Lys
225                 230                 235                 240

His Ile Asp Thr Gly Met Gly Phe Glu Arg Leu Val Ser Val Leu Gln
                245                 250                 255

Asp Val Arg Ser Asn Tyr Asp Thr Asp Val Phe Thr Pro Leu Phe Glu
            260                 265                 270

Arg Ile Gln Glu Ile Thr Ser Val Arg Pro Tyr Ser Gly Asn Phe Gly
        275                 280                 285

Glu Asn Asp Lys Asp Gly Ile Asp Thr Ala Tyr Arg Val Leu Ala Asp
290                 295                 300

His Val Arg Thr Leu Thr Phe Ala Leu Ala Asp Gly Gly Val Pro Asn
305                 310                 315                 320

Asn Glu Gly Arg Gly Tyr Val Leu Arg Arg Ile Leu Arg Arg Gly Ala
                325                 330                 335

Arg Tyr Ala Arg Lys Tyr Met Asn Tyr Pro Ile Gly Asn Phe Phe Ser
            340                 345                 350

Thr Leu Ala Pro Thr Leu Ile Ser Gln Val Gln Asp Ile Phe Pro Glu
        355                 360                 365

Leu Ala Lys Asp Pro Ala Phe Leu Phe Glu Ile Leu Asp Glu Glu Glu
370                 375                 380
```

| | | | | | | | | | | | | | | |
|---|---|---|---|---|---|---|---|---|---|---|---|---|---|---|
| Ala | Ser | Phe | Ala | Lys | Thr | Leu | Asp | Arg | Gly | Glu | Arg | Leu | Phe | Glu | Lys |
| 385 | | | | 390 | | | | | 395 | | | | | | 400 |
| Tyr | Ala | Ser | Ala | Ala | Ser | Lys | Thr | Glu | Ser | Lys | Thr | Leu | Asp | Gly | Lys |
| | | | | 405 | | | | 410 | | | | | | 415 | |
| Gln | Val | Trp | Arg | Leu | Tyr | Asp | Thr | Tyr | Gly | Phe | Pro | Val | Asp | Leu | Thr |
| | | | 420 | | | | | 425 | | | | | 430 | | |
| Glu | Leu | Met | Ala | Glu | Glu | Gln | Gly | Leu | Lys | Ile | Asp | Gly | Pro | Gly | Phe |
| | | 435 | | | | | 440 | | | | | 445 | | | |
| Glu | Lys | Ala | Lys | Gln | Glu | Ser | Tyr | Glu | Ala | Ser | Lys | Arg | Gly | Gly | Lys |
| | 450 | | | | | 455 | | | | | 460 | | | | |
| Arg | Thr | Lys | Ser | Asp | Leu | Ile | Lys | Leu | Asn | Val | His | Glu | Leu | Ser | Glu |
| 465 | | | | | 470 | | | | | 475 | | | | | 480 |
| Leu | Asn | Asp | Ala | Lys | Val | Pro | Lys | Thr | Asn | Asp | Glu | Phe | Lys | Tyr | Gly |
| | | | | 485 | | | | | 490 | | | | | 495 | |
| Ser | Ala | Asn | Val | Glu | Gly | Thr | Ile | Leu | Lys | Leu | His | Asp | Gly | Thr | Asn |
| | | | 500 | | | | | 505 | | | | | 510 | | |
| Phe | Val | Asp | Glu | Ile | Thr | Glu | Pro | Gly | Lys | Lys | Tyr | Gly | Ile | Ile | Leu |
| | | 515 | | | | | 520 | | | | | 525 | | | |
| Asp | Lys | Thr | Cys | Phe | Tyr | Ala | Glu | Gln | Gly | Gly | Gln | Glu | Tyr | Asp | Thr |
| | 530 | | | | | 535 | | | | | 540 | | | | |
| Gly | Lys | Ile | Val | Ile | Asp | Asp | Ala | Ala | Glu | Phe | Asn | Val | Glu | Asn | Val |
| 545 | | | | | 550 | | | | | 555 | | | | | 560 |
| Gln | Leu | Tyr | Asn | Gly | Phe | Val | Phe | His | Thr | Gly | Ser | Leu | Glu | Glu | Gly |
| | | | | 565 | | | | | 570 | | | | | 575 | |
| Lys | Leu | Ser | Val | Gly | Asp | Lys | Ile | Ile | Ala | Ser | Phe | Asp | Glu | Leu | Arg |
| | | | 580 | | | | | 585 | | | | | 590 | | |
| Arg | Phe | Pro | Ile | Lys | Asn | Asn | His | Thr | Gly | Thr | His | Ile | Leu | Asn | Phe |
| | | 595 | | | | | 600 | | | | | 605 | | | |
| Ala | Leu | Lys | Glu | Thr | Leu | Gly | Asn | Asp | Val | Asp | Gln | Lys | Gly | Ser | Leu |
| | 610 | | | | | 615 | | | | | 620 | | | | |
| Val | Ala | Pro | Glu | Lys | Leu | Arg | Phe | Asp | Phe | Ser | His | Lys | Lys | Ala | Val |
| 625 | | | | | 630 | | | | | 635 | | | | | 640 |
| Ser | Asn | Glu | Glu | Leu | Lys | Lys | Val | Glu | Asp | Ile | Cys | Asn | Glu | Gln | Ile |
| | | | | 645 | | | | | 650 | | | | | 655 | |
| Lys | Glu | Asn | Leu | Gln | Val | Phe | Tyr | Lys | Glu | Ile | Pro | Leu | Asp | Leu | Ala |
| | | | 660 | | | | | 665 | | | | | 670 | | |
| Lys | Ser | Ile | Asp | Gly | Val | Arg | Ala | Val | Phe | Gly | Glu | Thr | Tyr | Pro | Asp |
| | | 675 | | | | | 680 | | | | | 685 | | | |
| Pro | Val | Arg | Val | Val | Ser | Val | Gly | Lys | Pro | Ile | Glu | Glu | Leu | Leu | Ala |
| | 690 | | | | | 695 | | | | | 700 | | | | |
| Asn | Pro | Ala | Asn | Glu | Glu | Trp | Thr | Lys | Tyr | Ser | Ile | Glu | Phe | Cys | Gly |
| 705 | | | | | 710 | | | | | 715 | | | | | 720 |
| Gly | Thr | His | Val | Asn | Lys | Thr | Gly | Asp | Ile | Lys | Tyr | Phe | Val | Ile | Leu |
| | | | | 725 | | | | | 730 | | | | | 735 | |
| Glu | Glu | Ser | Gly | Ile | Ala | Lys | Gly | Ile | Arg | Arg | Ile | Val | Ala | Val | Thr |
| | | | 740 | | | | | 745 | | | | | 750 | | |
| Gly | Thr | Glu | Ala | Phe | Glu | Ala | Gln | Arg | Leu | Ala | Glu | Gln | Phe | Ala | Ala |
| | | 755 | | | | | 760 | | | | | 765 | | | |
| Asp | Leu | Asp | Ala | Ala | Asp | Lys | Leu | Pro | Phe | Ser | Pro | Ile | Lys | Glu | Lys |
| | 770 | | | | | 775 | | | | | 780 | | | | |
| Lys | Leu | Lys | Glu | Leu | Gly | Val | Lys | Leu | Gly | Gln | Leu | Ser | Ile | Ser | Val |
| 785 | | | | | 790 | | | | | 795 | | | | | 800 |
| Ile | Thr | Lys | Asn | Glu | Leu | Lys | Gln | Lys | Phe | Asn | Lys | Ile | Glu | Lys | Ala |

|   |   |   |   |   | 805 |   |   |   |   | 810 |   |   |   |   | 815 |
|---|---|---|---|---|---|---|---|---|---|---|---|---|---|---|---|

Val Lys Asp Glu Val Lys Ser Arg Ala Lys Lys Glu Asn Lys Gln Thr
                820                     825                 830

Leu Asp Glu Val Lys Thr Phe Leu Gln Thr Asn Glu Asn Ala Pro Tyr
            835                 840                 845

Leu Val Lys Phe Ile Asp Ile Ser Pro Asn Ala Lys Ala Ile Thr Glu
        850                 855                 860

Ala Ile Asn Tyr Met Lys Ser Asn Asp Ser Val Lys Asp Lys Ser Ile
865                     870                 875                 880

Tyr Leu Leu Ala Gly Asn Asp Pro Glu Gly Arg Val Ala His Gly Cys
                885                     890                 895

Tyr Ile Ser Asn Ala Ala Leu Ala Lys Gly Ile Asp Gly Ser Ala Leu
            900                 905                 910

Ala Lys Lys Val Ser Ser Ile Ile Gly Gly Lys Ala Gly Gly Lys Gly
        915                 920                 925

Asn Val Phe Gln Gly Met Gly Asp Lys Pro Ala Ala Ile Lys Asp Ala
    930                 935                 940

Val Asp Asp Leu Glu Ser Leu Phe Lys Glu Lys Leu Ser Ile
945                 950                 955

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="PCR primer"

(xi) SEQUENCE DESCRIPTION: SEQ ID NO:5:

TTYRCYAAYG CYGGYATGAA YCARTTYAAR          30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="PCR primer"

(xi) SEQUENCE DESCRIPTION: SEQ ID NO:6:

RTTYCCCATC ATYTCRAARA AYGTRTGRTG          30

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="hybridization probe"

(xi) SEQUENCE DESCRIPTION: SEQ ID NO:7:

TCTCACCCCA TGGCAAAGCT G          21

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic oligonucleotide"

( x i ) SEQUENCE DESCRIPTION: SEQ ID NO:8:

TTTGGGGTGA CTTTCCATAT GGACTCTACT CTAACAG                        37